US011739387B2

(12) United States Patent
Guo et al.

(10) Patent No.: US 11,739,387 B2
(45) Date of Patent: Aug. 29, 2023

(54) METHODS AND COMPOSITIONS FOR IDENTIFICATION OF TUMOR MODELS

(71) Applicant: CROWN BIOSCIENCE (SUZHOU) INC., Suzhou (CN)

(72) Inventors: Sheng Guo, Suzhou (CN); Xiaobo Chen, Suzhou (CN); Wubin Qian, Suzhou (CN); Henry Li, Suzhou (CN)

(73) Assignee: CROWN BIOSCIENCE (SUZHOU) INC., Suzhou (CN)

( * ) Notice: Subject to any disclaimer, the term of this patent is extended or adjusted under 35 U.S.C. 154(b) by 0 days.

(21) Appl. No.: 17/329,176

(22) Filed: May 25, 2021

(65) Prior Publication Data
US 2021/0277486 A1 Sep. 9, 2021

Related U.S. Application Data

(63) Continuation-in-part of application No. PCT/CN2020/079067, filed on Mar. 12, 2020.

(30) Foreign Application Priority Data

Mar. 12, 2019 (WO) ............... PCT/CN2019/077750

(51) Int. Cl.
C12Q 1/6886 (2018.01)
(52) U.S. Cl.
CPC ..... *C12Q 1/6886* (2013.01); *C12Q 2600/156* (2013.01); *C12Q 2600/16* (2013.01)
(58) Field of Classification Search
None
See application file for complete search history.

(56) References Cited

PUBLICATIONS

Guo et al. (Forensic science international Genetics 2016 vol. 25 p. 73-84) (Year: 2016).*
Almeida et al. (PLOS Biology 2016 vol. 14 p. 1-9) (Year: 2016).*
Liang et al. (PLOS ONE 2015 vol. 10 p. 1-14) (Year: 2015).*
Castro et al. (International Journal of Cancer 2013 vol. 132 p. 308-314) (Year: 2013).*
Didion et al. (Genomics 2014 vol. 15 p. 1-11) (Year: 2014).*
Almeida JL et al., Standards for Cell Line Authentication and Beyond, Plos Biology, (Jun. 14, 2016), No. 6 vol. 14, pp. 1-9.
Liang-Chu Mmy et al., Human Biosample Authentication Using the High-Throughput, Cost-Effective SNPtraceTM System, Plos One, (Feb. 25, 2015), No. 2 vol. 10, pp. 1-14.
Castro F et al., High-throughput SNP-based authentication of human cell lines, International Journal of Cancer, (Jan. 15, 2013), No. 2 vol. 132, pp. 308-314.
Didion JP et al., SNP array profiling of mouse cell lines identifies their strains of origin and reveals crosscontamination and widespread aneuploidy, Genomics, (Oct. 3, 2014), vol. 15, article No. 847, pp. 1-11.
The international search report of PCT application No. PCT/CN2020/079067, dated Jul. 14, 2020.

* cited by examiner

*Primary Examiner* — Katherine D Salmon
(74) *Attorney, Agent, or Firm* — Jun He Law Offices P.C.; Yi Zhang

(57) ABSTRACT

The disclosure provides methods and compositions, e.g., kits, for identifying or authenticating a sample, e.g., a tumor model, based on the genotype of the sample at a group of SNP loci.

9 Claims, 5 Drawing Sheets

Specification includes a Sequence Listing.

SEQUENCE LISTING

<160> NUMBER OF SEQ ID NOS: 652

<210> SEQ ID NO 1
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 1
aatcacagcc aatattctca agttccaaga naccgatggc aaacacctgc tgccaaagat    60
c    61

<210> SEQ ID NO 2
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or c

<400> SEQUENCE: 2
gcagagccgc cctctccgcc actgtccccc nccacgagcc ccccttccac ctggaccggg    60
a    61

<210> SEQ ID NO 3
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 3
gtgcttgaac tcaaacatgt tcctctgcac naaagtcttg cggatcttct ggttggtcca    60
g    61

<210> SEQ ID NO 4
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 4
caatactcgc cccaccgtgt gataggctct nctggtaact ttaatgtatg tggggcaacc    60
a    61

<210> SEQ ID NO 5
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 5
ctaaatctgt tgaagttacc tccggagtcc natctagaaa gcatcatagt cttcagagtc    60
c    61

<210> SEQ ID NO 6
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t -continued

<400> SEQUENCE: 6
agtagtccta ttagcccaga ggcgatgtct ntcatgatgt ccacgtcact gtagtatggt    60
c                                                                    61

<210> SEQ ID NO 7
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 7
ggctgcaacg gggcgggctc tgctgcgtca ncacatggac atcactggag aggaaaaccc    60
a                                                                    61

<210> SEQ ID NO 8
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 8
gcagagctcc ggctgcgatg gggccaaatc ntccttaaga acgaccacca ggaagatttc    60
t                                                                    61

<210> SEQ ID NO 9
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t, a or c

<400> SEQUENCE: 9
ggctaacatg tgcagctctc tcttcagacg ngaagctctc tgcatgatcc ccaagtagaa    60
g                                                                    61

<210> SEQ ID NO 10
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or c

<400> SEQUENCE: 10
tctggggtga acatattcta gccctgaaga ntctgaagtt agacaagatg gttggctggc    60
t                                                                    61

<210> SEQ ID NO 11
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 11
ggagctggca gctaccagca cactgcctcc nccgtcaata aaggcactga tggtctccac        60
g                                                                       61

<210> SEQ ID NO 12
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 12
attgagcttg atgggcaggt ctctgtgtga ntgtacccat tttgcatatg caggatacat        60
t                                                                       61

<210> SEQ ID NO 13
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 13
attccatgcc ctcaaacttc acctttttt ntcttgctct tccttctcta ttttgtggga        60
c                                                                       61

<210> SEQ ID NO 14
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 14
caaggaccag gcaacagcag agcagcctta ngcatcttgg aagatcccga ggttagattc        60
t                                                                       61

<210> SEQ ID NO 15
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 15
gtcggtccac tccgcttggt tatctgcttc naccaaatta gtacctggga aggaaaaaga        60
a                                                                       61

<210> SEQ ID NO 16
<211> LENGTH: 61
<212> TYPE: DNA
<213> ORGANISM: Homo sapiens
<220> FEATURE:
<221> NAME/KEY: misc_feature
<222> LOCATION: (31)..(31)

<223> OTHER INFORMATION: n is g or c

<400> SEQUENCE: 16
ccacgcgctc cagtagcggc ccgtcctcgc ngggccgcaa acatggcccg acggctgcta        60
g        61

<210> SEQ ID NO 17
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t, a or c

<400> SEQUENCE: 17
acatacctgc tctgtcttca tgtggaactc nttgagctca tcctctgtga ggggaaggca        60
a        61

<210> SEQ ID NO 18
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 18
tgggtccccc caggaagaga gggcaggtga nttagaatgt ttctccccga agacaggacc        60
t        61

<210> SEQ ID NO 19
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 19
tgtcaatcat agaccaacgg gcatattcca ngattaaaag ccgtacatct ctgtacagag        60
g        61

<210> SEQ ID NO 20
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 20
tgaaccgtgt tctttccagg aacctgttgg nccagttggt ttcaagccag agacattcag        60
a        61

<210> SEQ ID NO 21
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 21
acgacggagt cttttccttt cttgtcgatg nagtttctca gcctcctgtt gcttcttctg    60
c                                                                   61

<210> SEQ ID NO 22
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 22
ctctcggcga ggtggcgcca cgttttcaca ncagccttct cagagttgta cgtggagctg    60
a                                                                   61

<210> SEQ ID NO 23
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 23
tcttctagag gcagggagct caccaccctt ncagtgtcca acttctttag taattacaca    60
c                                                                   61

<210> SEQ ID NO 24
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or absent

<400> SEQUENCE: 24
tgtctgggag gcagccacag agctggctgc nggctccctg cccacccagc gctactctcc    60
t                                                                   61

<210> SEQ ID NO 25
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 25
tctttcagat ccctcccacc tcctgaaatg ntctaattaa aaacatccag gcttgtatag    60
a                                                                   61

<210> SEQ ID NO 26
<211> LENGTH: 61
<212> TYPE: DNA
<213> ORGANISM: Homo sapiens
<220> FEATURE:

```
<221> NAME/KEY: misc_feature
<222> LOCATION: (31)..(31)
<223> OTHER INFORMATION: n is t, a or c

<400> SEQUENCE: 26
aataaatact attaccaacc tctttcgaat nctagcatta aacagtggtg cctcaaaacg    60
t                                                                   61

<210> SEQ ID NO 27
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or a

<400> SEQUENCE: 27
acacgcactt caatggggca gggtccccc nagatggagt gaaatgctcc cctggaggac    60
c                                                                   61

<210> SEQ ID NO 28
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 28
atcctcctca tcctcctcac tgtcatcatc ntcctcttca tcactgtctt ccttcttggc    60
a                                                                   61

<210> SEQ ID NO 29
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 29
gacttgtcgg caccaggaag agagccaggg nacttcaatc cagaaagcag agaagatacc    60
a                                                                   61

<210> SEQ ID NO 30
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 30
ggggacagat ggcctttctc gggtgtgctt ngaggagaaa ctgtacgaat gaagtgagcc    60
g                                                                   61

<210> SEQ ID NO 31
<211> LENGTH: 61
<212> TYPE: DNA
<213> ORGANISM: Homo sapiens
```

<220> FEATURE:
<221> NAME/KEY: misc_feature
<222> LOCATION: (31)..(31)
<223> OTHER INFORMATION: n is a or g

<400> SEQUENCE: 31
gggaaggccc acgtctggct gtttacacca ntctagggaa aaattctgcc aagaaagaac    60
c    61

<210> SEQ ID NO 32
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 32
cagctgtgtc agctctaccc ccgactgaaa ntgctggcat ttggagcaaa gccggattcc    60
a    61

<210> SEQ ID NO 33
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 33
gttgacagtt tcagtgtaag ttcgagcctt nggagggttg gggacccccag atgaagcaga    60 a    61

<210> SEQ ID NO 34
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 34
tggtctggtg accacaccta gaacaactgc nttaagatta aataatgttg gatacagctt    60
g    61

<210> SEQ ID NO 35
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 35
ccggatccac tggtcctcct tgtccctcac ntcgaagtac ccactgccat ccaggatgta    60
g    61

<210> SEQ ID NO 36
<211> LENGTH: 61
<212> TYPE: DNA

<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 36

```
acccttttt gtttttaac agacttgtaa ngaaaccaag gatgttagtg ctctgacaaa    60
a                                                                 61
```

<210> SEQ ID NO 37
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or t

<400> SEQUENCE: 37

```
tgtttcttaa tggtgtatgg attcttcaac ntatgacaga acctgcattt aaaagcacat    60
a                                                                   61
```

<210> SEQ ID NO 38
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 38

```
aaaagagttg ttagaaaaaa agccgtggca ncttcagggg gaagtgacag cacagaagag    60
g                                                                   61
```

<210> SEQ ID NO 39
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 39

```
atttcagggt gatgctggtt tgactggacg naaaatcatt gtggacactt atggcggttg    60
g                                                                   61
```

<210> SEQ ID NO 40
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 40

```
ctcatagctc cgtcacacac atgtacaaga nggtgaagca ggtggtatca cacaacaaat    60
t                                                                   61
```

<210> SEQ ID NO 41
<211> LENGTH: 61

```
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 41
tatattcctc ttgctccaga acaaacatgt nccaattgaa gaattgttgt aatttttcat    60
t                                                                   61

<210> SEQ ID NO 42
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 42
caaggagcaa atagtttctt tttcttacgg nacttcgcta ggaatttaag cgcctggaag    60
a                                                                   61

<210> SEQ ID NO 43
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or t

<400> SEQUENCE: 43
caaaaacttc gaccgagaga ttggccacaa naccccagg tgagagccag gcccaaggcc     60
t                                                                   61

<210> SEQ ID NO 44
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 44
catatttgct gccatgtgaa ataaggagaa ntgactgaat gttgacagca acattggaga    60
a                                                                   61

<210> SEQ ID NO 45
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 45
ccccagtctc cccacaggta tgcctataac ntaagtctaa aggaggtgat gcaggtactg    60
a                                                                   61

<210> SEQ ID NO 46
```

<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 46
gaaattcaga atatccagta ctcttacccc ngcaatgtct gtaatcactt tctctgtgat    60
c                                                                   61

<210> SEQ ID NO 47
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 47
tgatgacata tttgataaac ttaaagaggc ngttaaggaa gaaagtatta aacgacacaa    60
g                                                                   61

<210> SEQ ID NO 48
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 48
agtgtatcac cagagtcctg gacaggctcc ntacccggga ccccagcagc cttcataccc    60
c                                                                   61

<210> SEQ ID NO 49
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or a

<400> SEQUENCE: 49
cagcttgggc agtcaggttt ggggccttcc ngggtggccg gggagagggg gctgtgggga    60
a                                                                   61

<210> SEQ ID NO 50
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 50
ggcagcggaa gtgtgtctgc aggtggtcaa ngtcggccca actgagctcc cccacaggtc    60
g                                                                   61

-continued

```
<210> SEQ ID NO 51
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 51
cgttggcacg ctccagccgg gtgcggccct nccccagcgcg cccagcgggt gccagctccc      60
g                                                                      61

<210> SEQ ID NO 52
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 52
ggctacagga attctctgga atttttttact ntgcttgctc agagaagagg tatgcaccaa      60
a                                                                      61

<210> SEQ ID NO 53
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 53
ccccatggct cctggtaact acctgatcag ngtcaaatac ggtgggccca accacatcgt      60
g                                                                      61

<210> SEQ ID NO 54
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 54
tcacccaaaa agtaagttca cttacgccaa ntgtgaactt gaacttgaat gggggtccct      60
c                                                                      61

<210> SEQ ID NO 55
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 55
caattctgtg ttcaccctca ccctgcaggc nggcctctca gccatcaaga caccgtatcc      60
t                                                                      61
```

```
<210> SEQ ID NO 56
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or c

<400> SEQUENCE: 56
tgcaatggtt tcaaaatcat cttgatcccc naaaaaagag atattcaaag aaagatgctt    60
g                                                                  61

<210> SEQ ID NO 57
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 57
cttgaggaag cagtccttat acctcaagtt ngacccctc ctgagggaca gtcctggtag     60
a                                                                  61

<210> SEQ ID NO 58
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a, c, g or t

<400> SEQUENCE: 58
cttagcgcat tcattacaag ggaacaaggc nacatacata ctacagcctt tcacatcggt    60
c                                                                  61

<210> SEQ ID NO 59
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 59
agccgatcta ggaattgtac ttttgcttcc nggcttttcc gcctgtcttg acagttcttt    60
c                                                                  61

<210> SEQ ID NO 60
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 60
tagtgctatt cccacccgta ccatgcattt ngagaagcac tggagattac tggaaagtat    60
g                                                                  61
```

<210> SEQ ID NO 61
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 61
catacctggt ctcatccgaa ccctgcggat ntattttca cccaagaaat ttcggatttc    60
a                                                                  61

<210> SEQ ID NO 62
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 62
gagagactgt agcactttc tcagaactag ngagacgggc attgtggatc aggttatggt    60
a                                                                  61

<210> SEQ ID NO 63
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 63
gtcactgact ttgatgattg gctcattttt nctaagatcc catacagtgg cccggccact    60
g                                                                  61

<210> SEQ ID NO 64
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 64
tctcacctgc acagatgagg agagttcaca nttagccttt tcagcagctt cccgtaccct    60
c                                                                  61

<210> SEQ ID NO 65
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 65
ctacatctgt gtctctagtg cccccatcaa nagtcttctg ctggtggatg agaatgttct    60

```
<210> SEQ ID NO 66
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 66
gtcctcggag tggaagcggc acatgtcatg ntgggaggcc tggtatggct tgaagacctc    60
g                                                                    61

<210> SEQ ID NO 67
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 67
ctggatgaca tccaggctgg cagccccagc ncgccccaca ttgatggtca caggctttac    60
a                                                                    61

<210> SEQ ID NO 68
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 68
tccaccacca cctggctctc ctgtggggct nttccgaggt gtgtgtctcc gcctgctttg    60
g                                                                    61

<210> SEQ ID NO 69
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 69
aaagtttgac aggcagggac gggggcagat ngccttcgac gacttcatcc agggctgcat    60
c                                                                    61

<210> SEQ ID NO 70
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 70
aagctgggat ttggggtcat tccaatcctg nttcaaaatg aactcctgtg gaagtccccc    60
```

<210> SEQ ID NO 71
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 71
ataaagtgag gaaaacacgg agttgatgca naagccccaa catccaacct cgactcctct    60
t                                                                    61

<210> SEQ ID NO 72
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 72
tgcatagaca ctccccttca gtgggaaaac ncccctgaaga cagcagaggc aacctggata   60
t                                                                    61

<210> SEQ ID NO 73
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 73
tcgatgtagc aacagcttga agacaaaagg ngaagagatc tgtaagagaa ttaactagtt    60
a                                                                    61

<210> SEQ ID NO 74
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 74
cactttcacc attacaggcc atgctgagac naagcagctg acagaaatgc tacccagcat    60
c                                                                    61

<210> SEQ ID NO 75
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 75

```
agtaaatgtg agcgaattgg gccttgtgac ncaaggaggc aaagttattt ggggtaagtg    60
a                                                                   61
```

<210> SEQ ID NO 76
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 76

```
gcacgaaaac tgtttatgga atccagtcga ngttcaggca ccgcgcgatg aacgcaaaca    60
t                                                                   61
```

<210> SEQ ID NO 77
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 77

```
gatcacatta aagagctagt agatgactca ntaaataatg tcaggaagga cgatccaaca    60
c                                                                   61
```

<210> SEQ ID NO 78
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 78

```
aaagggaaa gcagatgctg gaaaggatgg naacaaccct gcaaaaaacc gagatgcctc    60
t                                                                   61
```

<210> SEQ ID NO 79
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 79

```
gcctcaggag cagggatggg ggtggtacac ngaggaaagc agtgagaagc acgcagggcc    60
g                                                                   61
```

<210> SEQ ID NO 80
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 80
tggtagctgg aaatagtcct aagaaacaag nttctagacc acctatccaa aatgcatgtg    60
t    61

<210> SEQ ID NO 81
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 81
gggttttatg accagcagcg agggtgctta ngcccacagc atgcacatcc gcatccacag    60
c    61

<210> SEQ ID NO 82
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or t

<400> SEQUENCE: 82
ctaaaacaag ctgtttttac cttcaggagc ntctgcatca catctctttg gcacagaaag    60
g    61

<210> SEQ ID NO 83
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or c

<400> SEQUENCE: 83
cagggagctg atggcagtac acttaaaaac nctcctcaaa gttcaaactt agatttcaga    60
t    61

<210> SEQ ID NO 84
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or c

<400> SEQUENCE: 84
gatgaaagga tgctgctgag gaattctgga ntccgtacta ggaaatttta agaaactttg    60
t    61

<210> SEQ ID NO 85
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

```
<400> SEQUENCE: 85
taagaagaga attcacatct ttctgttcta nctggtattc ctgcattatt ttctcagcag    60
t                                                                    61

<210> SEQ ID NO 86
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 86
tgcccctcct ggagaattta atgaggtttt naatggtgag tgtttgattt ataacactag    60
g                                                                    61

<210> SEQ ID NO 87
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 87
atctgctagc tacaagcccg tgtttgtgac ngagatcact gatgacctgc acttctacgt    60
g                                                                    61

<210> SEQ ID NO 88
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 88
gtctgtaagt tgtttgtgtg tcactgtgac ngctcccacg gttgtttcct ttggcaaacc    60
t                                                                    61

<210> SEQ ID NO 89
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 89
tgtagcagtt gcttcttcct gtttcaatgg nttgctatgt tcatatctaa gaaaaaattc    60
a                                                                    61

<210> SEQ ID NO 90
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a
```

<400> SEQUENCE: 90
gttctcctcc agctctagcc gcgtcttcac ntactgatca taattaccct gcatggaaat    60
g    61

<210> SEQ ID NO 91
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 91
tcttgatggt gctgtttgga cccgagttac ngagctggaa gcgctggctc acagtcatgt    60
c    61

<210> SEQ ID NO 92
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 92
catgtcctgc aggagggact ggggactctt ntccacgtgg tcgctgctct cggccagcgt    60
g    61

<210> SEQ ID NO 93
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 93
tgtgcagagg tggatgaggt cttgtgaaaa nctggctcct tttaacacgg ccctcaagct    60
c    61

<210> SEQ ID NO 94
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 94
cgttaagtgc tggatatact tggcttgcac nggacaccatt ttacggaggg attccggcaa    60
c    61

<210> SEQ ID NO 95
<211> LENGTH: 61
<212> TYPE: DNA
<213> ORGANISM: Homo sapiens
<220> FEATURE:
<221> NAME/KEY: misc_feature
<222> LOCATION: (31)..(31)

<223> OTHER INFORMATION: n is g or a

<400> SEQUENCE: 95
gatctcgtgg gcttcgctgt aggccttctc ngaggactcc accaccgtcg cccttttctc    60
t    61

<210> SEQ ID NO 96
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 96
cagtgcggtt ggtgagcagc tcctgcccac ngtcgagcac ctccagctgg agctggatca    60
g    61

<210> SEQ ID NO 97
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 97
caagatcaag gactgtcctt ggtatgaccg nggcttctgc aagcacggta ggtgccaggg    60
t    61

<210> SEQ ID NO 98
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 98
gacttgcatc tttacccact agacttctgc nctgacccag gggctggagc gaatcccaga    60
c    61

<210> SEQ ID NO 99
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or c

<400> SEQUENCE: 99
tgttgacata gttgaccagc tcatccgaca ngggatggaa agagggcctg ctccgggcat    60
t    61

<210> SEQ ID NO 100
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 100
tcttttggtg aggcacatgt atcgaattta nggattacag ttattgatgg aggacacatg    60
g                                                                    61

<210> SEQ ID NO 101
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 101
ctggatagag cgcacacagg cctccagctg ngccatgtcc gtctcatcat cccactgtgg    60
g                                                                    61

<210> SEQ ID NO 102
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 102
gcaggacacc accttgcggg cgcccacctc naaggccgag tgcaggacgt tgtcgttcat    60
g                                                                    61

<210> SEQ ID NO 103
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 103
atgcaaagaa cttccaggcc ctaaagaaag nagacggact gccaaagacc tttgggaagt    60
t                                                                    61

<210> SEQ ID NO 104
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 104
tgtgttgtag gagtgtgggg ctgattgtgc naagttccag aagagtgagc tagaattcaa    60
g                                                                    61

<210> SEQ ID NO 105
<211> LENGTH: 61
<212> TYPE: DNA
<213> ORGANISM: Homo sapiens
<220> FEATURE:

```
<221> NAME/KEY: misc_feature
<222> LOCATION: (31)..(31)
<223> OTHER INFORMATION: n is t or c

<400> SEQUENCE: 105
atctttctct tcccagcggc agagcataaa ntccttgttg ggcttatcac attgagctcc    60
a                                                                    61

<210> SEQ ID NO 106
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 106
accccagcga tggtcgtgcc agttttccgg nectttggaa gcttgtatcc cctctttgca    60
a                                                                    61

<210> SEQ ID NO 107
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 107
gatgccctgc cagagtagca ccttcccgtc ngtggccaca ctcagcacct ggaagcggtg    60
g                                                                    61

<210> SEQ ID NO 108
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or c

<400> SEQUENCE: 108
gtctgctgct tctgctgccc cctcctcctc naagcagccc gctgctgaca cagaggcatc    60
a                                                                    61

<210> SEQ ID NO 109
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 109
ccgcttcttg aggacaaagt catagttggc ngtagagttc atggcataga agacgttggc    60
g                                                                    61

<210> SEQ ID NO 110
<211> LENGTH: 61
<212> TYPE: DNA
<213> ORGANISM: Homo sapiens
```

```
<220> FEATURE:
<221> NAME/KEY: misc_feature
<222> LOCATION: (31)..(31)
<223> OTHER INFORMATION: n is a or g

<400> SEQUENCE: 110
ggcgttctgc ttcaccacgg tcaggctggc nccctggccg caccgcaggg cttcattctc    60
t                                                                   61

<210> SEQ ID NO 111
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 111
aaggtttgac tggaatgaaa actgggacga naggtaccta ttttaagata agtatgacac    60
t                                                                   61

<210> SEQ ID NO 112
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 112
agaattgaaa aaggcttata ggaaactggc nttgaagtac catcctgata agaacccaaa    60
t                                                                   61

<210> SEQ ID NO 113
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or a

<400> SEQUENCE: 113
tacctgagga tttactccag caagagcctg nagcatctgc tgaataaact gctgatgtcc    60
a                                                                   61

<210> SEQ ID NO 114
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 114
tctgcctgat gaagatctgg cttcctttca ntggagttta cttggtccag aacatccact    60
a                                                                   61

<210> SEQ ID NO 115
<211> LENGTH: 61
<212> TYPE: DNA
```

<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 115
agttggtggg gcaactcttc actgtgcttg nacctgggct ggggcaggat cctgaacctc    60
t                                                                   61

<210> SEQ ID NO 116
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 116
catcactgcc ctggcccacc tccgtgctgc ngtcctgtat gtgatggatt tgtctgagca    60
g                                                                   61

<210> SEQ ID NO 117
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 117
gaaacttaca agactccgct tccaagcttc ntgtatctta aaggagaaaa aagaatagct    60
t                                                                   61

<210> SEQ ID NO 118
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 118
ttcaaatggc tttgcatttg catgtttcag ngctagagcg taggaataga ccctggcgtc    60
c                                                                   61

<210> SEQ ID NO 119
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or a

<400> SEQUENCE: 119
aggaagagaa ttttcgctca agttgttgta ngtcaagtcc agaacctcaa gagctggcag    60
g                                                                   61

<210> SEQ ID NO 120
<211> LENGTH: 61

```
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 120
ctaccagctg atcaatctgt ccaattttta nttcagataa tccaaggtcc cttaagttaa    60
g                                                                   61

<210> SEQ ID NO 121
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 121
ttctcccatg gctcagaccc caccctgcca nctgcccaat atcccaggag tcactagccc    60
t                                                                   61

<210> SEQ ID NO 122
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 122
gaaccgctgg cggaacatga tccgcacttc ngcatggcca gcacgagtca gcacatcagt    60
g                                                                   61

<210> SEQ ID NO 123
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 123
gaacgagctg atatcgaatg gagaaggtga nggcactgcc caggatctgc aaggagaaat    60
g                                                                   61

<210> SEQ ID NO 124
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 124
tcatggagtc tccaagaact gctaaaggag naagggtaa aggagttctc tacgttccca     60
t                                                                   61

<210> SEQ ID NO 125
```

```
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 125
tttctgttga tgttcaaatt cttccttctc ngcagtctga ggaagagaaa aaggaattac    60
t                                                                    61

<210> SEQ ID NO 126
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 126
aatatctccc tggacggggc gtttctactc nctgctggat ccctcttatg ctaagaacaa    60
c                                                                    61

<210> SEQ ID NO 127
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 127
ttcgtggtct tcaaaccgca ccccaagctc nggcaggatg ttgtcccgca gggcatcgct    60
g                                                                    61

<210> SEQ ID NO 128
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 128
tttgaagact gggatgtatt atttaaggac nagaccagcg gctaatccaa tccagttcac    60
t                                                                    61

<210> SEQ ID NO 129
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 129
gcctcactag actcgaggcc tgagctccgg ntctccactt ccctccggtt tgtggctctg    60
a                                                                    61
```

```
<210> SEQ ID NO 130
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or t

<400> SEQUENCE: 130
ggagtcagcc gcctacctgg ccctcttgac ncggggcctg cagagactct accaggtgag    60
c                                                                   61

<210> SEQ ID NO 131
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 131
tcatcctact ctcatcacac actggatgcc ntatggatcc ctctacaatg tactacatga    60
a                                                                   61

<210> SEQ ID NO 132
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c, a or t

<400> SEQUENCE: 132
tctcaccttc ctcctcctcc agccgccctt naccgcagag aaccggaaga aaaccatgga    60
t                                                                   61

<210> SEQ ID NO 133
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 133
tcccaatgct attgccaggc aagtaaacac ngaagctgtg aaaagaagaa actgtgttat    60
a                                                                   61

<210> SEQ ID NO 134
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 134
taaatgttgt gtttaggtgg aagaagagcc ngaagaagaa cctgaagaga cagcagaaga    60
c                                                                   61
```

<210> SEQ ID NO 135
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or t

<400> SEQUENCE: 135
ccctcagact cggccgatgg gtcatttttc ntgtatattt tctcttgatt cccctccttc    60
a                                                                    61

<210> SEQ ID NO 136
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 136
ccagttggga tggacaaaac ccaccaagat ncagattgaa gctattcctt tggccttaca    60
a                                                                    61

<210> SEQ ID NO 137
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 137
atctgccacc gtggcaaggt acaagccttc nggagagaag cacacagatc tcagtgagct    60
a                                                                    61

<210> SEQ ID NO 138
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 138
ccagttggga tggacaaaac ccaccaagat ncagattgaa gctattcctt tggccttaca    60
a                                                                    61

<210> SEQ ID NO 139
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 139
ggtcaggcaa ggggtcagag gcaccctggg nggtttgtac tgggctgaaa tccagtcccc    60
c                                                                    61

<210> SEQ ID NO 140
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g, a, c or t

<400> SEQUENCE: 140
tccacctgat atccagaccc cagagtcatc ntctgtgaag gaagaactca ttccccaaga    60
t                                                                   61

<210> SEQ ID NO 141
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 141
ctgtagccca atgggaattg cctgacgctg nataggtgtt ggttcctgca gtgacccaa     60
g                                                                   61

<210> SEQ ID NO 142
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 142
gagagattgg gtttttacct ccagcaagaa ntctgagaca tcatgtagac acatgatcag    60
a                                                                   61

<210> SEQ ID NO 143
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 143
taacatggct ctctctgtct tacagggcaa ngcaatctat aatctccttc cagatatcat    60
c                                                                   61

<210> SEQ ID NO 144
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 144
cttcaacagc gacacccact cctccacctt ngacgctggg gctggcattg ccctcaacga    60

-continued

```
c                                                             61

<210> SEQ ID NO 145
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 145
gcgatctgcc atgagagcag tagcagcact nctaaccatt ccagaagcag agaagagtcc    60
a                                                             61

<210> SEQ ID NO 146
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 146
gatggcatca accaccctgg gtgtgtcaaa ntcatctgcc aaggccgcct tcacggccct    60
c                                                             61

<210> SEQ ID NO 147
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 147
taaaagatta tttgaaaaat acttgaagga ngaaagtggc ttcaaagatc cttccagcga    60
c                                                             61

<210> SEQ ID NO 148
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 148
actatagtta aagccacctg gaaatagaag ngtcatccat tttcatcagt gatttgaaca    60
c                                                             61

<210> SEQ ID NO 149
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 149
gaagagccag gcccagaaag aagaaaaccc naagaaacac agaagccatc cttacaagca    60
``` c                                                                             61

<210> SEQ ID NO 150
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 150
ggatgaggac gacctggcct acgcagagac ngagaagaag acgaggacag actccacgtc      60
c                                                                             61

<210> SEQ ID NO 151
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 151
cctggaccac gtgtgggatg aaggctgtgc ngtcgttcac ctgccagagt ccccaaagcc      60
t                                                                             61

<210> SEQ ID NO 152
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or t

<400> SEQUENCE: 152
ggcaggtcag gctgacctgg ttcttggtca nctcatcccg ggatgggggc agggtgtaca      60
c                                                                             61

<210> SEQ ID NO 153
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or c

<400> SEQUENCE: 153
ggtcaggctg acctggttct tggtcagctc ntcccgggat ggggcaggg tgtacacctg      60 t                                                                             61

<210> SEQ ID NO 154
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or a

<400> SEQUENCE: 154

```
aggacgctga ccacacggaa cgtgctgttg nactgctcct cccgcggctt tgtcttggca    60
t                                                                    61

<210> SEQ ID NO 155
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 155
aagcaacaca accactactt acccccagag ntttagacat tctctcccca actccatggc    60
c                                                                    61

<210> SEQ ID NO 156
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 156
ccagagactt acctcctgga aaagattctg nctgaagacc tccacctaca cagagagcag    60
t                                                                    61

<210> SEQ ID NO 157
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g, a or t

<400> SEQUENCE: 157
ggcagccagt gcaggtggca gggttcggag ncgattgtgt gacaagtcaa gatgggtgac    60
c                                                                    61

<210> SEQ ID NO 158
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or ctaaa

<400> SEQUENCE: 158
tagcctgggt gacagagtga gaccttgtct ntaaataaat aaataaataa atagaaaagt    60
a                                                                    61

<210> SEQ ID NO 159
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 159
``` ttagttttt tttttcttt gattttagac ntgccataac tactttattg aagaccttgg    60
a    61

<210> SEQ ID NO 160
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 160
cacatggcaa ttcctccatc attgcagacc ngatcgcact caagcttgtt ggcccagaag    60
g    61

<210> SEQ ID NO 161
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 161
tcagatgcca ccggtgccct cgccctcaca ncctccttct ggcaaacctg gtaggcttcc    60
a    61

<210> SEQ ID NO 162
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 162
tagttttgtt cttttgtct ctcttcttca nccatccat gttagctcta aggaggtttg    60
a    61

<210> SEQ ID NO 163
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 163
tgcgggcctc atgctcgtcg agttcttcgc ncctggtga gtccattctg ccgaggcggg    60
g    61

<210> SEQ ID NO 164
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 164
gtcaatcttt catcgtcatt gctgaatggc nctctattat gtgaataatc cataattatt    60
t                                                                    61

<210> SEQ ID NO 165
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 165
gcccttggat tgtctcagga tgttgcaggc ncaactttca tggcagcggg cagttcagct    60
c                                                                    61

<210> SEQ ID NO 166
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 166
tgaatgaatc agtttttataa ctggggactt ntgtttttaa taatatttg ttattaacaa    60 t                                                                    61

<210> SEQ ID NO 167
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 167
ttttaaaaga agtaaaacat ttattaggta ntaagttttt cccatcactg atgtctccta    60
a                                                                    61

<210> SEQ ID NO 168
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 168
ccagaatgtt acctggcaat ttgattcctg ntcccaccat ccttctgcac tagtcacatt    60
g                                                                    61

<210> SEQ ID NO 169
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 169
tagtgatgca atcggccact ctctcccttg nctcctgtgt gtccaacagt gcctaaacca    60
a                                                                    61

<210> SEQ ID NO 170
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 170
cagcatcctc ctgatggtac aggggacagt natagccagc acacccacaa cccagacacc    60
a                                                                    61

<210> SEQ ID NO 171
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 171
ggtgtggaag cggacatagg ggcagccaac ntccagcaca acctcctggc taagccgact    60
g                                                                    61

<210> SEQ ID NO 172
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or t

<400> SEQUENCE: 172
gcgtacgtgc ccttgctcca caaaggccac ngcagcctga aggtgctgcg ccatgcgcag    60
c                                                                    61

<210> SEQ ID NO 173
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or a

<400> SEQUENCE: 173
atgcatcatg atttcttgta gcttcttcac nactagagcc tcacacccct gtaacaaaca    60
c                                                                    61

<210> SEQ ID NO 174
<211> LENGTH: 61
<212> TYPE: DNA
<213> ORGANISM: Homo sapiens
<220> FEATURE:
<221> NAME/KEY: misc_feature
<222> LOCATION: (31)..(31)

<223> OTHER INFORMATION: n is t or c

<400> SEQUENCE: 174
catcctagac atggttcttc gagaggatgg ngaagatgaa aatgaagagg tcagtgctgg    60
c                                                                    61

<210> SEQ ID NO 175
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 175
gcgcaaatct ttttctagtt gcaagatggt ngtctctcct tcttcctgaa taagacaacg    60
t                                                                    61

<210> SEQ ID NO 176
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 176
acctcaacag gtttggaagg gtgatgggga ngtcttcggg gtatttcaca cttaggtcct    60
t                                                                    61

<210> SEQ ID NO 177
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 177
cattgaagac ttagaaaagg tggagcgcct ntccagtggg ccggagcaga tcaccctcga    60
g                                                                    61

<210> SEQ ID NO 178
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 178
ggggcactcc gagcaggggc cgggccctcc ntgtgtccat taacgacgac ggcaactggc    60
c                                                                    61

<210> SEQ ID NO 179
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 179
agaggcggct gccgccgaca ccatcaccat ngccaccccc gagagcctga cagagcaggt    60
g                                                                   61

<210> SEQ ID NO 180
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 180
cgcgtcgggg tacgtctccc ggatgtattg ntccatctcc aggatggccc ggccgtgcag    60
g                                                                   61

<210> SEQ ID NO 181
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 181
ggtggtcacc gtggtaaggt aggcaatgag ngacctcagc tccttgtcaa actgcagacc    60
a                                                                   61

<210> SEQ ID NO 182
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 182
tgccaattat atctctggga tccagactat nggacatagg gtaattgtat ctgatgtcca    60
a                                                                   61

<210> SEQ ID NO 183
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or g

<400> SEQUENCE: 183
gcaggtccct ccccgcgcgg aggagatcac natccccgcg gacgtcaccc cggagaaggt    60
g                                                                   61

<210> SEQ ID NO 184
<211> LENGTH: 61
<212> TYPE: DNA
<213> ORGANISM: Homo sapiens
<220> FEATURE:

```
<221> NAME/KEY: misc_feature
<222> LOCATION: (31)..(31)
<223> OTHER INFORMATION: n is g or c

<400> SEQUENCE: 184
ggtaactgcg ctcgaccggg tgagagaaga nctcatagag cgccatgagc accgctcgca    60
g                                                                   61

<210> SEQ ID NO 185
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or t

<400> SEQUENCE: 185
gctgctccgt tggtgacctc cctggctgca ntcccaggct caagcctcat cttttggtt    60 a                                                                   61

<210> SEQ ID NO 186
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 186
catgctccct gctcttggtc ctgttttcta ngtactgaaa aataaaagaa ggggggggaga    60 a                                                                   61

<210> SEQ ID NO 187
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 187
cactcccagg ctgtaacctg tatgggggat nggggtaaga gaggggaggg agctttacct    60
t                                                                   61

<210> SEQ ID NO 188
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 188
cacccagccc ttctccagca ccttggcaaa natgtccgtc agcacctctt tgatgggccg    60
c                                                                   61

<210> SEQ ID NO 189
<211> LENGTH: 61
<212> TYPE: DNA
<213> ORGANISM: Homo sapiens
```

```
<220> FEATURE:
<221> NAME/KEY: misc_feature
<222> LOCATION: (31)..(31)
<223> OTHER INFORMATION: n is a or g

<400> SEQUENCE: 189
ggaactatga gcagattgtg aaggcacacc nggacaaccc ccatgaaggg gaggaccagg    60
t                                                                   61

<210> SEQ ID NO 190
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or a

<400> SEQUENCE: 190
aggtacaatc caaatcctc gaattggagc nggctgcctg gaaaaacaca gtcatagtta    60
a                                                                   61

<210> SEQ ID NO 191
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 191
gcgcacgatg ctggagttgc tcaaccagct ngacggcttt gaggccacca agaacatcaa    60
g                                                                   61

<210> SEQ ID NO 192
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t, a, c or g

<400> SEQUENCE: 192
agtcaggctc tgctggtatg cagctgatgt nagggtggtc aggtcactgg agtgaaagga    60
a                                                                   61

<210> SEQ ID NO 193
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 193
caagatcaac aggttaggag agttgatcct nacctctgag agcagccgct atcagttccg    60
g                                                                   61

<210> SEQ ID NO 194
<211> LENGTH: 61
<212> TYPE: DNA
```

<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 194
gattacctcc aatttttcag ccaagagacc ntcagtgccc ccagacctca atctcatctg    60
c                                                                   61

<210> SEQ ID NO 195
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or t

<400> SEQUENCE: 195
gaagctggag agcaggtgca ggaggctcct ngcgttcaca taattgtcat catccacgtg    60
g                                                                   61

<210> SEQ ID NO 196
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 196
gcgcggctcc tactgggagt gctcacccag natgtgtgcc acggcctcca ccaggtcccg    60
c                                                                   61

<210> SEQ ID NO 197
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 197
gatctgcctg tcgaaacgcc ccggcctaag nagcgcgggg tccaggatat ctggtcgatt    60
g                                                                   61

<210> SEQ ID NO 198
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 198
tctgtattag gtggttgtct ggggtgagtg ngactccact gatgactgta ttgagcacaa    60
c                                                                   61

<210> SEQ ID NO 199
<211> LENGTH: 61

<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or c

<400> SEQUENCE: 199
agtctgtgtg ggatcgatca tgaggcgctc nacaagcaga ttatggagta caaaaggagg    60
a                                                                   61

<210> SEQ ID NO 200
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 200
atcctcgcgg cggtggaagc tgatgaaggc naagccctgt ggaggggcgg gatggggtcg    60
g                                                                   61

<210> SEQ ID NO 201
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 201
gaaggtgtct gagaagtact ggaacagggc nttctgcttg tgcacctcca gccccaggat    60
g                                                                   61

<210> SEQ ID NO 202
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 202
atctttcccc aggtcgtgtt atcgctccca ngaaggcgcg cgtcgtgcag cagcaaaagc    60
t                                                                   61

<210> SEQ ID NO 203
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 203
gaagccaccg ccacagcgtg tgaccctcac nctacctgtc ctgaatgcag cacgaactgt    60
c                                                                   61

<210> SEQ ID NO 204

```
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 204
gtccctctcc acgtctctct ctgggcttga nagctgtggg aaccaatgtg agtcaggacg    60
c                                                                   61

<210> SEQ ID NO 205
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 205
gaagcattac ttgagcagtg cgaggaaggc ngcgggttcc acgtcgggca gctcaatctc    60
c                                                                   61

<210> SEQ ID NO 206
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or c

<400> SEQUENCE: 206
gtatgtctcg ttgtcggggt ccagctccag ngccttcttg tagtaagcca cggcctccac    60
g                                                                   61

<210> SEQ ID NO 207
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 207
gtgccagaga aagacagccc cgtataagaa ngtcaatgtg cagaacttcc acatcaggta    60
a                                                                   61

<210> SEQ ID NO 208
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or g

<400> SEQUENCE: 208
ggggcttcac cgagggctac tccggaagcc ncctcttgtg cagaggagcc agtgaggcga    60
a                                                                   61
```

<210> SEQ ID NO 209
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 209
gcgtccgaag acctgcacag actgcagcgg ncccttggac ggcatggctc cgagcgtgga    60
c                                                                   61

<210> SEQ ID NO 210
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or c

<400> SEQUENCE: 210
ctctccaagg tcaaagggct cccggggctt nggcttatac tcccgcttag ggcgtgagga    60
a                                                                   61

<210> SEQ ID NO 211
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 211
ggactgcttc tgctccagcc gggctagggc ngcagcggct gccatctgtg cctcattggt    60
g                                                                   61

<210> SEQ ID NO 212
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 212
cagcctgccg ctccgcgtct ccttctgccc nctctcgctt tggcgctggc agctctatgc    60
t                                                                   61

<210> SEQ ID NO 213
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 213
atcgacaagg cgacgggcaa gatctccaag ntgggccgct ccttcacacg cgcccgcgac    60
t                                                                   61

<210> SEQ ID NO 214
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 214
ttgagagcca ggcccaggtc tcacggtggc ntatggacag ctcctcccca taggcctggt    60
c                                                                    61

<210> SEQ ID NO 215
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 215
cctcctgtca gggcctccca gagtgaaggc ngtgaagtcg tcagaacaca tcaacgaggg    60
g                                                                    61

<210> SEQ ID NO 216
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 216
catcgtgtca cagaaacaga tcgcagaccg ngctgcccac gacgagtccc cggggaacaa    60
c                                                                    61

<210> SEQ ID NO 217
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 217
ggcctgggaa atcacgaaga agacctgtgc ntacaccaac cacactgtgc tgcctgaggc    60
c                                                                    61

<210> SEQ ID NO 218
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 218
gcctgttccc ctgtccttcc ctttaggaga ngagtgaaaa acccaaaaag aagaaaaagc    60
a                                                                    61

```
<210> SEQ ID NO 219
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 219 tcttttctt tccttcccca caccccaggg ntaccaagaa aagaacaaat tcattgctgc    60
a                                                                  61

<210> SEQ ID NO 220
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 220
gcgaaagaac cctggtgtgg gcaacggaga ngacgaggca gctgagttga tgcagcaggt    60
g                                                                  61

<210> SEQ ID NO 221
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or a

<400> SEQUENCE: 221
tctgtttccc tgataagtgc cggagtacca nggggagccg gatgagattt ccatacagaa    60
a                                                                  61

<210> SEQ ID NO 222
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 222
tcttctaaag agcatagctc aaaaattgta nacacttctt ccgttaattc ctgtggacca    60
g                                                                  61

<210> SEQ ID NO 223
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a , c, t or g

<400> SEQUENCE: 223
gaaagccaaa ctcgctgagc aggctgagcg ntatgatgat atggctgcag ccatgaaggc    60
```

```
a                                                                 61

<210> SEQ ID NO 224
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or t

<400> SEQUENCE: 224
caatatcact gtcttccacc tccacgtttc nttccactgg aaggttttca gggcagtaac   60
a                                                                 61

<210> SEQ ID NO 225
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or t

<400> SEQUENCE: 225
aaaaaagccg ttcaatagta ttattgagca nctgtcagtg gtattcccat gttacaacag   60
g                                                                 61

<210> SEQ ID NO 226
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 226
gtggtctccc ggctgggctg ggctgcggag ngtgcacctc acaggaagcg tcgggactga   60
t                                                                 61

<210> SEQ ID NO 227
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 227
cgcccttgca gaaactttat tggggtcagc ntgcagcatc cttccgtact cctcgcagtg   60
c                                                                 61

<210> SEQ ID NO 228
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 228
ctctttaaag accagctggt gtatcctctt ntggctttta cccgacaagg taagagatga   60
``` a                                                               61

<210> SEQ ID NO 229
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 229
cattgccctc acgatgtacc ccatgcgtat ngatgagagc attcacctcc agctgcggga      60
g                                                               61

<210> SEQ ID NO 230
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t, a or c

<400> SEQUENCE: 230
gcgggcagag aggcggacca cggcgaagcc ntgtggcccc tggaaggccc agcagttgcc      60
t                                                               61

<210> SEQ ID NO 231
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is g or c

<400> SEQUENCE: 231
ctttgtaggg agattttgca gctgctgccg ncaacctaca aacctgcctg gcagttttgg      60
g                                                               61

<210> SEQ ID NO 232
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or t

<400> SEQUENCE: 232
ccggcttctc ctgcaactct acagactgga ngaggccaca ggtggacagg aggcgggaca      60
g                                                               61

<210> SEQ ID NO 233
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is t or c

<400> SEQUENCE: 233

```
gtggccagta tcatcagctc cttcttacag ngcacacaca tgctcccagc ccagctgtag    60
c                                                                   61
```

<210> SEQ ID NO 234
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 234

```
ctgcgccatg tcggggcgt tgggcagcac nctggacagg ctgtagttcc ctgcacacac     60
a                                                                   61
```

<210> SEQ ID NO 235
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 235

```
ccatgtcctg gtatgttcct ggcatacatg ncacacactg gccgagctca ccaccgaagt    60
g                                                                   61
```

<210> SEQ ID NO 236
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a or g

<400> SEQUENCE: 236

```
gctcacgtca aagaaggcct tctcgtccac ngtcttaggg gcacccatag tgggcgtgcc    60
a                                                                   61
```

<210> SEQ ID NO 237
<211> LENGTH: 61
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is c or a

<400> SEQUENCE: 237

```
tgaggatctc agggaactga tctgagtact ntctgagaaa ctccagcatc tcggactgct    60
g                                                                   61
```

<210> SEQ ID NO 238
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 238

```
ggattacact cctgagtgat atcgttcagg ntgacatggg catcctgcat ctcctccctc    60
t                                                                    61
```

<210> SEQ ID NO 239
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 239

```
cccggcccac cggccctccc gcctcccgtc nggcctctaa aagtcacagc tcagttaaga    60
g                                                                    61
```

<210> SEQ ID NO 240
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 240

```
atatcgaaga ctggtatgga gaaaggcacc ngggaccact ttttggcctg gatcttccct    60
c                                                                    61
```

<210> SEQ ID NO 241
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 241

```
tacaccagca tagtggaaag tgttcagggt natctgagtg gcaggttctc caagagactg    60
a                                                                    61
```

<210> SEQ ID NO 242
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 242

```
tggagaagcc gaactatata gtgcctgact ncatgccagt tgtgtatgat aaactgccgc    60
a                                                                    61
```

<210> SEQ ID NO 243
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c -continued

<400> SEQUENCE: 243
cgtgggaaca gcagagggtg gttaatgatg nctgtcacca cgaccagaca gacccggaag    60
a                                                                    61

<210> SEQ ID NO 244
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 244
ctggcagatt atggtggata tgaaggaggc natgtacaag actatgaaga cttcatgtga    60
c                                                                    61

<210> SEQ ID NO 245
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 245
agctgcagga ccaagacagc atcctcttca nctccacact gcacggcggc tgaggcctcc    60
c                                                                    61

<210> SEQ ID NO 246
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 246
cggtcacgct ctcggtcacg gtcgcggtcc ngatcccggt gtctctctcg ttctctgctt    60
c                                                                    61

<210> SEQ ID NO 247
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 247
ttctaagcgg cctggatttt cttcatgcaa nctgcattgt tcaccgggac ctgaagccag    60
a                                                                    61

<210> SEQ ID NO 248
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 248
actgcctcca gtgtcttcaa tcttgcctttt ntccacgtcc atcctgcagg tggacatagc    60
a                                                                    61

<210> SEQ ID NO 249
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 249
accaccatcc actacaagta catgtgtaat ngctcctgca tgggggggcat gaaccgccga    60 c                                                                    61

<210> SEQ ID NO 250
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 250
agtacatgtg taatagctcc tgcatggggg ncatgaaccg ccgacctatc cttaccatca    60
t                                                                    61

<210> SEQ ID NO 251
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 251
gactctcatc gttttcttga aaggaacttg ncgcaaaagg cagcagagag gtctcggtac    60
g                                                                    61

<210> SEQ ID NO 252
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 252
gaaggccaac aacaaccaga agcccaagac nagcaaggaa catatacata aaaattctgg    60
c                                                                    61

<210> SEQ ID NO 253
<211> LENGTH: 61
<212> TYPE: DNA
<213> ORGANISM: Mus musculus
<220> FEATURE:
<221> NAME/KEY: misc_feature
<222> LOCATION: (31)..(31)

<223> OTHER INFORMATION: n is a or g

<400> SEQUENCE: 253

```
cgcatctgcc ctcaggaata tacctgctgc nccacagaaa tggaagacaa gctgagtcaa    60
c                                                                    61
```

<210> SEQ ID NO 254
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 254

```
aagcgcgacg ccagttctcg ggtgccggcc ngcggggacg cgcggcccgg ggttcgggac    60
g                                                                    61
```

<210> SEQ ID NO 255
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 255

```
tttactacct ggtgaccttc tgggaggagg ntcggattca atctgaactt aaactttcaa    60
c                                                                    61
```

<210> SEQ ID NO 256
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 256

```
ggttctggag ggcacgcagc tttgaggatg natcagggcc agctgtgatc acctcatgaa    60
a                                                                    61
```

<210> SEQ ID NO 257
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 257

```
gttacctcca gcgtttggat gtgctcaaac ntgtctgcat cccactgctt gatcttgtgg    60
t                                                                    61
```

<210> SEQ ID NO 258
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 258
gtttccactt ttcctgatta tcatgggaaa ncgatcatct aatgaagtgt taaatgtgat    60
a    61

<210> SEQ ID NO 259
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 259
atcatcagct gtgtcacaca cctcatattg nctcgagtgt gattgattca gatgaaaagt    60
g    61

<210> SEQ ID NO 260
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 260
cttcctactt agcctctacg cccaccgcta ncgggctgac tttgcggaca tcagcatcct    60
t    61

<210> SEQ ID NO 261
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 261
ggtaaggtta tctgatttaa tggaagaaac ntgaagctgt atgagggcca ggcggaaagc    60
t    61

<210> SEQ ID NO 262
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 262
gcaattcact gtaaagctgg aaagggacgg nctggtgtaa tgatttgtgc atatttattg    60
c    61

<210> SEQ ID NO 263
<211> LENGTH: 61
<212> TYPE: DNA
<213> ORGANISM: Mus musculus
<220> FEATURE:

<221> NAME/KEY: misc_feature
<222> LOCATION: (31)..(31)
<223> OTHER INFORMATION: n is g or c

<400> SEQUENCE: 263
gcgccaggtc tcctgcgtcc agacagtcgg ncaggctcgg ctgggcgttg cccacacgat    60
a                                                                   61

<210> SEQ ID NO 264
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 264
agcaagatct ggacgatgaa gaaaaaactg ncaagttcat tgaggagcag gtgagaagag    60
g                                                                   61

<210> SEQ ID NO 265
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 265
ccttctgctt ctctgtccag gcggacagct nctcaaatcg ccctttcata gcttgattat    60
t                                                                   61

<210> SEQ ID NO 266
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 266
caagccaaga atcacagtcg ggaactgtat ntgatgctga gttgtcctgc tcaggcattt    60
c                                                                   61

<210> SEQ ID NO 267
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 267
ccctgattgt tgtccacaca gtatgtactc nggatgtctt ccaactgccg gctcagctcc    60
t                                                                   61

<210> SEQ ID NO 268
<211> LENGTH: 61
<212> TYPE: DNA
<213> ORGANISM: Mus musculus

```
<220> FEATURE:
<221> NAME/KEY: misc_feature
<222> LOCATION: (31)..(31)
<223> OTHER INFORMATION: n is a or c

<400> SEQUENCE: 268
tcggagctgg cggctccagt agctgctcga ngtccaagtc ttgggcacgt ggcccagtcc      60
g                                                                      61

<210> SEQ ID NO 269
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 269
ggggccacca acttcctgtt ccagttgagc nctgggctgc agctggaagc cgtggtgtcc      60
a                                                                      61

<210> SEQ ID NO 270
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or t

<400> SEQUENCE: 270
cgggacaaaa tgaactcccc ggggctccag ngcaaggagc ctggcagcag cttgcacctg      60
g                                                                      61

<210> SEQ ID NO 271
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 271
gctcagtgag ctcatcctgt tggctgcact naggtgcagg gggtggctct gccctgggga      60
g                                                                      61

<210> SEQ ID NO 272
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 272
cctgtggggg tttctgttga cttttcacaa ngtcagcacc gcacaggtga ttgagccgcc      60
c                                                                      61

<210> SEQ ID NO 273
<211> LENGTH: 61
<212> TYPE: DNA
```

<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 273
cactggtaag gcttctcccc aagatggatt ntctgatgtc tgatgaggtg tgaacttctc    60
t                                                                  61

<210> SEQ ID NO 274
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 274
agtaccagaa gcattgcaga actggtgagt nacgttgtag agtctgcagc aggacgactg    60
t                                                                  61

<210> SEQ ID NO 275
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 275
acttacccca tccaggaacg aattcttgct nttggtgaat actctcttgc tttacctcca    60
a                                                                  61

<210> SEQ ID NO 276
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or a

<400> SEQUENCE: 276
gcagcttgat gaatgtgctt ctgctattac naaggcccaa gtagcaatca agactgctga    60
c                                                                  61

<210> SEQ ID NO 277
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 277
ccgccaacct cgaagcctta cctctttggg ntctccagat ccagtgagca tctttcgttc    60
g                                                                  61

<210> SEQ ID NO 278
<211> LENGTH: 61

<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 278
gtcacagaag ggctgtccaa ctcaatcaca ntccggagtc tccctaactc cctgccagaa    60
a                                                                    61

<210> SEQ ID NO 279
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 279
acctccgttc tctctcctct cttccagtac nctcctcccc tcaataagct attctgccag    60
c                                                                    61

<210> SEQ ID NO 280
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 280
cctcccctca ataagctatt ctgccagctg ncgaagacgt gccctgtgca gttgtgggtc    60
a                                                                    61

<210> SEQ ID NO 281
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 281
tctgaatggc ctctatgctt tccacatcac ncttcaaggc caacgcctgg atgaggcggg    60
t                                                                    61

<210> SEQ ID NO 282
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 282
agcgatgacg acgacgatga tgacgatgac nacaccgagc agagtgaaga ggggccggag    60
t                                                                    61

<210> SEQ ID NO 283

-continued

```
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 283
ggaactcctt caggtagctg cggtgtttgc ncttggccca gatagtcatc tgggtgaagc    60
c                                                                   61

<210> SEQ ID NO 284
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 284
ctaagctctg tggggctcaa atctccatag nccccactga aaatggggat agcgatgacg    60
a                                                                   61

<210> SEQ ID NO 285
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 285
ttctgtccag gccatctaaa attttcatgt natctgaagc caattggaaa tcaaagacct    60
g                                                                   61

<210> SEQ ID NO 286
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 286
tacacaacat cgatcaggac tttttgatg ncttgccatg tgagtaccca gccattgccg    60
c                                                                   61

<210> SEQ ID NO 287
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 287
gtcaatgatt tgtagagaag gccgttcagg ncctcaggc ggatgctgtc ttccttccta    60
g                                                                   61
```

```
<210> SEQ ID NO 288
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 288
aaaaatgcat cgaggaaata tacacagctg naaaaatttt gtgatggtct catttttggt    60
a                                                                   61

<210> SEQ ID NO 289
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 289
tgagcgaggc ggccaagagc tccggggccg ncggctctct gccctccacg ccgccgccgc    60
c                                                                   61

<210> SEQ ID NO 290
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 290
gagatctcct cgctccggcc ctgcttgctg ncctttgggg cagagggctc ctctatccgg    60
g                                                                   61

<210> SEQ ID NO 291
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 291
tctactggaa cctgttttcc caatagcatg ncatcggctc tgtgaggggc cggatttctc    60
a                                                                   61

<210> SEQ ID NO 292
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 292
gaaaaaccgt tcttataagt tgttggaaga nagcgagagc ggcgaggagg cagtgggtag    60
t                                                                   61
```

<210> SEQ ID NO 293
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 293
gtgagcacaa cttgagcaag ccagaattta ntccaacatc tatcaaattc aaaatccagt    60
t                                                                   61

<210> SEQ ID NO 294
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 294
ggcaggagta aggcctgaac tcacacagct nctcgtgctc tgcctttttg gtgtgtggca    60
g                                                                   61

<210> SEQ ID NO 295
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 295
gcgtcaggag gttgtagatg taaagaccat natgaacaca tggacactgc agaagggctt    60
t                                                                   61

<210> SEQ ID NO 296
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 296
gaacgcgacc ctgatgagtt aagatttaat ncaattgctc tctcagcggc atagcatctt    60
g                                                                   61

<210> SEQ ID NO 297
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 297
acagctgcct atgtcaatgc tatcgagaaa ntcttcaagg tgtacaatga agctggtgtg    60
a                                                                   61

<210> SEQ ID NO 298
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 298
tccttagtga acaacagaac gcaagccaag ntagcagagg aactgggcat gcaggagtat    60
g                                                                   61

<210> SEQ ID NO 299
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 299
ggctccttgg ccttgatgat ttggctgatg ncaacacctc acagccatga gaccgagcaa    60
a                                                                   61

<210> SEQ ID NO 300
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 300
tccatcctgt ttcagaacct tcattgacag ntcgagaatc agtctgagga aatcccatgt    60
g                                                                   61

<210> SEQ ID NO 301
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 301
aggagtattc ttgtccatcc catggaaaag nttgctgagc ctggttaaca aacaaccaaa    60
g                                                                   61

<210> SEQ ID NO 302
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 302
agcgatccac ataaggcatt gcgaagaacc ncctcctgtt gtatcttta tttaggtacc    60

-continued

| a | 61 |

<210> SEQ ID NO 303
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 303
ccctcaagtt cctgtgcaga gatctgtggg ncgccatgtt ccagaagcac atggacggac    60
t    61

<210> SEQ ID NO 304
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 304
gcccatcata gcgtatctca tctcaaaggg ncaggtatgt gttgtcatgc accttatatt    60
c    61

<210> SEQ ID NO 305
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 305
agtggtggac agggttatgg aaaccagggc ngtggctatg gcgggagtgg cagctatgac    60
a    61

<210> SEQ ID NO 306
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 306
accccttctt actatacaac ttcagatgcc ntcatttcta cagagactgt attcatcgtg    60
g    61

<210> SEQ ID NO 307
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 307
atggctttga agatgttgcg actgagttag ngaagagtaa acatgctctt atttgggctc    60

```
a                                                             61

<210> SEQ ID NO 308
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 308
catactgatg aggcaagctc tgaagtcctg naccccaact atcagagctg ctgggtcctg    60
a                                                             61

<210> SEQ ID NO 309
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 309
agcaaagcag attatgagct gtacaacaaa ncatctaatc ctgataaggt ggttgggaca    60
c                                                             61

<210> SEQ ID NO 310
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 310
gctgctctcc aggggtccca gagcctctac ntgagccaca gcagtaacac ccgtaggttc    60
a                                                             61

<210> SEQ ID NO 311
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 311
ttactggtca atgaagtcca cacccacacc naaagcttct gccatatagc cgagggttaa    60
t                                                             61

<210> SEQ ID NO 312
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 312
```

```
gaaaccgtca ttgtcgggct tcggggcgac nctaggcttg ccactgagca tgttaaaggc    60
g                                                                    61
```

<210> SEQ ID NO 313
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 313

```
agataaagaa agacatacat ttcttgcaaa ncacatcctt cttcagcagg aggatcccaa    60
a                                                                    61
```

<210> SEQ ID NO 314
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 314

```
gaaaaaattg catacaaaaa agaagactgt ngatgggaac ggtggagaaa gcctacatat    60
t                                                                    61
```

<210> SEQ ID NO 315
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 315

```
tctgattttc agggaaaaca tgagaatcac ncagttactc ctcgatttcc aaaattaaaa    60
g                                                                    61
```

<210> SEQ ID NO 316
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 316

```
actgactaag cctttactta ccagatgggt ntgggaacac ctgatcaatg gtaagctggc    60
c                                                                    61
```

<210> SEQ ID NO 317
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 317
ttcaagacaa taactgggac tacaccagat ntgctcaggc cttcactctt ctcaaggtaa    60
a                                                                    61

<210> SEQ ID NO 318
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 318
tagttttcat tgcacatttt tccttacaag ncgggccttg tccttcacct tttgcatctc    60
c                                                                    61

<210> SEQ ID NO 319
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 319 aggggggagac tgtgaggttt gttgaccatc ngtttgtacc tggggctgtg ttccagcttc    60
a                                                                    61

<210> SEQ ID NO 320
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 320
catacctgcg gaacctcggg cggtaagtcg nattccgatg agcctggagc tgtgttccct    60
c                                                                    61

<210> SEQ ID NO 321
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or a

<400> SEQUENCE: 321
aagcctagtt ccatctgctg cagtctgcag ngtttccttt ggaatctcca taattgcttt    60
g                                                                    61

<210> SEQ ID NO 322
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 322
tggtcctgtg cactacagtc cagaggaagg natccactgt gcagctgaaa caggaggcca    60
c                                                                  61

<210> SEQ ID NO 323
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 323
cagctcggtg tccccctggc gcgtacattc nttcagttca agaaggctct gagccacttc    60
c                                                                  61

<210> SEQ ID NO 324
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 324
cttgctagga gaacgcgttg tggcctttgc ngccgtagaa ggaatcttct tttccggttc    60
t                                                                  61

<210> SEQ ID NO 325
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 325
gtgtgagact tgtgggacag aagaagcgaa ntacagatgt ccacgctgca tgcgcttttc    60
c                                                                  61

<210> SEQ ID NO 326
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 326
catcagcaag acattagtgt tatgacgatt nctgagcatc ctgacatcca tgatttagag    60
a                                                                  61

<210> SEQ ID NO 327
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 327
atttaattct tcatcttggg aaacaatttg nttgctattc atcattatct tattaaattc      60
a                                                                     61

<210> SEQ ID NO 328
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 328
cacacccttt atgagcttgg tgtcttccag ncgcccacct actttgcctt ccactttaat      60
g                                                                     61

<210> SEQ ID NO 329
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or a

<400> SEQUENCE: 329
gggtgctcct cactggatca gtgccacacc ngggcagccc tctccaccag tctcctctat      60
g                                                                     61

<210> SEQ ID NO 330
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 330
cctcctgctg ctccaggcct acaactccca natggtctct agacgctccc actgcctctt      60
g                                                                     61

<210> SEQ ID NO 331
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 331
tttttctaaa aattctttac agtacaccag nagattcttc ccggtcaaat ctttttgaag      60
a                                                                     61

<210> SEQ ID NO 332
<211> LENGTH: 61
<212> TYPE: DNA
<213> ORGANISM: Mus musculus
<220> FEATURE:
<221> NAME/KEY: misc_feature
<222> LOCATION: (31)..(31)

<223> OTHER INFORMATION: n is a or c

<400> SEQUENCE: 332
tgaggtaagg gctccctgca tctcctagca ngtgggacag cactatctgg aaggcctcag    60
c                                                                    61

<210> SEQ ID NO 333
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 333
gcaagcatct ccgctttctt cttcagaaac ncaacaatgt actctgcaag cccttccttc    60
g                                                                    61

<210> SEQ ID NO 334
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 334
agcctctcgc agggccccgg gccggccgcg ncttgggctt ccgcctccgg ctccgggctg    60
a                                                                    61

<210> SEQ ID NO 335
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or a

<400> SEQUENCE: 335
tgctcttagg cctggctcct ccccagcatc ntatccgggt ggaaggaaat ttgtatcccg    60
a                                                                    61

<210> SEQ ID NO 336
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 336
cccgagtatc tggaagacag gcagactttt ngccacagcg tggtggtacc ttatgagcca    60
c                                                                    61

<210> SEQ ID NO 337
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 337 tccttttcc ctttagcaga gtcaggggat nttgggacag tcatctgtcc atcagatgac    60
c                                                                  61

<210> SEQ ID NO 338
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 338
catcttcttc ttcatcgagc tctgattctt ncagcagttc ttcagattcc gaagatgagg    60
t                                                                  61

<210> SEQ ID NO 339
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 339
agcgtcaagt ttgagatccc ctatttcact ncctctggca tccaggtatg aatgtgttag    60
g                                                                  61

<210> SEQ ID NO 340
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 340
gcttttgttt tcttgttgca gactctggtc nttttggtat tcctttaacg atattgttag    60
a                                                                  61

<210> SEQ ID NO 341
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 341
atcttgttaa agtttggttc cagtgtcaga ngcaagcaca gttattgctg tgtcttcagc    60
t                                                                  61

<210> SEQ ID NO 342
<211> LENGTH: 61
<212> TYPE: DNA
<213> ORGANISM: Mus musculus
<220> FEATURE:

```
<221> NAME/KEY: misc_feature
<222> LOCATION: (31)..(31)
<223> OTHER INFORMATION: n is c or t

<400> SEQUENCE: 342
ggtcgcaggc ggccatcatg ttcttggcat ngaagacctg ctgggtaagt tcaggcacag        60
t                                                                        61

<210> SEQ ID NO 343
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 343
cacgcactct tcatcaaatt tttgagaaac ntactgataa tggcactgag ttttcagtta        60
a                                                                        61

<210> SEQ ID NO 344
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 344
aggcaatggg tcgtgcgaga tgaacagtgg ncagaagaat gaggagaaga gtctggaaca        60
c                                                                        61

<210> SEQ ID NO 345
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 345
cctcttaacc cacagtgaac ttaggaggac ntctactaca ggcactgctg gaatactggc        60
c                                                                        61

<210> SEQ ID NO 346
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 346
gccattgtag atgccgccct cagtgccttg ngccagctcg tcaaggatcg ccttggtggg        60
c                                                                        61

<210> SEQ ID NO 347
<211> LENGTH: 61
<212> TYPE: DNA
<213> ORGANISM: Mus musculus
```

<220> FEATURE:
<221> NAME/KEY: misc_feature
<222> LOCATION: (31)..(31)
<223> OTHER INFORMATION: n is t or g

<400> SEQUENCE: 347
gtgaagaaca cgttgccttt ttcaagcagg ntttggaga acaagctcta atgaggccta    60
c                                                                  61

<210> SEQ ID NO 348
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 348
gtcgagatta tgagtacaac agatacagag nctattacag acaatacaac cgggatgtga    60
g                                                                   61

<210> SEQ ID NO 349
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 349
gggatcaggc acgcgtcgcg gcccggcctg nggaccagtc gtccctgcag cagcgcctga    60
t                                                                   61

<210> SEQ ID NO 350
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 350
gttttcttcc agattgaaag cttacgcaca ntcacagact ggggtccaaa ttttaatgag    60
g                                                                   61

<210> SEQ ID NO 351
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 351
gttggggttc tcaatgtcaa tgagcccctc nacgccttt cgcttttgct aggacagaac    60
a                                                                   61

<210> SEQ ID NO 352
<211> LENGTH: 61
<212> TYPE: DNA

<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 352
aggtccagaa gcagctggca aggatgacac ngtgccccga gcaggagctt cgcctgcagc    60
g                                                                   61

<210> SEQ ID NO 353
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 353
ggctgtcaaa tactcataca gtgctttagc ngaggccaca tctttgtcta aggctgaagg    60
a                                                                   61

<210> SEQ ID NO 354
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 354
cacaaggaac ggaagaaggc caatgaagtg naccgcatgg tacttgtggg agatgtgaag    60
g                                                                   61

<210> SEQ ID NO 355
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 355
gccatcttca acaggaagat cagcaggaac nccaccttta aggtgctgaa ggacagagta    60
a                                                                   61

<210> SEQ ID NO 356
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 356
aggaatataa agagaaggag atcacaatca ncaaccctgc acagttccct gagaagtccc    60
a                                                                   61

<210> SEQ ID NO 357
<211> LENGTH: 61

<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 357
gatgcaggag atgatgatga taaggagggc nccattggtg tgaggaacaa ggtggctggg    60
g                                                                   61

<210> SEQ ID NO 358
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 358
acttctgaag gtttggccac atctttttca nccacatatt ttgcccatgg tcccaagaaa    60
c                                                                   61

<210> SEQ ID NO 359
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 359
actcacatct tgattgtatt ccaagaagac ntggaaattt aaatcttttc tcaaaatagg    60
a                                                                   61

<210> SEQ ID NO 360
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 360
tgttagggca ggccaacttc tttatgatgt ngcattatgt gctggttctt ttccgagggt    60
c                                                                   61

<210> SEQ ID NO 361
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 361
tcttcaagat ttagattcaa cccctcttct ncaaacacct ataaaagcag tgtgctatta    60
g                                                                   61

<210> SEQ ID NO 362

```
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 362
cttccttctc ctcctcttct tctttctctt natcctcctc cgaagtcact tcctcctcct        60
t                                                                       61

<210> SEQ ID NO 363
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 363
actacatgag ggaaggggca ccgctgtgtg nacacgaact tctgcagctg ggacagcagt        60
t                                                                       61

<210> SEQ ID NO 364
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 364
atcaggtaac acctggatcc ccttttctg ntgattattg ttttgtgttg ttgaacttt         60
a                                                                       61

<210> SEQ ID NO 365
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 365
agcaactccg aaaagtagtt ctgagcatgc ncatttgccg aaacctgtgg aagcctttaa        60
g                                                                       61

<210> SEQ ID NO 366
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 366
tcttcttttt ggctgaagtt ctttgtttct nctgcttttt attatcttct gagcttccct        60
c                                                                       61
```

-continued

```
<210> SEQ ID NO 367
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 367
ttcgtgatac aaggaatatt attgtggaga ncatgctgaa taaacaaaga gcctaggtca        60
a                                                                       61

<210> SEQ ID NO 368
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 368
ggagcccctg atccgcaggt cagatgacaa ngagaaagcc ttgaagaccc gcctggaggc        60
c                                                                       61

<210> SEQ ID NO 369
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 369
tgagcaatga cgacgctgta cgggtgcttc nggagatcgt gtcccagaca gggtgaggtg        60
g                                                                       61

<210> SEQ ID NO 370
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or t

<400> SEQUENCE: 370
atgatgaatg tgggctggcc tatgttaaac nacaaggaat tcgtttccaa gaaaagccct        60
a                                                                       61

<210> SEQ ID NO 371
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 371
gtatcgtcaa ggcgctcttg cctacgccac nagctccaac caccacaagt ttatactcag        60
t                                                                       61
```

<210> SEQ ID NO 372
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 372
tgctaaagcc tttgctcttc ttgatctcct ngcaggcagt actgacagcc atgatgtcag   60
g                                                                  61

<210> SEQ ID NO 373
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 373
ttaaatgcag accatggatt cctgtgattt ncgaggactg acttctagac gaaggacctc   60
a                                                                  61

<210> SEQ ID NO 374
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 374
aaatgaactg gcttgtgcag gccatctacc ngaaaattta cgccacgaca gtcggacatt   60
t                                                                  61

<210> SEQ ID NO 375
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 375
tataaaagcc ttccgaatat tggcaagaaa ngctgaaaaa ttgttggtct tcctgacttt   60
c                                                                  61

<210> SEQ ID NO 376
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 376
tccttgctcc cgagagttta tcaaggcaca nggcccagcc ggagaggtgt actgccccag   60
t                                                                  61

```
<210> SEQ ID NO 377
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 377 taggaattttt ctttaggctt ccacttccac ngctgctgag actacgcaga cttgcgcgat    60
g                                                                    61

<210> SEQ ID NO 378
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 378
caggagtggt ttgtcggagc agcgcttgcc ncaatgattc cgtgttttta caggtataca    60
a                                                                    61

<210> SEQ ID NO 379
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 379
tccagtagga agtggaagcc atcattggtt nggtatttct gaataccgcc acagatacca    60
g                                                                    61

<210> SEQ ID NO 380
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 380
cttgatcctc tcctttccca ggcctagcca ncatgaccca gcacctggag cctattctga    60
a                                                                    61

<210> SEQ ID NO 381
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 381
ctgtgtggca aagagactgt ggtgaccagc nccacggagc ccagtcgctg tgagtacctc    60
``` a                                                              61

<210> SEQ ID NO 382
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 382
gtgatataga atctctaaaa gctagtaatg nagactcatt cccttggaat aatatgcgac    60
t                                                              61

<210> SEQ ID NO 383
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 383
tgcactggca ttgtaccagg tacttactct nggtaaagca gcgacttggt aagcagccct    60
g                                                              61

<210> SEQ ID NO 384
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

<400> SEQUENCE: 384
tggcccatct tcaggatcca tcaccagaaa ncccgctata tcttcgacct cttttacaag    60
a                                                              61

<210> SEQ ID NO 385
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 385
gtccagttgt actcacctgt cttgtctttg ntgaggtctc aatgaacgga atcccgtaac    60
t                                                              61

<210> SEQ ID NO 386
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 386
gaatttcctg atttctcaag aggcttaaaa ntacctccat atttggcagg tagggaaagc    60

-continued

| t | 61 |

<210> SEQ ID NO 387
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 387

| cagcacaact acgccgcacc cccctccaca nggaaggact atccagctgc caagagggcc | 60 |
| a | 61 |

<210> SEQ ID NO 388
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 388

| cagaggcgga gctcaggaag gtggatgagg ncatcgccct gttccagaag atgctgtgac | 60 |
| c | 61 |

<210> SEQ ID NO 389
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 389

| agccaactct cggaggtggc cagtaaattt ncaaaagcga ccggcgctgt gagtccttgg | 60 |
| t | 61 |

<210> SEQ ID NO 390
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 390

| cgaatcacag agctaaagga ggaaatagaa ntgaagaagg tactggatac gtacgtctgc | 60 |
| t | 61 |

<210> SEQ ID NO 391
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 391

```
ccattactgc ctgtgctggg ccacccgcgg nggccaggag cttggtaaga gatccatcgc    60
g                                                                   61

<210> SEQ ID NO 392
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 392
taccccagtc tattccagga gtctcagcaa ngatgccaga gtcggaaaca gcttccaccc    60
c                                                                   61

<210> SEQ ID NO 393
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 393
acagagctta cctcgtaacg ctccccaaac nctgttggcc ttgaggacgg ctactggttc    60
t                                                                   61

<210> SEQ ID NO 394
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 394
tctctcaccg tttggtccca gtgacgtccg nattgtgttt gctacagctt tggcagccat    60
g                                                                   61

<210> SEQ ID NO 395
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 395
gcaacccaag cccagagtct gagggcagca nggtgcccac acagcctgag gaaacagaag    60
a                                                                   61

<210> SEQ ID NO 396
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 396
```

```
agggttggct tcaggcccat tgggagcacg natgtacttg gggaagagat ggggaatgac    60
c                                                                    61
```

<210> SEQ ID NO 397
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 397

```
ccactgtggg gaagttgaac tttcgaagca ncatacaaag gatctggcag gtcctggtgg    60
g                                                                    61
```

<210> SEQ ID NO 398
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 398

```
aagagcttca gtctcatgat cagaacacca ngggctgtgt acgctaacag ctgcagagcg    60
t                                                                    61
```

<210> SEQ ID NO 399
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 399

```
gggacggcgt gattgaggcc agcatcaatc ncgagaaggg atacgtccaa tccaaagaga    60
t                                                                    61
```

<210> SEQ ID NO 400
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 400

```
atgaacgtaa ggaagagaag tcgttacacc ngagtatgcc tattattaca gaggaggagg    60
a                                                                    61
```

<210> SEQ ID NO 401
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 401
cagaaacttt attgttacgg gcttacagga natagataaa tgcagacagc agctgcacga    60
t                                                                    61

<210> SEQ ID NO 402
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 402
atcgtctcaa agatcttccg tttattgttt nacataggtt gtctaatacc ttgagcttag    60
a                                                                    61

<210> SEQ ID NO 403
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 403
ctctcaagtc gaccacgagt ccctgcatcc ngggccccta ggctcagctc ttctaagtct    60
g                                                                    61

<210> SEQ ID NO 404
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 404
attgttcctc caatgattcg gcccaaaggg naccaagccc ggtcatcaaa ccagttatgg    60
a                                                                    61

<210> SEQ ID NO 405
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 405
tagtcggatt tctgtggcct cacacacctg ntaaagctgg acctcagcaa gaacaagctg    60
c                                                                    61

<210> SEQ ID NO 406
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or c

```
<400> SEQUENCE: 406
ccaagaaaaa ttaaagaaga tgatgctcca ngaacaatag cttgccctca taaagtaagt    60
a                                                                   61

<210> SEQ ID NO 407
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 407
ctctatgtca atatctccag ccgtagtttt nagtaaaacc tatagaaaga tcatgacatc    60
a                                                                   61

<210> SEQ ID NO 408
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or g

<400> SEQUENCE: 408
taaaagcacc tcgcagaatg aatgcctccc ngaagcaatg tcttgcagaa ttttaggaga    60
g                                                                   61

<210> SEQ ID NO 409
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 409
agcagcagct atgggcaacc ccagagtgga ngttatggtc aacagtctgg ctatggtgga    60
c                                                                   61

<210> SEQ ID NO 410
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 410
cgcctaggac ttttcctag ggccatggcg nactcgacgt ttttggcacc agaactaagc     60
g                                                                   61

<210> SEQ ID NO 411
<211> LENGTH: 61
<212> TYPE: DNA
<213> ORGANISM: Mus musculus
<220> FEATURE:
<221> NAME/KEY: misc_feature
<222> LOCATION: (31)..(31)
```

<223> OTHER INFORMATION: n is g or t

<400> SEQUENCE: 411
ggcggctgtg cagccaacat ggcggcggcg ncggcggcgg gcccggagat ggtccgcggg    60
c    61

<210> SEQ ID NO 412
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 412
tccgtatgag gaatgttcat aaccacctct ncctccgcct cggcctcctg cttgctgctg    60
g    61

<210> SEQ ID NO 413
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 413
ccacaccgta gtggtagcca gaggccacat ncccacagac caggcagagg cgtttgggta    60
g    61

<210> SEQ ID NO 414
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 414
agcagctggg cccgccgcct cctctgcctg ntcggcctct tggtgctgct cctgtggttc    60
g    61

<210> SEQ ID NO 415
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 415
tctttctgat gtacacaata tgaatgtctt nacttcggta ttcttcatca tgtttgtcca    60
a    61

<210> SEQ ID NO 416
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 416
tggccatgag ctgcgcaggg ttgatggaat ngatgtctcg cagagaagcg tgtgagctct    60
g                                                                   61

<210> SEQ ID NO 417
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 417
tcaaataaag gtgagctttc tttcatggca ntatcaatct aattaatata cagacaacac    60
a                                                                   61

<210> SEQ ID NO 418
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 418
aaggggaaga cgtcgaaggc gactgcaaca ngttggctct tcacatatca accagccctg    60
g                                                                   61

<210> SEQ ID NO 419
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or t

<400> SEQUENCE: 419
gcctctgcat ctgcccaaca acaacaactc nacagagtgg gaaaaggtga agctcctgtt    60
t                                                                   61

<210> SEQ ID NO 420
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 420
ccgtgtgtct cccgcagccc ggcgaccatg nccaggaaga aggggcggc ctgggaggag    60
c                                                                   61

<210> SEQ ID NO 421
<211> LENGTH: 61
<212> TYPE: DNA
<213> ORGANISM: Mus musculus
<220> FEATURE:

-continued

<221> NAME/KEY: misc_feature
<222> LOCATION: (31)..(31)
<223> OTHER INFORMATION: n is c or a

<400> SEQUENCE: 421
gagtcccagg cacgggtcag ccagctgaac ntgcagatgg aggggcagca gcggcgtctg    60
g                                                                   61

<210> SEQ ID NO 422
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 422
aaccttctgg gacgggacag ctttgaggtt ngtgtttgtg cctgccctgg gagagaccgc    60
c                                                                   61

<210> SEQ ID NO 423
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or a

<400> SEQUENCE: 423
ccaggaattc tttgtctaac tgtggaattc nacaacccaa atatggagac agaaaagttc    60
a                                                                   61

<210> SEQ ID NO 424
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 424
atcgcatgat tgactttcta cggttccggc nagaaaagga aaaggcacca gaaccgtttg    60
a                                                                   61

<210> SEQ ID NO 425
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is a or g

<400> SEQUENCE: 425
ctaagacaag tacctggccg gaggtgctag ntcaggaatg cgtgcgtcaa cgactggcac    60
t                                                                   61

<210> SEQ ID NO 426
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 426
gccacacaac caacctcact ggggcagcta nctggtcagc ctccaggcca gtccaaccag    60
a                                                                   61

<210> SEQ ID NO 427
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 427
ctacaggccc ggaggaacca tggtgaccta nggggaatg gccaaacagc ctgtaacagc     60
c                                                                   61

<210> SEQ ID NO 428
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is t or c

<400> SEQUENCE: 428
tgactcctct gatggcagct tatttaaaac ncagtgtgct ccttcaccta tacaaaagca    60
a                                                                   61

<210> SEQ ID NO 429
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 429
ccgccctgga aggttctccc tctctggacg naggccctcc tcccttTGGG ctggagtggc    60
g                                                                   61

<210> SEQ ID NO 430
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or t

<400> SEQUENCE: 430
tcatacctgt ttgagcatca ctggatgtgc ncttgtcctt aggaaatgga ttatctagga    60
a                                                                   61

<210> SEQ ID NO 431
<211> LENGTH: 61
<212> TYPE: DNA

<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 431
ttggaaacaa tgctggctct gaagaacaat nacctgcgta aaatccctgg ttataatcct    60
g    61

<210> SEQ ID NO 432
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or g

<400> SEQUENCE: 432
ccgagaagat gccgaaggcc aagtccgcag ngagtagccg ccggcgggat cgtcaggagc    60
a    61

<210> SEQ ID NO 433
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or c

<400> SEQUENCE: 433
gcgacgctgg ggttgtgttc acctccggcg nctccggctc gctgcggctt ctctggcttc    60
t    61

<210> SEQ ID NO 434
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 434
gatcttagct ctccatcaag atcctgctgc ngcagtttcc tgaaatctgc atcaagggcc    60
t    61

<210> SEQ ID NO 435
<211> LENGTH: 61
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is c or a

<400> SEQUENCE: 435
aactgagtcg ctatccagag gacaagatta ntcctgagaa cttgccccaa attcttctac    60
a    61

<210> SEQ ID NO 436
<211> LENGTH: 61

```
<212> TYPE: DNA
<213> ORGANISM: Mus musculus
<220> FEATURE:
<221> NAME/KEY: misc_feature
<222> LOCATION: (31)..(31)
<223> OTHER INFORMATION: n is g or t

<400> SEQUENCE: 436
gtacctgtaa gcctggagag taagaaggct ncccgggcgg ctaggtttgg aatttcttca    60
g                                                                    61

<210> SEQ ID NO 437
<211> LENGTH: 150
<212> TYPE: DNA
<213> ORGANISM: Mus musculus

<400> SEQUENCE: 437
ccctggagct gcacaccgag ctgttggaga gcggccgcga gctaccacga ctgcgcgatt    60
acttctccaa tcctggcaac ttcgagaggc agagtgggac ccccccaggg atgggggcgc   120
ccgggatccc tggcgcctcc atcgtcggag                                    150

<210> SEQ ID NO 438
<211> LENGTH: 141
<212> TYPE: DNA
<213> ORGANISM: Mus musculus

<400> SEQUENCE: 438
ctggaccggt acctggctgt ctgtcaccct cttcgaagcc tccagcagcc cagccagtcc    60 acctacccte ttattgctgc tccctggctg ctggctgcca tcctcagcct ccctcaagtg   120
ttcatttttt cgttgcgaga g                                             141

<210> SEQ ID NO 439
<211> LENGTH: 157
<212> TYPE: DNA
<213> ORGANISM: Mus musculus

<400> SEQUENCE: 439
ctttaaaaaa ttacagtaat aataaattag ctattgctct tcagaggctc acggaacagc    60
taacacaaca ggaccaggtc cagagttagg tccgtatctc aggttctcga gctgcccggc   120
cctctttaaa gcttagacga atttccaaat acaagac                            157

<210> SEQ ID NO 440
<211> LENGTH: 191
<212> TYPE: DNA
<213> ORGANISM: Mus musculus

<400> SEQUENCE: 440
gctaaagtct cttgaatatc tataaacagg aaatcatatg ccaattacta gttctgaaga    60
gtgtctacat cattaaaaaa acctttcatt tttctttctt cctttttttt ttttggcga    120 tacagatttc aagagtaacg ctggaaaact gtgaaaaatg ttatttaaaa aaatatatgc   180
atatgttact g                                                        191

<210> SEQ ID NO 441
<211> LENGTH: 141
<212> TYPE: DNA
<213> ORGANISM: Mus musculus

<400> SEQUENCE: 441
```

```
ggaagaatta aatgttcttg acattccatc taatagacag tgggtggcat catcttaagc      60
agcacatgat ggaggtttga atttggcagt attttcgtta tttgggctac aaactctacc    120
caaatttgaa ggactttcta c                                              141

<210> SEQ ID NO 442
<211> LENGTH: 193
<212> TYPE: DNA
<213> ORGANISM: Mus musculus

<400> SEQUENCE: 442
tggttcccct ccaactacgt tttggaggaa gcggacgaag ctgcggctga ggccccagc      60 ttcctgagcc tacgtcgggg cactgcactg agcaatgggc agggtgcacg ggtgctgcac    120
gtggtgcaga cgctgtaccc cttcagctcg gtcactgagg aggagcttag tttcgagaag    180
ggggagacca tgg                                                       193

<210> SEQ ID NO 443
<211> LENGTH: 179
<212> TYPE: DNA
<213> ORGANISM: Mus musculus

<400> SEQUENCE: 443
gtattttctt tatgttaaag ctgtaattca aagttctcat ttttaaaaat gattttgtat      60
gcttagattt ttccagtgtt tcctattatc cttttatat tttatataga aatattataa     120
cccaaatgac catttttttcc attatcattc tacatattaa aaaataaaa ttatttta     179

<210> SEQ ID NO 444
<211> LENGTH: 180
<212> TYPE: DNA
<213> ORGANISM: Mus musculus

<400> SEQUENCE: 444
ctttgcccaa tccccacttt ttttttctcct tctaaaagag acaaagggaa atacttaaga    60
accaatagtg acagcgacag caatcattga gttgcagggt accttttgtct ctgggggca   120 cgcagtaatt tttacatgtc tgccactgag tgtcaagcct tttctttttct tcttctttcc  180

<210> SEQ ID NO 445
<211> LENGTH: 177
<212> TYPE: DNA
<213> ORGANISM: Mus musculus

<400> SEQUENCE: 445
tagtgagata gcacctatta attctacact agaaactgac ctttaccgcc taattttcaa     60
gttaaatgtg atggtacctt gtgtgaagac ggttggggca cttaccatgc cggccggcct   120
tctattgctt cttttgctgg gctccctaca aagcatcggt ttccattaag tcaaaat      177

<210> SEQ ID NO 446
<211> LENGTH: 215
<212> TYPE: DNA
<213> ORGANISM: Mus musculus

<400> SEQUENCE: 446
atttataaag caataaatat ttgaagcaca aacaaactgc acttgtgtaa acaaactgta     60
caatgactga tgagagatgg ggagggggct cagaggattc caagaagcac aatacggtca   120
tcctgaatat aaggtaggct aagagagaga catctcagaa gcacttgcgg tggacaatgg   180
atgggcctgc ctcatcatac tcttgcttgc tgatc                              215
```

<210> SEQ ID NO 447
<211> LENGTH: 194
<212> TYPE: DNA
<213> ORGANISM: Mus musculus

<400> SEQUENCE: 447
ttcagctgca gagacagagg gcttcatagt caagctctga agaaaggatc aaatatgggg    60
aagtaggtct atctaccaat gaagcaaaag caacaggcat atgctgtgtc agataacaca   120
cacacacaca cacacacaca cacacacaca cacacttacc agtggtgaca aaggagtacc   180
cgcgctcagt gagg                                                    194

<210> SEQ ID NO 448
<211> LENGTH: 178
<212> TYPE: DNA
<213> ORGANISM: Mus musculus

<400> SEQUENCE: 448
cctgcaaaag ctattgttac aattcttatg gagttccccc atgcctctta taaatgagcc    60
atatttagtt ttaaacaaat tcttgaagt aaacagtata tatgcctgat tttcatctct   120
cttggtgagc ttccaaaaaa cttggaagtg aattagtgtg caatttgcat ccaaatct    178

<210> SEQ ID NO 449
<211> LENGTH: 197
<212> TYPE: DNA
<213> ORGANISM: Mus musculus

<400> SEQUENCE: 449
attaacacag ctctgcagct actagaaatg aatttcaaag atggtaaatg aacaaaagcg    60
attcatatct ctaagaaaag caaacactgt gcccagaacc atatacactt tgaaaaggta   120
cagtatataa aacctcttta actctcccac ttaaagaaac agcggaaggg aacgtttgga   180
gaaaggaaaa ctgactc                                                 197

<210> SEQ ID NO 450
<211> LENGTH: 207
<212> TYPE: DNA
<213> ORGANISM: Mus musculus

<400> SEQUENCE: 450
gctcgaatga tcaattccca ttttatgatc gctgacaaag tcaggctaga ggcggggtga    60
gaccgcgttg ttggcttggc cgggacaggg gcttcgggta cgcccagctc cgcccggcgc   120
ctccggaggc tgctctctct ccagcgagtt cagagacctt ggcaaacttc cctcccccac   180
acgcagccga gacttctgag ttgtcac                                      207

<210> SEQ ID NO 451
<211> LENGTH: 137
<212> TYPE: DNA
<213> ORGANISM: Mus musculus

<400> SEQUENCE: 451 ttattttttgg cgtgggaacg cggggagcac ggcggtgaga aaggccgagg ctgccagcgc    60
cgctgacggg cctcttcctg tattttacac cttttgcgaa ttccgctcct ttggaaaggg   120
aataatggct ttgggat                                                 137

<210> SEQ ID NO 452

<211> LENGTH: 155
<212> TYPE: DNA
<213> ORGANISM: Mus musculus

<400> SEQUENCE: 452

```
ctttccatcc tggaccttga cccaaggggg tctgggaatc tgctagtgtt ttggcacaaa      60
acacactgtt tttcctcttg ctatcattta gatctctaga ccttgtgcag gacactgttt    120
atgctactta actaggctct gtgggagtga cgaca                                155
```

<210> SEQ ID NO 453
<211> LENGTH: 115
<212> TYPE: DNA
<213> ORGANISM: Mus musculus

<400> SEQUENCE: 453

```
tttaaccatt ggaacattat ttcataacta gttttttaaaa tttattttgt catccagcca     60
ggtttctttt tttttttttct tttttacattg tattaatacc aaagtgaaaa acggc        115
```

<210> SEQ ID NO 454
<211> LENGTH: 174
<212> TYPE: DNA
<213> ORGANISM: Mus musculus

<400> SEQUENCE: 454

```
gtaaatattg acattttaat tttgtttagc ataccaagct ggggtttccc gttgcttatc      60
ttgctgtaaa aactcctcac ctcccctcgc actgccctgc agactgtcgg gaaaagatct    120
gaacagagca gccccgggtg ctctgccctc tttgctaaca aggcttagtt ttgt           174
```

<210> SEQ ID NO 455
<211> LENGTH: 193
<212> TYPE: DNA
<213> ORGANISM: Mus musculus

<400> SEQUENCE: 455

```
tatcctgctc gagggcctgg gaacgtggca gggacctggg cctccgttct aattaatagt      60
cttttttgtc cttttttttt tttttctgt ttttttttttc ttaccctac tggcaaaaaa    120
ataggagggg gggggtgcta ccggtaattg ttttcctcaa aggctgcagg gagttatcag    180
ggtaataaag tta                                                        193
```

<210> SEQ ID NO 456
<211> LENGTH: 162
<212> TYPE: DNA
<213> ORGANISM: Mus musculus

<400> SEQUENCE: 456

```
agtgtgcact ccgcaaaact ccaccagtgc cctttccttt catgatctca acaagcgcta     60
ttacaacacc ttccattgca acttcactat ttcctgccag tcaataagtc agcatgtgga   120
tatggctctg gtccgtctta tccatcaatt cagtacaatg at                        162
```

<210> SEQ ID NO 457
<211> LENGTH: 197
<212> TYPE: DNA
<213> ORGANISM: Mus musculus

<400> SEQUENCE: 457

```
caattgaagg tccatcgcat tattcatcaa atagtgaagg atcgtgttca gtgttcagct      60
ctcccaaaac cacaggcggc ttttcaccaa gtgttccttt ccagtcagaa gatggccgaa    120
```

```
gggacgacag tctgtcttct accagtgaag actctgagaa ggatgaaaag gatgaagacc    180
gtgagaggga aagattc                                                  197

<210> SEQ ID NO 458
<211> LENGTH: 201
<212> TYPE: DNA
<213> ORGANISM: Mus musculus

<400> SEQUENCE: 458
ctgtttcctg tgaaaaatac atagaacaat aatagccttt gtttctaatg ttccaactac    60
taaaacagct gaacaaataa catccatgct ttcatttttt catgctttca tttgtaataa   120
tttattccat gtacacgttt atacagaatc atttggctta ttggatgttt catcgtttaa   180
aaatcaaaat ttagaatttt a                                             201

<210> SEQ ID NO 459
<211> LENGTH: 139
<212> TYPE: DNA
<213> ORGANISM: Mus musculus

<400> SEQUENCE: 459
attggcagag catttgggta attcttccca tctccaagtg gctgccttgc acattgtcat    60
gaatattact tagagccagt gacactggct acaggctgac tcttcccaac atgtggactc   120
aatttgctct gctctatcc                                                139

<210> SEQ ID NO 460
<211> LENGTH: 150
<212> TYPE: DNA
<213> ORGANISM: Mus musculus

<400> SEQUENCE: 460
tccctctgct gtggttggct ggctccaggc aagatttggg tagaccagta tggaagaatg    60
catgcagccc gtggtgtctg tgtctagaac ctggctgcca ggattttttgc aagcagatac   120 tgcagcttgc ttgcaaccgg gcccaggctt                                    150

<210> SEQ ID NO 461
<211> LENGTH: 203
<212> TYPE: DNA
<213> ORGANISM: Mus musculus

<400> SEQUENCE: 461
ttacgaggtt ggcggctcta agaggcgcgg ggctggggac cagtggacca gcagggtagg    60
ggtctctcct gctgcatccc accgggccca ggtcagcgcc ccgtgcaccg cggcgacccc   120
gcccactact gaatgtggca ggcggtggag gaagtggcct gacaacacat gcaggtgggg   180
ttcacagact tgggggggat gag                                           203

<210> SEQ ID NO 462
<211> LENGTH: 179
<212> TYPE: DNA
<213> ORGANISM: Mus musculus

<400> SEQUENCE: 462
aaggtaggac ccgcagagag gacagagggg cgggaccgag ccttggacgg gaggctagaa    60
cttagaggcc ccgcagcctg ggttagagat ccttgagcta gcagccaccc aacctgtcgg   120
gcacacacgg agccttgcct cccccaggtt cggcaccgac agtcgggaca agtcatggt    179
```

<210> SEQ ID NO 463
<211> LENGTH: 175
<212> TYPE: DNA
<213> ORGANISM: Mus musculus

<400> SEQUENCE: 463
ccgagtgcct gcagaccctg actacctacc ccgcactgag gtgaggtaac ctctgctctg    60
ggtgcctcaa ccaagaaggg ctttgtggag cttgagcctc acagtggggc acatggagag   120
cccactgaag gctaactggc agcccctcct ctgtccccac aggactttgg cctgg        175

<210> SEQ ID NO 464
<211> LENGTH: 142
<212> TYPE: DNA
<213> ORGANISM: Mus musculus

<400> SEQUENCE: 464
tgtaaagtca accaaggaac agacagtgaa gaaggcctgg aagggaagga ggagcagcct    60
gataggaaca taaagtgact tatgtatgaa caaagaaaac taacttgaaa aatggaggtt   120
accagggtaa ccggagtcat ct                                            142

<210> SEQ ID NO 465
<211> LENGTH: 143
<212> TYPE: DNA
<213> ORGANISM: Mus musculus

<400> SEQUENCE: 465
aatctgtacc caaccttgtc actggtccca gcagctgttt gaactcaccc gcggggatgg    60
cagcaaccct gcttctgaaa gaacagcaga agggcttacg tgcactgcgc cttgaagagc   120
gcctgaaagg aaggtcaaag gtc                                           143

<210> SEQ ID NO 466
<211> LENGTH: 150
<212> TYPE: DNA
<213> ORGANISM: Mus musculus

<400> SEQUENCE: 466
atgggaactg gagctgtccg aggccagcag gcgggatttc cgggaagcac tggcccattc    60
agatttacac cgagctctga cttccccacc tacccaccag cagctactga aggacccaat   120
atagtttgca aagcctgtgg gctttcgttt                                    150

<210> SEQ ID NO 467
<211> LENGTH: 138
<212> TYPE: DNA
<213> ORGANISM: Mus musculus

<400> SEQUENCE: 467 gcccctgca tttggcgga gggggaaagg agggaagacc aaagaaaaga agcaaaaaa       60 ataaataaat agagcaagcc agagccgata tctacaaagt tttgcaccaa cacttaagca   120
gatccgtttg caaagtcc                                                 138

<210> SEQ ID NO 468
<211> LENGTH: 203
<212> TYPE: DNA
<213> ORGANISM: Mus musculus

<400> SEQUENCE: 468
gcttccagga aaccattgga ctcggctccc aaagccgtgg acttgaaaga gaagcccagc    60

```
ttcctagcca agggatcaga aggccctggg aaaaactgtg tgccagtcat ccagcggact    120
tttgctccct cgggtgggga gcagagcggc agtgacacgg acacagacag tggctatgga    180
ggtgaattgg agaaggggga ctt                                            203

<210> SEQ ID NO 469
<211> LENGTH: 189
<212> TYPE: DNA
<213> ORGANISM: Mus musculus

<400> SEQUENCE: 469
ggggaagtgc tcatgtaga gctcccggga gccacctcct gtccgtacgg cctggttcag     60
ctcccagtac aaggtgttgg atgagttggt gtacaccata atcgctactc cgtgctgggc    120
tttgaagcca ggaggtagag tgagcttgtg acgccggtgt gcccaggcct cttgtgctgc    180
ttcccagga                                                            189

<210> SEQ ID NO 470
<211> LENGTH: 214
<212> TYPE: DNA
<213> ORGANISM: Mus musculus

<400> SEQUENCE: 470
agtgaccgct ctctctgctc tgcatccgcc ggctcggatg atcagtccct ctggaaatac     60
ccgggtttga ggacccccctt tggggctttt gttttttccga cttttggaac taaaccaaca   120
ctcctatcca atgggcccct tctgttgcct gcctcacacc cctcctgct ccctttgtcc     180 cctcagcact gtccttacta actgaaggga gggg                                214

<210> SEQ ID NO 471
<211> LENGTH: 171
<212> TYPE: DNA
<213> ORGANISM: Mus musculus

<400> SEQUENCE: 471
cttctgtctc catcaagaca ttatgaagct gtcctgtact gataccaaag ttaatgtcgt     60
ttatgggctc ttcatcatcc tatcagtcat gggtgtggac tccctcttca ttggcttttc    120
ctatatcctc atcctgaggg ctgtgttgga gctttcaact cgaggggcag c              171

<210> SEQ ID NO 472
<211> LENGTH: 145
<212> TYPE: DNA
<213> ORGANISM: Mus musculus

<400> SEQUENCE: 472
aattgtcttc tagctcacca ggctcctctg cagggctggg ccttcgacta gggctggaag     60
ttggagatgc agtaagccct ggtgatcgag gaactggacc tggggactca gagccaccta    120
ggctctgttg ccgaagaaac agagc                                          145

<210> SEQ ID NO 473
<211> LENGTH: 202
<212> TYPE: DNA
<213> ORGANISM: Mus musculus

<400> SEQUENCE: 473
cagtggccag gaagataaag ggcaggacag cagcttctgg gcctacgggc ctacgggcct     60
cttcagacca cagcagtggg caaaactggt gtcagacccc agtcagaaaa aacgagccca    120
```

```
agccagcaag taagtggcaa aggacatccc atgtccaatc tcctccaccc tggggctgcc    180
ccgcccagtg tccttcttga ta                                              202

<210> SEQ ID NO 474
<211> LENGTH: 153
<212> TYPE: DNA
<213> ORGANISM: Mus musculus

<400> SEQUENCE: 474
gacaaagcca aggcacccct tagagagctt ctccgaggtt cattacctac ccctagtttg    60
tctcttgccc caccttgcat ctcctccctc cacagcacaa ttaaggctaa gatcattctt    120
cttctctaga acgggcagag aaaatgggcc aga                                 153

<210> SEQ ID NO 475
<211> LENGTH: 154
<212> TYPE: DNA
<213> ORGANISM: Mus musculus

<400> SEQUENCE: 475
cgtggctgaa gagggtaagt gacgggctgc tttgtctggg tctctctgga gatgagtaag    60
gggagagaca ctttggggtg ttttggctgt gtgtgtgtgt gtgtgtgtgt gtaatagggg    120
aggtatttat ccagcgaacc ctattgtggc caag                                154

<210> SEQ ID NO 476
<211> LENGTH: 172
<212> TYPE: DNA
<213> ORGANISM: Mus musculus

<400> SEQUENCE: 476
gttcctgatt ctcattaccc tggtaggaaa ccttggcatg atcttgctca tcaaggcaga    60
ttccaggctt cacacgccaa tgtactattt cctcagccac ctggctttca ttgatctctg    120
ttattcatct tccattgggc caaaaatgct gcaaaattta ttggtgaaga aa             172

<210> SEQ ID NO 477
<211> LENGTH: 158
<212> TYPE: DNA
<213> ORGANISM: Mus musculus

<400> SEQUENCE: 477
acactctgac acagccgctc tatgaaatga ttcagatgga atatgccagc gtgctttttc    60
cccccaaacc ctttcagaga gttatgatgt tgctacgtaa gttaatgaga ggaatggcag    120
agcaaacgct gctctcaaaa cctgtcaaca gtataact                            158

<210> SEQ ID NO 478
<211> LENGTH: 177
<212> TYPE: DNA
<213> ORGANISM: Mus musculus

<400> SEQUENCE: 478
attgattttg aagttcaatg ttggcatctg ctgttattca aaaccaggac cttggctaca    60
gtaatccacc atgctttcgg cttcgccacc cgtgtgaggc aaatgaaggc aagctgttgt    120
cgagtgagaa atgcaaaata gccaatctgt ttgtctgttt aatgtaaccg ggaacat       177

<210> SEQ ID NO 479
<211> LENGTH: 211
<212> TYPE: DNA
```

<400> SEQUENCE: 479

```
atggatcccc gcagactcca tacctggtgt ccgggggaga ggcagtgtga gcaaccgcag      60
agtcgggcta agggaccggc gggtggagac cccgtactct gtggcgtggg gcgagggaaa     120
actgattccc gcacaccagc ggatcgggcg gctcaccgat aaaggaaggc tggaagagcg     180
tctccgggca acggaaacgc tcattgccga t                                    211
```

<210> SEQ ID NO 480
<211> LENGTH: 159
<212> TYPE: DNA
<213> ORGANISM: Mus musculus

<400> SEQUENCE: 480

```
tgactttcac cttggtccag tacaactctc cagtcacgtt gaaggactca cactcgctct      60
tgttgttcac aatggtgtag ttcagaggca ggtcccttc ggtctggttg atgcacctac      120
cgaacttccc ggcgaagagg ttcacgccca tgatgctga                            159
```

<210> SEQ ID NO 481
<211> LENGTH: 175
<212> TYPE: DNA
<213> ORGANISM: Mus musculus

<400> SEQUENCE: 481

```
cgaaagatca aaattatcg atttcatggc gctgtgtgct ctggaaaaga aaagctactt       60
taacatttgc attgtttaaa gacatctttt agaagaaaag gctcgcaccc cccacccca     120
aactctttgg gatgtgaaaa tggcttgttt tcatctccct catgattttc tataa          175
```

<210> SEQ ID NO 482
<211> LENGTH: 165
<212> TYPE: DNA
<213> ORGANISM: Mus musculus

<400> SEQUENCE: 482

```
atctctgacc tgctcttcct gctcacacta ccattctggg ctcactatgc tgcaaatgag      60
tgggtctttg ggaacataat gtgtaaagta ttcacagggc tctatcacat tggttatttt     120
ggtggaatct tcttcattat cctcctgaca attgataggt acttg                     165
```

<210> SEQ ID NO 483
<211> LENGTH: 203
<212> TYPE: DNA
<213> ORGANISM: Mus musculus

<400> SEQUENCE: 483

```
cagggaaata attggcacat gtttaaaaaa aaattaaaaa cctcttggat gtgagtattt      60
tctaacagca tctggcggga gtgcctggaa ggaatttaat cagcgagagt tgtttaaatc     120
ggtctactcg ctcggcccca gcgaggctcc taatgaactc ggtatcatgt gccacccctg     180
cctgctgagg acattcaatt tgt                                             203
```

<210> SEQ ID NO 484
<211> LENGTH: 151
<212> TYPE: DNA
<213> ORGANISM: Mus musculus

<400> SEQUENCE: 484

```
ggaacagtaa agaaggtccg atcagtatgt acaaaagaaa gagcctgcta ccgtggagca      60
```

```
aggctgccac ttatgacacg gtgctccagg tctagaagaa ataaaacaac atccgtaaag     120
ctaaataatt ttaaaaactc tgtcacttat t                                    151
```

<210> SEQ ID NO 485
<211> LENGTH: 166
<212> TYPE: DNA
<213> ORGANISM: Mus musculus

<400> SEQUENCE: 485

```
atttcttctg ggctttccag agttatggtc acaaacctct tatcagaggt gatcaaagac     60
cgtggttcaa agcttgatgc accagaaatg tgagctaagg ctgcagccaa cacatccact    120 accccttct cttctatcag tctttgagct gatggttgga aaaaat                    166
```

<210> SEQ ID NO 486
<211> LENGTH: 147
<212> TYPE: DNA
<213> ORGANISM: Mus musculus

<400> SEQUENCE: 486

```
gtaatgttcc cactgtgttt aatgttcttc tgcttcttcc tgtctctcgg tggctccttg     60
agggctttga tgatcagggc tgaggcagaa ggcaccacct cgatctgggc ctgtctgttc    120
tggatggtca gtttcactgt aattctg                                        147
```

<210> SEQ ID NO 487
<211> LENGTH: 211
<212> TYPE: DNA
<213> ORGANISM: Mus musculus

<400> SEQUENCE: 487

```
taataaatgc caacggcggc aacaggcccc cttggccgcc cctggagtac caaccctacc     60
agagcatcta tgtcggaggc atgatggtgg aaggggaggg caagagccct ctcctgcgaa    120
gccagagcac ttcagagcag gagaaacgcc taacctggcc tcgcaggtcc tactcgcctc    180
ggagtttcga ggacagcgga ggtggctaca c                                   211
```

<210> SEQ ID NO 488
<211> LENGTH: 167
<212> TYPE: DNA
<213> ORGANISM: Mus musculus

<400> SEQUENCE: 488

```
cacaagggct tcagggacca aggccaactc ctctaagtcc cctcagctcc tgccttcccc     60
ctcccttgcc agggacattt ggctcttcta agcaggctct gttcaccagg aggattcccc    120
tcttgccaag tttggtgcgc agagctacag atgggaccaa agggagt                  167
```

<210> SEQ ID NO 489
<211> LENGTH: 182
<212> TYPE: DNA
<213> ORGANISM: Mus musculus

<400> SEQUENCE: 489

```
gcctgtatag gcaggtacca gtaaatgtta aaagaatgaa gttactcctt gctcatcctt     60
cacctaccaa gctagagaca ggaaaaggcc cgtgccatta agagtctgtt cttgaaggca    120
gagaacagaa gagtgacctt cttctacccc ctaagacctg ggtcagtctc aaacagtcca    180
gt                                                                   182
```

```
<210> SEQ ID NO 490
<211> LENGTH: 170
<212> TYPE: DNA
<213> ORGANISM: Mus musculus

<400> SEQUENCE: 490
agcagcacac tcaaggacag gctcaaatgc tttcctctgc ctgggagttc aagcattcat      60
gaggaaaaaa aaaaatcaag agggatttta aaataaagcc catgctctct gcaggctgtc     120
tgctctgagc cagcgcagcc gtggggtgat tatggaggaa ggaatggttt                170

<210> SEQ ID NO 491
<211> LENGTH: 181
<212> TYPE: DNA
<213> ORGANISM: Mus musculus

<400> SEQUENCE: 491
tgtaaaaaag aaacacggtt tgttaggcag aaaccatcag ggtaggaaac aggcagacag      60
gacagggtaa agtaccaact gggcttttgt ccctcccccg atctcagtga ggacggagga     120
aggacatttt gtgctacagc agctgttttt gtactggtca gatgggtgt gagattttg      180 c                                                                    181

<210> SEQ ID NO 492
<211> LENGTH: 214
<212> TYPE: DNA
<213> ORGANISM: Mus musculus

<400> SEQUENCE: 492
acagtgcgtc ctaattacac actccgtcgt gacaggcggt gtcaaagatt aaaggaatca      60
aacccagggg ctctccagga cacccccac ctcaagaacc agagtgcgat tatggtacca     120
aggtagaagt taggaagata attttccctg gtccaagct gcatgtcagc atcttgtctc     180
agctaccttg tctgggctcc tcgggttcat ttgc                                214

<210> SEQ ID NO 493
<211> LENGTH: 163
<212> TYPE: DNA
<213> ORGANISM: Mus musculus

<400> SEQUENCE: 493
ctccgcaagg tgaggccggg agcctgggag tcaggggtgc agggacccaa gctaggatgc      60
gccgtggcca ctcacaggca tccccatccc ttggcaggtg ggctccttg atccctacag     120 cgatgatccg cggctaggca tccagaagat tttcctctgc aaa                      163

<210> SEQ ID NO 494
<211> LENGTH: 195
<212> TYPE: DNA
<213> ORGANISM: Mus musculus

<400> SEQUENCE: 494
cacttgatga gcagaagtcc agtgtggtgc tgatctgggt cagtcattca caagagacca      60
ctgcactttg atgtggattt tgtagggggg aggggtaaag aaccagtttt gtcaacaggt     120
actgatgatc acaggcagtt gctattatta ggactcaaat tttgctttct ttgacactgg     180
tagtgtgtct tcctt                                                     195

<210> SEQ ID NO 495
<211> LENGTH: 187
<212> TYPE: DNA
```

<213> ORGANISM: Mus musculus

<400> SEQUENCE: 495

| | |
|---|---|
| gagtcaaaaa aaataactat atatcatttt aaattgctct ggctggtacc tctgcatttt | 60 |
| aaggatatca aggtggggga aatgtgctta atgacaggac tacacgtgga taaagggctg | 120 |
| acagggtgat tgcgatacca ggtgctccca cacaccgtt agcttcttcc tttctgggcc | 180 |
| tccgaag | 187 |

<210> SEQ ID NO 496
<211> LENGTH: 200
<212> TYPE: DNA
<213> ORGANISM: Mus musculus

<400> SEQUENCE: 496

| | |
|---|---|
| ctcagtgttt agaataaagc cagattgttt tcaggcccag ttccgcggca gagtttgtat | 60 |
| gcacggcaat ctcaaacatt cctcgttcc ctctaaaggc aaagccaatc tcatttgaaa | 120 |
| tggaggttag agtaaaaaaa aatcacttct gtgttttacc accttctgcg ctaagtatta | 180 |
| tctcaacaac cttttgctct | 200 |

<210> SEQ ID NO 497
<211> LENGTH: 181
<212> TYPE: DNA
<213> ORGANISM: Mus musculus

<400> SEQUENCE: 497

| | |
|---|---|
| gcggtatagg gaagggagt ttcaggacaa aaggccagca cacaagagct ttacccaggt | 60 |
| acttagagac agagtggagg ggcgctctga ctgctactta cacaagtcct cggatgacag | 120 |
| atcagattcc tgaggtctgg aaagtgttac ataccattat tctaaacaag gctatgagat | 180 |
| a | 181 |

<210> SEQ ID NO 498
<211> LENGTH: 142
<212> TYPE: DNA
<213> ORGANISM: Mus musculus

<400> SEQUENCE: 498

| | |
|---|---|
| aagaaaggtc tcattgatta tgacaccttc aaggagctat gtgaacaaga gtgcgaatgg | 60 |
| gaagaaataa ccatcacagg atcagacggc tccaccaggg tggtcttagt ggacaggaag | 120 |
| accggcagtc agtatgacat tc | 142 |

<210> SEQ ID NO 499
<211> LENGTH: 161
<212> TYPE: DNA
<213> ORGANISM: Mus musculus

<400> SEQUENCE: 499

| | |
|---|---|
| gcacatcctt tgtatcatga aataaaacag ggccctcaag aaaagtaact ccatatgcag | 60 |
| ccctgccctc ttagggcgcc gaggaaggct ggagccttgg cactctgtgt ggtggtggct | 120 |
| ccctttctct ttctttcctt tcctgtgaca agcagccatt g | 161 |

<210> SEQ ID NO 500
<211> LENGTH: 214
<212> TYPE: DNA
<213> ORGANISM: Mus musculus

<400> SEQUENCE: 500

```
cgctgaatgc cttctcaggc agcagggagt tgctcacgga tgtagtgtcc tgaagcagca        60
gctcctgctc tggggcgcta ttgcgctgtc catagaggtc ggtgcccacc gccaggagcc       120
gcccagcgga acccaccacg gtcacgtcct gcttgaactc tccaggcaca ttgaagttca       180
gggtaacggt gcagcacact ccaccctcca gcac                                   214

<210> SEQ ID NO 501
<211> LENGTH: 161
<212> TYPE: DNA
<213> ORGANISM: Mus musculus

<400> SEQUENCE: 501
gagtgcaggc cgccaccacc catcaggtcg tcgcagctcc agttgtattt cttgcccagc        60
agactaccgc tgtgcacctg cacctcgcac accagcagct cgcccacgta gccctcctca       120
atcagctgct tcatgcgtac gaaggctggg aggaagcgca g                          161

<210> SEQ ID NO 502
<211> LENGTH: 139
<212> TYPE: DNA
<213> ORGANISM: Mus musculus

<400> SEQUENCE: 502
tttcccaccc cgaggaggac gaagcagagg tcagtactag tggctttgta catgaatgga        60 ccttccctc catcccctt cacatgtggt ccagcaacag taacagacag atgcgacaca        120
aaaagagaca cacctgatt                                                   139

<210> SEQ ID NO 503
<211> LENGTH: 191
<212> TYPE: DNA
<213> ORGANISM: Mus musculus

<400> SEQUENCE: 503
ggttgggggg gaggcactaa acaaaaggaa ccacaggcct gtttactaga gagaaggctt        60
aattggcttc agagaaagtg caggaagtgt gtgggtttgc tgctctcgtt tgtcggggc       120 cccagtgaaa ggctggaagg gacagagatt ctggctcccc ccagccccga ctgtctggcc      180
cctccctctc t                                                          191

<210> SEQ ID NO 504
<211> LENGTH: 148
<212> TYPE: DNA
<213> ORGANISM: Mus musculus

<400> SEQUENCE: 504
aatagaacag taacggcaca cagagagatg gccaatgaga gcagctttca gtgatgtcat        60
acttatacct gcttcttatt atttgctgaa tggtaacaat gtgtgccttt aatcttacat       120
ttcattggtt aaaagccctg ccattcta                                          148

<210> SEQ ID NO 505
<211> LENGTH: 193
<212> TYPE: DNA
<213> ORGANISM: Mus musculus

<400> SEQUENCE: 505
gaatcgtgct gggttgtgtg atatgatttg gagaagagaa ctgactgccc taaaatgaaa        60
aagacgaagt aattttccat aggcttttga atcctaaggt ttaccctcct gttcccccta      120
```

```
tcgtccatct aaagattaaa gagtgaaaca atcagcggat tttaaagtga aggggaaggg    180
agggtggtct gca                                                       193

<210> SEQ ID NO 506
<211> LENGTH: 178
<212> TYPE: DNA
<213> ORGANISM: Mus musculus

<400> SEQUENCE: 506
taatagtgtt agtgtaaacc taccctaaag ggtcagactt gctaatacac atgtaatcct    60
ttccatggaa gatcatctcc cttgagaaaa ctatccaatc atgaaaggta atgaagactt    120
gcagcaaagg tctgacactg aatatggaat aagtggagga tgaggtagct aggttttg     178

<210> SEQ ID NO 507
<211> LENGTH: 126
<212> TYPE: DNA
<213> ORGANISM: Mus musculus

<400> SEQUENCE: 507
cttaaaaaca tggaggacga tgtcctgcag gaggttaccc cagtcacaag gctgcgagcg    60
ctcctgtgtc gtcctcggtc tcttgggctt ctcggcagtg ccttcctcag cagagtcctg    120
gtcact                                                               126

<210> SEQ ID NO 508
<211> LENGTH: 147
<212> TYPE: DNA
<213> ORGANISM: Mus musculus

<400> SEQUENCE: 508
aacactcctc ttgaactcct gccagaatcc cggagctgaa gctcccctgc gtggcagagc    60
tgacctatgc tctcaaagcc taattaattt gcagaggaat gtcaaaatga caggtccacc    120
acctgcttca cttgacactt aaaagga                                        147

<210> SEQ ID NO 509
<211> LENGTH: 214
<212> TYPE: DNA
<213> ORGANISM: Mus musculus

<400> SEQUENCE: 509
cgagaggacc tactgtcgcc ggtgcaggac gctgatcgct tttacagggg catttagag    60 ccagacaaac actgctccac taccctgcg ggcagcagcc tcccagaata ccctaaattc    120
ccatgcagcc cggctgctta cactttctcc ccaaactatg acctgcgacg cccccatcag    180
tatttgcacc cgggtgcagg ggagagcagg ctgc                                214

<210> SEQ ID NO 510
<211> LENGTH: 153
<212> TYPE: DNA
<213> ORGANISM: Mus musculus

<400> SEQUENCE: 510
agggatttca taacaaggaa ccagtgtgca cgccaaaggc tgttgctggt tgactagtgg    60
ttttggcggc tggtcctggg cagttgctgc catctgttcc ataaaactgt tttttagaaa    120
gatatataaa acaattaaca agtcagaatt cta                                 153

<210> SEQ ID NO 511
<211> LENGTH: 145
```

```
<212> TYPE: DNA
<213> ORGANISM: Mus musculus

<400> SEQUENCE: 511
aaagaatatc tcagtagcca atatttttct ctgctggtat caaatgaaat tcatttggta    60
tcagctggag tttttatagt gctaatggaa gttattttca gttatcacgt cagtctgtaa   120
gtatacaaag gcggcaattt cgctg                                         145

<210> SEQ ID NO 512
<211> LENGTH: 187
<212> TYPE: DNA
<213> ORGANISM: Mus musculus

<400> SEQUENCE: 512
tctcatcagg accacagtag ggcagcttga tggtgagtga ggtgagagat atggaatgga    60
tggtcccccc tgtccatagg gctgctgcca gcatcataca caccttccag ttcattattg   120
tcatatactg caaaggttta caaatagcca catagcgatc ataggccatg acagtaagaa   180
ggaagat                                                             187

<210> SEQ ID NO 513
<211> LENGTH: 189
<212> TYPE: DNA
<213> ORGANISM: Mus musculus

<400> SEQUENCE: 513
gagacatctg gaagagagag ccatgaggca ttaatgtgct tggtggtagg aagaattggg    60
agatggtaca aaaaaagag atgggattgt ggcacccaat gtcactggtg actccttgaa   120
aatggaaaat attagtgaaa attctgttgg tgccacccct tgatcagcat ttatctcatc   180
ccaggttct                                                           189

<210> SEQ ID NO 514
<211> LENGTH: 137
<212> TYPE: DNA
<213> ORGANISM: Mus musculus

<400> SEQUENCE: 514
agcttatgcc cccacccct gcaacatttg gctccttggg atctctgagt caccctctga    60
ccttgaccgt ctgtaggaag ggcctacact cgttgagcca acctcatcca agagggctta   120
ataagcactt ggcggct                                                  137

<210> SEQ ID NO 515
<211> LENGTH: 162
<212> TYPE: DNA
<213> ORGANISM: Mus musculus

<400> SEQUENCE: 515
attggtctag ccgtcacatg gtgaggaccg aatgcgcgga taattatgga gctgatattt    60 ccccctccc cttctttttc ctcccgcccc tccaaccgct cccccccct tcccggatgg   120 gggaaaaaag atgtcagctc ctccgctgta gtattgctcc tt                     162

<210> SEQ ID NO 516
<211> LENGTH: 207
<212> TYPE: DNA
<213> ORGANISM: Mus musculus

<400> SEQUENCE: 516
```

```
ccagtggatt tgaattcggg gggaatttcc caaactgaca atcctctagg gccttagaga    60
gcttcttcct attcttccac ccttgggatt ttctatcccc tgttcttcta aggagaggga   120
aggcaagtgt ggggaaggag agcctcagcc tgctcacacc ctgtggcttg caagtccccc   180
tcagtgctgc ctttgtctcc acaggtg                                       207

<210> SEQ ID NO 517
<211> LENGTH: 199
<212> TYPE: DNA
<213> ORGANISM: Mus musculus

<400> SEQUENCE: 517
atttttatca atctcaccaa ggatgaattt gcgtgagtac aggccagcat gtgccatccc    60
cgaaactctt atccaagcct tccccccccc ccttatcttt tagtcctacc ccttgctgaa   120
aggactggtc tcttctctgt tgtccactt agagagctgc gggccctggt tatcgagatg    180
gtgttggcca cagacatgt                                                199

<210> SEQ ID NO 518
<211> LENGTH: 203
<212> TYPE: DNA
<213> ORGANISM: Mus musculus

<400> SEQUENCE: 518
aacatcactt tagtaaattg tgattttttt aaaaaagcc atgatttatt gatgtgagtg    60
gcttgttttc atgtggcgcc agaaatgaac ctgtttaaaa gctataacca atggtactga   120
tctatccatt aaatactgtc cttaaactgt agtttaatag tattgtcaac taggaaagct   180
aaaatggttt tgttctgtt gaa                                            203

<210> SEQ ID NO 519
<211> LENGTH: 150
<212> TYPE: DNA
<213> ORGANISM: Mus musculus

<400> SEQUENCE: 519
cctccctact catcctttgg gcaaacagtc cagaaagccg aggttgccaa gacgcaaaag    60
gaacagtggg gggtggggca cgttccttgc ttctcttgcc ccctggtttc cttttatttt   120
caggggtgga gggagggca cttgtctcga                                     150

<210> SEQ ID NO 520
<211> LENGTH: 191
<212> TYPE: DNA
<213> ORGANISM: Mus musculus

<400> SEQUENCE: 520
tcatatcttt cagtctccac ttgtgtgggg gaggtggggg cgggacaccc tccttttctc    60
ttgaccccgg ggcttctgct cttcctcatt ggaaggaggg tggtggcctg gtgagaggcc   120
cctgcctcgg agcgcctctc ttcagagaac tacctgccgc ccattgtggg ctggccagga   180
agcccggctt t                                                        191

<210> SEQ ID NO 521
<211> LENGTH: 124
<212> TYPE: DNA
<213> ORGANISM: Mus musculus

<400> SEQUENCE: 521
tctaattatt gggcttaaat tgcattagtg tgctggcaat ttgtctaccc ctggaaaagt    60
```

```
aattgacatt tgggttactg cttcatatgt gggcgacttg ctagccagtt ccaaagagtc    120
ctct                                                                 124
```

<210> SEQ ID NO 522
<211> LENGTH: 155
<212> TYPE: DNA
<213> ORGANISM: Mus musculus

<400> SEQUENCE: 522

```
acatggtcct aaggatctat cgactctggg cacacgagaa gattgatcaa tccggcagac    60
tcacattaat tgtgaaatag aaaggaacgg tgcgatcaat ggtgaggatg aaagtccgcc    120
cgatgttgcc acatccagct aatccgataa tgaag                               155
```

<210> SEQ ID NO 523
<211> LENGTH: 157
<212> TYPE: DNA
<213> ORGANISM: Mus musculus

<400> SEQUENCE: 523

```
ctacagcaaa aaattcacaa agcctccccc cccccaaaa aaaaagaga gtagaggtgg       60 ggggagggga gagagacttc ttccccagtt ccctcactga ggaagttgtt ggttggctga    120
atgctgaagc agttccaccg cataattttt tttctgt                             157
```

<210> SEQ ID NO 524
<211> LENGTH: 199
<212> TYPE: DNA
<213> ORGANISM: Mus musculus

<400> SEQUENCE: 524

```
cagtggtctg atggaagcag ctcccagttc cggtaagcta tgactggatt ccgaagtgtt    60
aatttgaacc ctgctggagt cagtgtggca caagaaaagc tatgatacat attgctaagt    120
gtccccatgg gtctctattt gtagaaactg gtacactgat gaaccttctt gtgggagtga    180
aaaatgtgta gtcatgtac                                                 199
```

<210> SEQ ID NO 525
<211> LENGTH: 185
<212> TYPE: DNA
<213> ORGANISM: Mus musculus

<400> SEQUENCE: 525

```
attgggtagc gtaatggaga ctgtggcaat gtgccaaccg aggagtcaat gggaaaggaa    60
taagaggcat aatgagttat gtggagaaag gagcaggtgg gccaagaaaa ttggacacca    120
cgaggactct gtaaaatcaa gtgattgaat tatagctcta aggagatgta taatgggaat    180
cactg                                                                185
```

<210> SEQ ID NO 526
<211> LENGTH: 136
<212> TYPE: DNA
<213> ORGANISM: Mus musculus

<400> SEQUENCE: 526

```
ttcacagaag tatgcctcct tgtctaatct gagaagccat tggcgggaga ttgatgggca    60
gttacagaga agtgtttcag gaggcggctg tatgctcaga ggtaccagaa tagagctatc    120
tgtcttcatt gaaccc                                                    136
```

<210> SEQ ID NO 527
<211> LENGTH: 150
<212> TYPE: DNA
<213> ORGANISM: Mus musculus

<400> SEQUENCE: 527
agccaccagc ttcctgtgcg gggccaatgg gacaggcttc agttatctaa gacaattaat    60
tcatttggtg ccaactcctg tggccgttaa ttgttcagcg tttccatgtt caggaactcc   120
tccccgcgga ctggctgcct gtgacgtcac                                    150

<210> SEQ ID NO 528
<211> LENGTH: 194
<212> TYPE: DNA
<213> ORGANISM: Mus musculus

<400> SEQUENCE: 528
gaatgttggc atggtgtagg aaacaaaagt caacttaaca accaaaaagt tagttcctgc    60
aggaaagatg gctatgggtc ctgggacaca cacacacaca cacacacaca cacacaaag   120 ggttgatgag gttgattgca ctaagtgact gctaaaggcc ctggtgtgtc ttggacttgc   180
agcctttgtc tgca                                                     194

<210> SEQ ID NO 529
<211> LENGTH: 188
<212> TYPE: DNA
<213> ORGANISM: Mus musculus

<400> SEQUENCE: 529
cacacagatt ggtatcttca aaaggccaa cctggtaggc ctcacttgcc tcctgcaaag    60
caccaatagc tgcactctgg aagcgcagat ctgttttgaa gtcctgagca atttctcgca   120
ccagacgctg aaaggggagc ttgcggatca gaagttcagt ggacttctga tagcgtctga   180
tttcacgg                                                            188

<210> SEQ ID NO 530
<211> LENGTH: 172
<212> TYPE: DNA
<213> ORGANISM: Mus musculus

<400> SEQUENCE: 530
caggtggctc cattcctgca cggcttatgg tgagtacagt agttcaggtc tgcccgggtg    60
gagacaggaa aggggacagg aagcccaagg tcaaatacag gaaggatcta tgtttccagt   120
gggcattggg ctgctttgag gagacctggc aatcttagag gagggcctta cc           172

<210> SEQ ID NO 531
<211> LENGTH: 203
<212> TYPE: DNA
<213> ORGANISM: Mus musculus

<400> SEQUENCE: 531
tactgtggag ctgtggcaaa gagacaggag agaaggggg tggagccgca tcagggtcgg    60
ggcactcctg ctttgccttt caaagaaacc caggagctat tacttagtcc tctgacgcag   120
gatagtcctg ggttggttgc cacagcagag agtggcagcc tttctgccag cacttctgtt   180
tcagattcat cccagaaaaa aga                                           203

<210> SEQ ID NO 532
<211> LENGTH: 208

```
<212> TYPE: DNA
<213> ORGANISM: Mus musculus

<400> SEQUENCE: 532
tttgagcaac agacagcaga gctactgcta ctgtggaggc cctggagagt gagtggagag      60
ggtgttgtca agctatggga tgggggttgt tgtggtggca gagcccggga aaatgggtga     120 acaggggggcg aggggggccct gtggtttcaa gaaggctgtc tgagggccac aagcgctgtc    180
tcccctccag gtggaacctg aaaatgct                                        208

<210> SEQ ID NO 533
<211> LENGTH: 187
<212> TYPE: DNA
<213> ORGANISM: Mus musculus

<400> SEQUENCE: 533
cagctgaccc atctggagct ggacgaagag gttctgcaga atgttctgga attgcctacc      60
tggctggcca tcactagggt ctactgcaat cgggcctcca tccaggtgag agtggggtct     120
gagcactgtg cgtcccgagc cagcaggctt gttcacttaa ggagcggctg tcacaggcct     180
gcatctg                                                               187

<210> SEQ ID NO 534
<211> LENGTH: 133
<212> TYPE: DNA
<213> ORGANISM: Mus musculus

<400> SEQUENCE: 534
aaatggatgt gctgctgccc cagcggagct cagacaggat gaaatggaag caggatgagg      60
ctgcaggcgg ccttcctggt gccgatgcca gtaccggtgc ctgcctcctg agctcagtca     120
tctgcaggac ccg                                                        133

<210> SEQ ID NO 535
<211> LENGTH: 200
<212> TYPE: DNA
<213> ORGANISM: Mus musculus

<400> SEQUENCE: 535
agcaacctac agagccggcc ggagaccctc tgccttcata gttataggtg aggacatagt      60
cttgggatgg gatgtggtct tcattctgat tacacacatg caatttctgt aaagtccaaa     120
aaagaggatt gtattatttt tttaaaacaa cttcaacata tgaacagaaa atttattta     180 tttacctttt atgtttaatt                                                 200

<210> SEQ ID NO 536
<211> LENGTH: 157
<212> TYPE: DNA
<213> ORGANISM: Mus musculus

<400> SEQUENCE: 536
aatgaaacac cttacatatc acttcatctg gagagcctga attgacagca gcgggtgtaa      60
tttatacatc ctttcccccc atctgttagc attcagtctt caggctgtcc tgtgtgtgtg     120
tgtgtgtgtg tgtgtgtgtg tgtttcttca attctct                              157

<210> SEQ ID NO 537
<211> LENGTH: 145
<212> TYPE: DNA
<213> ORGANISM: Mus musculus
```

```
<400> SEQUENCE: 537
atagtccctg attcttcttt caatgagtct gcagaggaga gagagactgc ctgaagattg       60
tgcacctcag ccttcccctt cctacggagc acgactcttc cctgcagcta gctagctctc      120
ctttcttttc aggctggcct gtcct                                            145

<210> SEQ ID NO 538
<211> LENGTH: 136
<212> TYPE: DNA
<213> ORGANISM: Mus musculus

<400> SEQUENCE: 538
aggatcttgt ttcctcagct cattgaaaat agaaagggct ttgtcgatat ctgcagaaag       60
aaagcagagt ctaaaaccca tctaactgca cctctgcctc tgtcagcatc cagggtcctt      120
agtcactcac ctctga                                                      136

<210> SEQ ID NO 539
<211> LENGTH: 217
<212> TYPE: DNA
<213> ORGANISM: Mus musculus

<400> SEQUENCE: 539
ggccgcggcc catggagctg taggagccgc ggtaggtagc ggagggcagg tggtgctggg       60
gcctcggggc gggcaccgcg accgtccctc cctctctccc atcccccagt ccagccgctg      120
gtgcggcgga gcctcctagg ccgtctcggc gggagaaccc gggacccggt ggggaggggg      180
gtggcggagt gcatgtccca gaccctcccc atccct                                217

<210> SEQ ID NO 540
<211> LENGTH: 158
<212> TYPE: DNA
<213> ORGANISM: Mus musculus

<400> SEQUENCE: 540
catactctat tgtattattt ggagttaaat cctcactttg ggggaggggg gagcaaagcc       60
aagcaaacca atgatgatcc tctattttgt gatgactctg ctgtgacatt aggtttgaag      120 cattttttttt ttcaagcagc agtcctaggt attaactg                             158

<210> SEQ ID NO 541
<211> LENGTH: 161
<212> TYPE: DNA
<213> ORGANISM: Mus musculus

<400> SEQUENCE: 541
tcaataggga ataacaaga tgtcacttca ataactctt ccacgaaagg tcctgcggca        60
acagagaaag gataaagttg acttgggctc attacctctg agcagcttca accagctaat      120
tcagtgctat gaaaacctac ccagactgta gtccttggag a                          161

<210> SEQ ID NO 542
<211> LENGTH: 202
<212> TYPE: DNA
<213> ORGANISM: Mus musculus

<400> SEQUENCE: 542 ctgtccccttt ttgacaccat tcctgattca gagctgctcg tgtccctcg ggagagctcc       60 tctgtgagta tggcatcagg gagggataca gggctagtcc gaaggttcca accacgtccg      120
ggagcctcta catatagctg tgcacaaact gatcggggcc tttcttcctc tcagctgcac      180
```

```
aagctgctca atctctctcg ga                                              202

<210> SEQ ID NO 543
<211> LENGTH: 199
<212> TYPE: DNA
<213> ORGANISM: Mus musculus

<400> SEQUENCE: 543
ccttcaggta agtgggaggg gagaacaacc aggctaatgg ccaagagctc gtaggccggc      60
tctacttgct gggtcagccg gcagcagtgt gaagctcgta ggccggctct acttgctggg     120
tcagccggca gcagcgtgaa gctgtgcttt gattccactg aggctttaga gactcactgt     180
ttccaaacaa ggagctcgg                                                  199

<210> SEQ ID NO 544
<211> LENGTH: 185
<212> TYPE: DNA
<213> ORGANISM: Mus musculus

<400> SEQUENCE: 544 gccctcca tggaggtttg ccaggtgcct ccagtgagaa gggccggaag acctatccta       60
ctgtcaaggt gagctcagat gacaccggag ggtagggatg gtgtatgggg caactactga    120
ctatcctttg ccattctcag atctgtaact atgagggacc ggccaagatt gaggtggacc    180
tggtg                                                                 185

<210> SEQ ID NO 545
<211> LENGTH: 22
<212> TYPE: DNA
<213> ORGANISM: Artificial Sequence
<220> FEATURE:
<223> OTHER INFORMATION: synthetic

<400> SEQUENCE: 545
ctgcatgtag gcctttgagg at                                               22

<210> SEQ ID NO 546
<211> LENGTH: 22
<212> TYPE: DNA
<213> ORGANISM: Artificial Sequence
<220> FEATURE:
<223> OTHER INFORMATION: synthetic

<400> SEQUENCE: 546
gggcccatgt gaaaagcata ac                                               22

<210> SEQ ID NO 547
<211> LENGTH: 18
<212> TYPE: DNA
<213> ORGANISM: Artificial Sequence
<220> FEATURE:
<223> OTHER INFORMATION: synthetic

<400> SEQUENCE: 547
gccggcaact ctgactcc                                                    18

<210> SEQ ID NO 548
<211> LENGTH: 20
<212> TYPE: DNA
<213> ORGANISM: Artificial Sequence
<220> FEATURE:
<223> OTHER INFORMATION: synthetic
```

<400> SEQUENCE: 548
tcaccagtct gaaccccact                                                  20

<210> SEQ ID NO 549
<211> LENGTH: 18
<212> TYPE: DNA
<213> ORGANISM: Artificial Sequence
<220> FEATURE:
<223> OTHER INFORMATION: synthetic

<400> SEQUENCE: 549
ccgacgggtg tggatgtg                                                    18

<210> SEQ ID NO 550
<211> LENGTH: 22
<212> TYPE: DNA
<213> ORGANISM: Artificial Sequence
<220> FEATURE:
<223> OTHER INFORMATION: synthetic

<400> SEQUENCE: 550
cgagaaggcc aaccactact ac                                               22

<210> SEQ ID NO 551
<211> LENGTH: 23
<212> TYPE: DNA
<213> ORGANISM: Artificial Sequence
<220> FEATURE:
<223> OTHER INFORMATION: synthetic

<400> SEQUENCE: 551
atcaatgaaa cgaccgtcct ctt                                              23

<210> SEQ ID NO 552
<211> LENGTH: 28
<212> TYPE: DNA
<213> ORGANISM: Artificial Sequence
<220> FEATURE:
<223> OTHER INFORMATION: synthetic

<400> SEQUENCE: 552
acggttacca gaaaagaggt atagaatt                                         28

<210> SEQ ID NO 553
<211> LENGTH: 22
<212> TYPE: DNA
<213> ORGANISM: Artificial Sequence
<220> FEATURE:
<223> OTHER INFORMATION: synthetic

<400> SEQUENCE: 553
tgagtagctc agggatgctg ta                                               22

<210> SEQ ID NO 554
<211> LENGTH: 18
<212> TYPE: DNA
<213> ORGANISM: Artificial Sequence
<220> FEATURE:
<223> OTHER INFORMATION: synthetic

<400> SEQUENCE: 554
cccacggagc tgccattt                                                    18

<210> SEQ ID NO 555
<211> LENGTH: 22

-continued

```
<212> TYPE: DNA
<213> ORGANISM: Artificial Sequence
<220> FEATURE:
<223> OTHER INFORMATION: synthetic

<400> SEQUENCE: 555
cccactaatt ctgcagatgg ct                                              22

<210> SEQ ID NO 556
<211> LENGTH: 19
<212> TYPE: DNA
<213> ORGANISM: Artificial Sequence
<220> FEATURE:
<223> OTHER INFORMATION: synthetic

<400> SEQUENCE: 556
gcctggctac ggttcagac                                                  19

<210> SEQ ID NO 557
<211> LENGTH: 21
<212> TYPE: DNA
<213> ORGANISM: Artificial Sequence
<220> FEATURE:
<223> OTHER INFORMATION: synthetic

<400> SEQUENCE: 557
cgggctctga gttgattcct c                                               21

<210> SEQ ID NO 558
<211> LENGTH: 24
<212> TYPE: DNA
<213> ORGANISM: Artificial Sequence
<220> FEATURE:
<223> OTHER INFORMATION: synthetic

<400> SEQUENCE: 558
aaacccatgt cccacatttt caac                                            24

<210> SEQ ID NO 559
<211> LENGTH: 19
<212> TYPE: DNA
<213> ORGANISM: Artificial Sequence
<220> FEATURE:
<223> OTHER INFORMATION: synthetic

<400> SEQUENCE: 559
gcaatggagg tcccttggg                                                  19

<210> SEQ ID NO 560
<211> LENGTH: 18
<212> TYPE: DNA
<213> ORGANISM: Artificial Sequence
<220> FEATURE:
<223> OTHER INFORMATION: synthetic

<400> SEQUENCE: 560
atggagggcc tggaggtc                                                   18

<210> SEQ ID NO 561
<211> LENGTH: 20
<212> TYPE: DNA
<213> ORGANISM: Artificial Sequence
<220> FEATURE:
<223> OTHER INFORMATION: synthetic

<400> SEQUENCE: 561
```

```
tcaccactcc agcccaagta                                              20

<210> SEQ ID NO 562
<211> LENGTH: 21
<212> TYPE: DNA
<213> ORGANISM: Artificial Sequence
<220> FEATURE:
<223> OTHER INFORMATION: synthetic

<400> SEQUENCE: 562
gccagtacct tcctgcatct c                                            21

<210> SEQ ID NO 563
<211> LENGTH: 23
<212> TYPE: DNA
<213> ORGANISM: Artificial Sequence
<220> FEATURE:
<223> OTHER INFORMATION: synthetic

<400> SEQUENCE: 563
actacaccag ctgggaaaca att                                          23

<210> SEQ ID NO 564
<211> LENGTH: 19
<212> TYPE: DNA
<213> ORGANISM: Artificial Sequence
<220> FEATURE:
<223> OTHER INFORMATION: synthetic

<400> SEQUENCE: 564
tgggaggaca agagtggca                                               19

<210> SEQ ID NO 565
<211> LENGTH: 20
<212> TYPE: DNA
<213> ORGANISM: Artificial Sequence
<220> FEATURE:
<223> OTHER INFORMATION: synthetic

<400> SEQUENCE: 565
cccgtgtgtg ttaggggatg                                              20

<210> SEQ ID NO 566
<211> LENGTH: 17
<212> TYPE: DNA
<213> ORGANISM: Artificial Sequence
<220> FEATURE:
<223> OTHER INFORMATION: synthetic

<400> SEQUENCE: 566
cggcgcacat acctgct                                                 17

<210> SEQ ID NO 567
<211> LENGTH: 26
<212> TYPE: DNA
<213> ORGANISM: Artificial Sequence
<220> FEATURE:
<223> OTHER INFORMATION: synthetic

<400> SEQUENCE: 567
taagatcaaa cacatcagca atgagc                                       26

<210> SEQ ID NO 568
<211> LENGTH: 26
<212> TYPE: DNA
<213> ORGANISM: Artificial Sequence
```

```
<220> FEATURE:
<223> OTHER INFORMATION: synthetic

<400> SEQUENCE: 568
gcaaccaaag tttttctttc tttccc                                              26

<210> SEQ ID NO 569
<211> LENGTH: 20
<212> TYPE: DNA
<213> ORGANISM: Artificial Sequence
<220> FEATURE:
<223> OTHER INFORMATION: synthetic

<400> SEQUENCE: 569
agccttgcat attggtgggg                                                     20

<210> SEQ ID NO 570
<211> LENGTH: 26
<212> TYPE: DNA
<213> ORGANISM: Artificial Sequence
<220> FEATURE:
<223> OTHER INFORMATION: synthetic

<400> SEQUENCE: 570
ctctctactg acttaaggat tgtggg                                              26

<210> SEQ ID NO 571
<211> LENGTH: 22
<212> TYPE: DNA
<213> ORGANISM: Artificial Sequence
<220> FEATURE:
<223> OTHER INFORMATION: synthetic

<400> SEQUENCE: 571
ctccaatcag cttcagggag ac                                                  22

<210> SEQ ID NO 572
<211> LENGTH: 19
<212> TYPE: DNA
<213> ORGANISM: Artificial Sequence
<220> FEATURE:
<223> OTHER INFORMATION: synthetic

<400> SEQUENCE: 572
gcgacagacc ctgctcttc                                                      19

<210> SEQ ID NO 573
<211> LENGTH: 18
<212> TYPE: DNA
<213> ORGANISM: Artificial Sequence
<220> FEATURE:
<223> OTHER INFORMATION: synthetic

<400> SEQUENCE: 573
ccaccacctg gctctcct                                                       18

<210> SEQ ID NO 574
<211> LENGTH: 19
<212> TYPE: DNA
<213> ORGANISM: Artificial Sequence
<220> FEATURE:
<223> OTHER INFORMATION: synthetic

<400> SEQUENCE: 574
aggacctgta ccacgccat                                                      19
```

<210> SEQ ID NO 575
<211> LENGTH: 20
<212> TYPE: DNA
<213> ORGANISM: Artificial Sequence
<220> FEATURE:
<223> OTHER INFORMATION: synthetic

<400> SEQUENCE: 575
agccacagag gagatcagct                                              20

<210> SEQ ID NO 576
<211> LENGTH: 29
<212> TYPE: DNA
<213> ORGANISM: Artificial Sequence
<220> FEATURE:
<223> OTHER INFORMATION: synthetic

<400> SEQUENCE: 576
agtacagagc tctcaaaaat gtacatttc                                    29

<210> SEQ ID NO 577
<211> LENGTH: 19
<212> TYPE: DNA
<213> ORGANISM: Artificial Sequence
<220> FEATURE:
<223> OTHER INFORMATION: synthetic

<400> SEQUENCE: 577
gagagcacag acaaccccg                                               19

<210> SEQ ID NO 578
<211> LENGTH: 23
<212> TYPE: DNA
<213> ORGANISM: Artificial Sequence
<220> FEATURE:
<223> OTHER INFORMATION: synthetic

<400> SEQUENCE: 578
ctcgtgttgt atttccccca gat                                          23

<210> SEQ ID NO 579
<211> LENGTH: 22
<212> TYPE: DNA
<213> ORGANISM: Artificial Sequence
<220> FEATURE:
<223> OTHER INFORMATION: synthetic

<400> SEQUENCE: 579
ccattgatgg gttccatttg cc                                           22

<210> SEQ ID NO 580
<211> LENGTH: 16
<212> TYPE: DNA
<213> ORGANISM: Artificial Sequence
<220> FEATURE:
<223> OTHER INFORMATION: synthetic

<400> SEQUENCE: 580
gaccacgttc cgcggg                                                  16

<210> SEQ ID NO 581
<211> LENGTH: 22
<212> TYPE: DNA
<213> ORGANISM: Artificial Sequence
<220> FEATURE:
<223> OTHER INFORMATION: synthetic

```
<400> SEQUENCE: 581
tggaggatag gaacaccatc ga                                               22

<210> SEQ ID NO 582
<211> LENGTH: 24
<212> TYPE: DNA
<213> ORGANISM: Artificial Sequence
<220> FEATURE:
<223> OTHER INFORMATION: synthetic

<400> SEQUENCE: 582
acacacacct tgttgatgaa gaga                                             24

<210> SEQ ID NO 583
<211> LENGTH: 18
<212> TYPE: DNA
<213> ORGANISM: Artificial Sequence
<220> FEATURE:
<223> OTHER INFORMATION: synthetic

<400> SEQUENCE: 583
gcatggaagc cctggacc                                                    18

<210> SEQ ID NO 584
<211> LENGTH: 22
<212> TYPE: DNA
<213> ORGANISM: Artificial Sequence
<220> FEATURE:
<223> OTHER INFORMATION: synthetic

<400> SEQUENCE: 584
ccctgatgta cctcaaaggc tc                                               22

<210> SEQ ID NO 585
<211> LENGTH: 21
<212> TYPE: DNA
<213> ORGANISM: Artificial Sequence
<220> FEATURE:
<223> OTHER INFORMATION: synthetic

<400> SEQUENCE: 585
cccaggatgc caatgatcac a                                                21

<210> SEQ ID NO 586
<211> LENGTH: 23
<212> TYPE: DNA
<213> ORGANISM: Artificial Sequence
<220> FEATURE:
<223> OTHER INFORMATION: synthetic

<400> SEQUENCE: 586
agtccatttc tccttgcaga tcc                                              23

<210> SEQ ID NO 587
<211> LENGTH: 20
<212> TYPE: DNA
<213> ORGANISM: Artificial Sequence
<220> FEATURE:
<223> OTHER INFORMATION: synthetic

<400> SEQUENCE: 587
gggacaggga gtatcaggct                                                  20

<210> SEQ ID NO 588
```

```
<211> LENGTH: 24
<212> TYPE: DNA
<213> ORGANISM: Artificial Sequence
<220> FEATURE:
<223> OTHER INFORMATION: synthetic

<400> SEQUENCE: 588
ctctctcaga cttgctcact gatc                                            24

<210> SEQ ID NO 589
<211> LENGTH: 16
<212> TYPE: DNA
<213> ORGANISM: Artificial Sequence
<220> FEATURE:
<223> OTHER INFORMATION: synthetic

<400> SEQUENCE: 589
cagccccggg agctct                                                     16

<210> SEQ ID NO 590
<211> LENGTH: 21
<212> TYPE: DNA
<213> ORGANISM: Artificial Sequence
<220> FEATURE:
<223> OTHER INFORMATION: synthetic

<400> SEQUENCE: 590
ccatgtctga gggaactgct c                                               21

<210> SEQ ID NO 591
<211> LENGTH: 19
<212> TYPE: DNA
<213> ORGANISM: Artificial Sequence
<220> FEATURE:
<223> OTHER INFORMATION: synthetic

<400> SEQUENCE: 591
agggatcctc caagctccc                                                  19

<210> SEQ ID NO 592
<211> LENGTH: 25
<212> TYPE: DNA
<213> ORGANISM: Artificial Sequence
<220> FEATURE:
<223> OTHER INFORMATION: synthetic

<400> SEQUENCE: 592
gcgttgatct ctcatttcaa accat                                           25

<210> SEQ ID NO 593
<211> LENGTH: 19
<212> TYPE: DNA
<213> ORGANISM: Artificial Sequence
<220> FEATURE:
<223> OTHER INFORMATION: synthetic

<400> SEQUENCE: 593
atggtgaggg gcccataca                                                  19

<210> SEQ ID NO 594
<211> LENGTH: 21
<212> TYPE: DNA
<213> ORGANISM: Artificial Sequence
<220> FEATURE:
<223> OTHER INFORMATION: synthetic

<400> SEQUENCE: 594
```
gactgttttg gtagcaacgg c                                            21

<210> SEQ ID NO 595
<211> LENGTH: 17
<212> TYPE: DNA
<213> ORGANISM: Artificial Sequence
<220> FEATURE:
<223> OTHER INFORMATION: synthetic

<400> SEQUENCE: 595
cgaccccgag cctcaga                                                 17

<210> SEQ ID NO 596
<211> LENGTH: 26
<212> TYPE: DNA
<213> ORGANISM: Artificial Sequence
<220> FEATURE:
<223> OTHER INFORMATION: synthetic

<400> SEQUENCE: 596
caatacttca tgatggtgtg gaaagg                                       26

<210> SEQ ID NO 597
<211> LENGTH: 21
<212> TYPE: DNA
<213> ORGANISM: Artificial Sequence
<220> FEATURE:
<223> OTHER INFORMATION: synthetic

<400> SEQUENCE: 597
gctccatgag ttcctccaca g                                            21

<210> SEQ ID NO 598
<211> LENGTH: 17
<212> TYPE: DNA
<213> ORGANISM: Artificial Sequence
<220> FEATURE:
<223> OTHER INFORMATION: synthetic

<400> SEQUENCE: 598
cagcaccaag agggccg                                                 17

<210> SEQ ID NO 599
<211> LENGTH: 22
<212> TYPE: DNA
<213> ORGANISM: Artificial Sequence
<220> FEATURE:
<223> OTHER INFORMATION: synthetic

<400> SEQUENCE: 599
gatgagcggc acttctgttt tc                                           22

<210> SEQ ID NO 600
<211> LENGTH: 20
<212> TYPE: DNA
<213> ORGANISM: Artificial Sequence
<220> FEATURE:
<223> OTHER INFORMATION: synthetic

<400> SEQUENCE: 600
ttctgccacg taatgagggc                                              20

<210> SEQ ID NO 601
<211> LENGTH: 20
<212> TYPE: DNA

```
<213> ORGANISM: Artificial Sequence
<220> FEATURE:
<223> OTHER INFORMATION: synthetic

<400> SEQUENCE: 601
agactcaatg gccatgcagg                                              20

<210> SEQ ID NO 602
<211> LENGTH: 17
<212> TYPE: DNA
<213> ORGANISM: Artificial Sequence
<220> FEATURE:
<223> OTHER INFORMATION: synthetic

<400> SEQUENCE: 602
atctgcccac gtgcagc                                                 17

<210> SEQ ID NO 603
<211> LENGTH: 21
<212> TYPE: DNA
<213> ORGANISM: Artificial Sequence
<220> FEATURE:
<223> OTHER INFORMATION: synthetic

<400> SEQUENCE: 603
gatgtcgctg ggatagaagc c                                            21

<210> SEQ ID NO 604
<211> LENGTH: 22
<212> TYPE: DNA
<213> ORGANISM: Artificial Sequence
<220> FEATURE:
<223> OTHER INFORMATION: synthetic

<400> SEQUENCE: 604
aaccatctcc aaagccaaag gt                                           22

<210> SEQ ID NO 605
<211> LENGTH: 20
<212> TYPE: DNA
<213> ORGANISM: Artificial Sequence
<220> FEATURE:
<223> OTHER INFORMATION: synthetic

<400> SEQUENCE: 605
gggtcctgca catctccttg                                              20

<210> SEQ ID NO 606
<211> LENGTH: 20
<212> TYPE: DNA
<213> ORGANISM: Artificial Sequence
<220> FEATURE:
<223> OTHER INFORMATION: synthetic

<400> SEQUENCE: 606
ccatcacctc cttcctccct                                              20

<210> SEQ ID NO 607
<211> LENGTH: 23
<212> TYPE: DNA
<213> ORGANISM: Artificial Sequence
<220> FEATURE:
<223> OTHER INFORMATION: synthetic

<400> SEQUENCE: 607
gtgaaagcag gaaatgtatg ccc                                          23
```

<210> SEQ ID NO 608
<211> LENGTH: 26
<212> TYPE: DNA
<213> ORGANISM: Artificial Sequence
<220> FEATURE:
<223> OTHER INFORMATION: synthetic

<400> SEQUENCE: 608
ggcttattca aacctcctta gagcta                                          26

<210> SEQ ID NO 609
<211> LENGTH: 22
<212> TYPE: DNA
<213> ORGANISM: Artificial Sequence
<220> FEATURE:
<223> OTHER INFORMATION: synthetic

<400> SEQUENCE: 609
gacaacttcg agagtcgcat ct                                              22

<210> SEQ ID NO 610
<211> LENGTH: 19
<212> TYPE: DNA
<213> ORGANISM: Artificial Sequence
<220> FEATURE:
<223> OTHER INFORMATION: synthetic

<400> SEQUENCE: 610
cacaggaatg aagggcccc                                                  19

<210> SEQ ID NO 611
<211> LENGTH: 21
<212> TYPE: DNA
<213> ORGANISM: Artificial Sequence
<220> FEATURE:
<223> OTHER INFORMATION: synthetic

<400> SEQUENCE: 611
gtctgagctg cactgcctta t                                               21

<210> SEQ ID NO 612
<211> LENGTH: 21
<212> TYPE: DNA
<213> ORGANISM: Artificial Sequence
<220> FEATURE:
<223> OTHER INFORMATION: synthetic

<400> SEQUENCE: 612
gacagcaggc acggaatatc a                                               21

<210> SEQ ID NO 613
<211> LENGTH: 18
<212> TYPE: DNA
<213> ORGANISM: Artificial Sequence
<220> FEATURE:
<223> OTHER INFORMATION: synthetic

<400> SEQUENCE: 613 gtgccccgc tgtaagac                                                    18

<210> SEQ ID NO 614
<211> LENGTH: 24
<212> TYPE: DNA
<213> ORGANISM: Artificial Sequence
<220> FEATURE:

```
<223> OTHER INFORMATION: synthetic

<400> SEQUENCE: 614
tctctccaga aaggacctaa gtgt                                            24

<210> SEQ ID NO 615
<211> LENGTH: 20
<212> TYPE: DNA
<213> ORGANISM: Artificial Sequence
<220> FEATURE:
<223> OTHER INFORMATION: synthetic

<400> SEQUENCE: 615
cctgcgaggt tcagatgctt                                                 20

<210> SEQ ID NO 616
<211> LENGTH: 20
<212> TYPE: DNA
<213> ORGANISM: Artificial Sequence
<220> FEATURE:
<223> OTHER INFORMATION: synthetic

<400> SEQUENCE: 616
gctctccggt ccttctacct                                                 20

<210> SEQ ID NO 617
<211> LENGTH: 16
<212> TYPE: DNA
<213> ORGANISM: Artificial Sequence
<220> FEATURE:
<223> OTHER INFORMATION: synthetic

<400> SEQUENCE: 617
gccgagcgct gggaag                                                     16

<210> SEQ ID NO 618
<211> LENGTH: 15
<212> TYPE: DNA
<213> ORGANISM: Artificial Sequence
<220> FEATURE:
<223> OTHER INFORMATION: synthetic

<400> SEQUENCE: 618
ccccgcccgc tacct                                                      15

<210> SEQ ID NO 619
<211> LENGTH: 23
<212> TYPE: DNA
<213> ORGANISM: Artificial Sequence
<220> FEATURE:
<223> OTHER INFORMATION: synthetic

<400> SEQUENCE: 619
atttgtgggc tagctcctat gtg                                             23

<210> SEQ ID NO 620
<211> LENGTH: 22
<212> TYPE: DNA
<213> ORGANISM: Artificial Sequence
<220> FEATURE:
<223> OTHER INFORMATION: synthetic

<400> SEQUENCE: 620
acctgtgttc ttctgtgttc cc                                              22
```

```
<210> SEQ ID NO 621
<211> LENGTH: 21
<212> TYPE: DNA
<213> ORGANISM: Artificial Sequence
<220> FEATURE:
<223> OTHER INFORMATION: synthetic

<400> SEQUENCE: 621
tcaaagatgt ggatggagcg g                                              21

<210> SEQ ID NO 622
<211> LENGTH: 18
<212> TYPE: DNA
<213> ORGANISM: Artificial Sequence
<220> FEATURE:
<223> OTHER INFORMATION: synthetic

<400> SEQUENCE: 622
gcagacagcc acgcagat                                                  18

<210> SEQ ID NO 623
<211> LENGTH: 21
<212> TYPE: DNA
<213> ORGANISM: Artificial Sequence
<220> FEATURE:
<223> OTHER INFORMATION: synthetic

<400> SEQUENCE: 623
gccattcctg ggagtacaca g                                              21

<210> SEQ ID NO 624
<211> LENGTH: 18
<212> TYPE: DNA
<213> ORGANISM: Artificial Sequence
<220> FEATURE:
<223> OTHER INFORMATION: synthetic

<400> SEQUENCE: 624
cacgctgaca gctcctgg                                                  18

<210> SEQ ID NO 625
<211> LENGTH: 22
<212> TYPE: DNA
<213> ORGANISM: Artificial Sequence
<220> FEATURE:
<223> OTHER INFORMATION: synthetic

<400> SEQUENCE: 625
ctacactcat gagcactgga cc                                             22

<210> SEQ ID NO 626
<211> LENGTH: 34
<212> TYPE: DNA
<213> ORGANISM: Artificial Sequence
<220> FEATURE:
<223> OTHER INFORMATION: synthetic

<400> SEQUENCE: 626
ttgttatctt tcaggtttta atacaacaac aaat                                34

<210> SEQ ID NO 627
<211> LENGTH: 24
<212> TYPE: DNA
<213> ORGANISM: Artificial Sequence
<220> FEATURE:
<223> OTHER INFORMATION: synthetic
```

```
<400> SEQUENCE: 627
gatgcttgaa atgctctcaa gtcc                                              24

<210> SEQ ID NO 628
<211> LENGTH: 22
<212> TYPE: DNA
<213> ORGANISM: Artificial Sequence
<220> FEATURE:
<223> OTHER INFORMATION: synthetic

<400> SEQUENCE: 628
gggccaatgt tgtgctcaat ac                                                22

<210> SEQ ID NO 629
<211> LENGTH: 18
<212> TYPE: DNA
<213> ORGANISM: Artificial Sequence
<220> FEATURE:
<223> OTHER INFORMATION: synthetic

<400> SEQUENCE: 629
gagccgacca caagctcc                                                     18

<210> SEQ ID NO 630
<211> LENGTH: 22
<212> TYPE: DNA
<213> ORGANISM: Artificial Sequence
<220> FEATURE:
<223> OTHER INFORMATION: synthetic

<400> SEQUENCE: 630
caggtcatct tcaacctcct cg                                                22

<210> SEQ ID NO 631
<211> LENGTH: 17
<212> TYPE: DNA
<213> ORGANISM: Artificial Sequence
<220> FEATURE:
<223> OTHER INFORMATION: synthetic

<400> SEQUENCE: 631
ggacaccccg gcaatgg                                                      17

<210> SEQ ID NO 632
<211> LENGTH: 20
<212> TYPE: DNA
<213> ORGANISM: Artificial Sequence
<220> FEATURE:
<223> OTHER INFORMATION: synthetic

<400> SEQUENCE: 632
tcccgcatct acctggctaa                                                   20

<210> SEQ ID NO 633
<211> LENGTH: 23
<212> TYPE: DNA
<213> ORGANISM: Artificial Sequence
<220> FEATURE:
<223> OTHER INFORMATION: synthetic

<400> SEQUENCE: 633
cgaaggtgtc tgagaagtac tgg                                               23

<210> SEQ ID NO 634
<211> LENGTH: 19
```

```
<212> TYPE: DNA
<213> ORGANISM: Artificial Sequence
<220> FEATURE:
<223> OTHER INFORMATION: synthetic

<400> SEQUENCE: 634
cgtggagaag ggtgagtgc                                                 19

<210> SEQ ID NO 635
<211> LENGTH: 20
<212> TYPE: DNA
<213> ORGANISM: Artificial Sequence
<220> FEATURE:
<223> OTHER INFORMATION: synthetic

<400> SEQUENCE: 635
ctgaaaagaa tcgggcccca                                                20

<210> SEQ ID NO 636
<211> LENGTH: 17
<212> TYPE: DNA
<213> ORGANISM: Artificial Sequence
<220> FEATURE:
<223> OTHER INFORMATION: synthetic

<400> SEQUENCE: 636
ctgatccccg ggctcca                                                   17

<210> SEQ ID NO 637
<211> LENGTH: 21
<212> TYPE: DNA
<213> ORGANISM: Artificial Sequence
<220> FEATURE:
<223> OTHER INFORMATION: synthetic

<400> SEQUENCE: 637
gctttcagag ggctccagat c                                              21

<210> SEQ ID NO 638
<211> LENGTH: 17
<212> TYPE: DNA
<213> ORGANISM: Artificial Sequence
<220> FEATURE:
<223> OTHER INFORMATION: synthetic

<400> SEQUENCE: 638
gcgctccaag gcctcag                                                   17

<210> SEQ ID NO 639
<211> LENGTH: 22
<212> TYPE: DNA
<213> ORGANISM: Artificial Sequence
<220> FEATURE:
<223> OTHER INFORMATION: synthetic

<400> SEQUENCE: 639
tctgtttccc tgataagtgc cg                                             22

<210> SEQ ID NO 640
<211> LENGTH: 20
<212> TYPE: DNA
<213> ORGANISM: Artificial Sequence
<220> FEATURE:
<223> OTHER INFORMATION: synthetic

<400> SEQUENCE: 640
```
tggcaaagga aggcagtgtt                                                    20

<210> SEQ ID NO 641
<211> LENGTH: 22
<212> TYPE: DNA
<213> ORGANISM: Artificial Sequence
<220> FEATURE:
<223> OTHER INFORMATION: synthetic

<400> SEQUENCE: 641
attcccagat tcctcatggt gc                                                 22

<210> SEQ ID NO 642
<211> LENGTH: 25
<212> TYPE: DNA
<213> ORGANISM: Artificial Sequence
<220> FEATURE:
<223> OTHER INFORMATION: synthetic

<400> SEQUENCE: 642
cgaacccctg aattctagct gaata                                              25

<210> SEQ ID NO 643
<211> LENGTH: 20
<212> TYPE: DNA
<213> ORGANISM: Artificial Sequence
<220> FEATURE:
<223> OTHER INFORMATION: synthetic

<400> SEQUENCE: 643
ctgatcggaa gcagcctgtt                                                    20

<210> SEQ ID NO 644
<211> LENGTH: 28
<212> TYPE: DNA
<213> ORGANISM: Artificial Sequence
<220> FEATURE:
<223> OTHER INFORMATION: synthetic

<400> SEQUENCE: 644
atcaggaaac ctcagttcga taaagtat                                           28

<210> SEQ ID NO 645
<211> LENGTH: 21
<212> TYPE: DNA
<213> ORGANISM: Artificial Sequence
<220> FEATURE:
<223> OTHER INFORMATION: synthetic

<400> SEQUENCE: 645
ctgcaagacg agaggactgt c                                                  21

<210> SEQ ID NO 646
<211> LENGTH: 29
<212> TYPE: DNA
<213> ORGANISM: Artificial Sequence
<220> FEATURE:
<223> OTHER INFORMATION: synthetic

<400> SEQUENCE: 646
gtttaaagaa gaaaacccgt atgctagat                                          29

<210> SEQ ID NO 647
<211> LENGTH: 22
<212> TYPE: DNA
<213> ORGANISM: Artificial Sequence

```
<220> FEATURE:
<223> OTHER INFORMATION: synthetic

<400> SEQUENCE: 647
ttgcccctcc aaagtgagtt ac                                              22

<210> SEQ ID NO 648
<211> LENGTH: 29
<212> TYPE: DNA
<213> ORGANISM: Artificial Sequence
<220> FEATURE:
<223> OTHER INFORMATION: synthetic

<400> SEQUENCE: 648
actagcacct tttatactta tccagagac                                       29

<210> SEQ ID NO 649
<211> LENGTH: 19
<212> TYPE: DNA
<213> ORGANISM: Artificial Sequence
<220> FEATURE:
<223> OTHER INFORMATION: synthetic

<400> SEQUENCE: 649
ctccacccca tccccagat                                                  19

<210> SEQ ID NO 650
<211> LENGTH: 26
<212> TYPE: DNA
<213> ORGANISM: Artificial Sequence
<220> FEATURE:
<223> OTHER INFORMATION: synthetic

<400> SEQUENCE: 650
aaagttcttc atagacttgt gggtca                                          26

<210> SEQ ID NO 651
<211> LENGTH: 18
<212> TYPE: DNA
<213> ORGANISM: Artificial Sequence
<220> FEATURE:
<223> OTHER INFORMATION: synthetic

<400> SEQUENCE: 651
cgaagtcctt gggggcac                                                   18

<210> SEQ ID NO 652
<211> LENGTH: 18
<212> TYPE: DNA
<213> ORGANISM: Artificial Sequence
<220> FEATURE:
<223> OTHER INFORMATION: synthetic

<400> SEQUENCE: 652
gcacactgag ggctggtc                                                   18
```

METHODS AND COMPOSITIONS FOR IDENTIFICATION OF TUMOR MODELS

CROSS-REFERENCE TO RELATED APPLICATIONS

This application is a continuation-in-part of PCT/CN2020/079067 filed Mar. 12, 2020, which claims priority to application PCT/CN2019/077750, filed Mar. 12, 2019, the disclosure of which is incorporated herein by reference.

SEQUENCE LISTING

The sequence listing that is contained in the file named "078272-8002US01_SL_ST25", which is 187 KB (as measured in Microsoft Windows) and was created on May 25, 2021, is filed herewith by electronic submission and is incorporated by reference herein.

FIELD OF THE INVENTION

The present invention generally relates to molecular biology, cancer biology and animal models.

BACKGROUND

Cell lines, organoids, xenograft and homograft models are useful model systems in oncology and other biomedical researches. Model authentication and characterization helps their proper utilization and alleviates a series of problems such as misidentification and misuse, cross-contamination, erroneous cancer classification, genomic change due to longtime culture and genetic drift, all were well noted especially in cell lines due to their popular use. For example, various studies reported about 10-40% misidentification/contamination rates for cell line banks.

There are a variety of methods for authenticating cell lines including cell morphology examining, isoenzymology, cytogenetic analysis (karyotyping and FISH), human lymphocyte antigen (HLA) typing, short-tandem repeat (STR) profiling, single-nucleotide polymorphism (SNP) typing, DNA and RNA sequencing (Freedman, L. P. et al. *Biotechniques* 59, 189-90, 192 (2015); Nims, R. W. & Reid, Y. *In Vitro Cell Dev Biol Anim* 53, 880-887 (2017)). Among these technologies, STR profiling has been most widely used and there is a standard (ASN-0002) to guide its application on authenticating human cell lines (Almeida, J. L., Cole, K. D. & Plant, A. L. *PLoS Biol* 14, e1002476 (2016)). A panel of 19 STR markers for mouse cell lines were also developed (Zaaijer, S. et al. *Elife* 6(2017)). The sensitivity of STR assays for detecting contaminant is about 5-10% (Yu, M. et al. *Nature* 520, 307-11 (2015)). In recent years, SNP typing is becoming increasingly used for cell line and biosample authentication owning to its improved accuracy, sensitivity and reduced cost. SNPs can be profiled by PCR and next-generation sequencing (NGS) including transcriptomic sequencing or RNA-seq, whole exome sequencing (WES) and whole genome sequencing (WGS). Current SNP assays have detection sensitivities at about 3-5%. There are also databases with STR, SNP and other information for cell lines to facilitate their authentication and characterization.

Besides cell lines, organoids and mouse tumor models are widely used in oncology research and drug development. Organoids are in vitro three-dimensional culture deriving from stem cells, primary and engineered tumor samples, and xenografted human tumors that maintain many organismal structures and functions. Mouse tumor models are in vivo systems including patient-derived xenograft (PDX), cell line derived xenograft (CDX), syngeneic or mouse cell line-derived models, mouse homograft models, etc. Some of these models, like PDX, can more faithfully capture histopathology and genomics to primary tumors than cell lines. Like cell lines, these tumor models have similar quality control issues, but there are additional problems. In xenograft models, tumors contain human tumor cells and mouse stromal cells, the latter gradually replace human counterparts during the passaging of models, which, when compounded with genomic heterogeneity, implantation site difference (subcutaneous and orthotopic), growth variation and dissection randomness, makes the human-mouse genetic compositions of tumors from even same PDX differ considerably, to the extent that some samples are nearly pure human or mouse content. Such tumor-host mixing and interference occurs to all implanted tumors models, causing fluctuation of allele frequencies for STR markers and SNPs, therefore adversely impacting traditional STR and SNP based authentication methods. Large-scale sample authentication is also a logistic burden and error-prone, especially for biobanks where many kinds of in vitro and in vivo models are simultaneously maintained and used. Therefore, there is a need to develop new SNP based assay to identify and authenticate tumor models.

SUMMARY OF INVENTION

In one aspect, the present disclosure provides a method for identifying or authenticating a sample. In one embodiment, the method comprises: obtaining a nucleic acid from a sample; detecting a genotype for the sample at a plurality of human single nucleotide polymorphism (SNP) loci or at a plurality of mouse SNP loci; comparing the genotype for the sample to a reference genotype; and determining the identification of the sample. In certain embodiments, the human SNP is selected from the group as shown in Table 1. In certain embodiments, the mouse SNP is selected from the group as shown in Table 2

In certain embodiments, the sample is a cell, a tissue, an organoid, or a combination thereof. In certain embodiments, the sample is a cell line or a tumor tissue. In certain embodiments, the sample is derived from a xenograft or homograft tumor model. In certain embodiments, the sample is derived from patient-derived xenograft (PDX), cell line derived xenograft (CDX), syngeneic or mouse cell line-derived models, mouse homograft models.

In certain embodiments, the sample comprises a contaminant, the method further comprises determining the percentage of the contaminant in the sample. In certain embodiments, the method further comprises determining the identity of the contaminant.

In certain embodiments, the detecting step uses next-generation sequencing (NGS) or a sequencing-based SNP array. In certain embodiments, the nucleic acid is barcoded.

In certain embodiments, the method further comprises identifying the gender of a subject from which the sample is obtained. In certain embodiments, the method further comprises identifying the ethnicity of a subject from which the sample is obtained. In certain embodiments, the method further comprises detecting the presence of virus or mycoplasma in the sample. In certain embodiments, the method further comprises determining strain of an immunodeficient mouse from which the sample is obtained.

In another aspect, the present disclosure provides a method for determining the alleles in a sample. In some embodiments, the method comprises: obtaining a nucleic acid from the sample; selecting a set of single nucleotide polymorphism (SNP) of the sample that can be amplified together in a multiplex amplification reaction, wherein the set of SNP loci are selected from the group as shown in Table 1 or Table 2; providing a set of oligonucleotide primer pairs, wherein each oligonucleotide primer pair in the set flanks a single locus in the set of SNP loci, and wherein each oligonucleotide primer pair is capable of amplifying a single locus from the set of SNP loci in a multiplex amplification reaction; co-amplifying the set of SNP loci in a multiplex amplification reaction, wherein the product of the multiplex amplification reaction comprises a mixture of amplified alleles from each of the co-amplified loci in the set of SNP loci; and evaluating the products of the co-amplification reaction to determine the alleles present at each of the loci analyzed in the set of SNP loci within the sample.

In another aspect, the present disclosure provides a method of authenticating a sample comprising a human component and a mouse component. In certain embodiments, the method comprises obtaining a nucleic acid from the sample; detecting a genotype of the sample at 100 or more mouse genomic loci, each of the mouse genomic loci having a corresponding homologous human genomic locus, wherein each of mouse genomic loci and the corresponding homologous human genomic locus have identical flanking nucleotide sequences; and determining the ratio of the mouse component in the sample based on the genotype. In certain embodiments, the mouse genomic loci are selected from Table 6.

In another aspect, the present disclosure provides a kit for identifying a sample. In certain embodiments, the kit comprises primers for detecting in a sample at a group of human SNP loci or at a group of mouse SNP loci. In certain embodiments, the kit further comprises an agent for amplifying DNA fragments containing the human or mouse SNPs using the primers.

In another aspect, the present disclosure provides a microarray for identifying a human or mouse sample. In certain embodiments, the microarray comprises probes for detecting a genotype of a sample at a group of human or mouse SNP loci.

In yet another aspect, the present disclosure provides a non-transitory computer readable medium having instructions stored thereon, wherein the instructions, when executed by a processor, cause the processor to: retrieve a genotype of a sample at a group of human or mouse SNP loci; compare the genotype of the sample to a reference genotype; and determine the identification of the sample.

In yet another aspect, the present disclosure provides a method for authenticating a sample comprising a major component and a minor component. In certain embodiments, the method comprises detecting a genotype of the sample at 100 or more SNP loci; determining an SNP heterogeneity ratio for each of the SNP loci according to the formula shown in Table 11; determining a sample heterogeneity ratio based on the SNP heterogeneity ratios for the SNP loci using a Gaussian mixture distribution that models the genotype; and determining the major component of the sample by: comparing the genotype of the sample to a group of reference genotypes, each detected in a reference sample, identifying a reference sample that has a reference genotype with the highest identity to the genotype of the sample, determining that the major component is the reference sample if: (i) the reference genotype is more than 90% identical to the genotype of the sample and the sample heterogeneity ratio is less than 10%, or (ii) the reference genotype is more than 80% identical to the genotype of the sample and the sample heterogeneity ratio is more than 10%.

In certain embodiments, the method further comprises determining the minor component of the sample. In certain embodiments, the method further comprises determining the percentage of the major component and minor component in the sample.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1A: Genotype similarities for unrelated/mismatch, identical and closely related cell line pairs. FIG. 1B: Heterogeneity ratios in 118 uncontaminated cell lines, 220 PDX and 31 PDXO models. FIG. 1C: Heterogeneity ratio is positively correlated with mouse ratio in PDX models.

FIG. 2A-2D: A serial mixes of cell lines MV-4-11(MV411) and LNCaP clone FGC (LNCAPCLONEFGC) with cell ratios 5%, 2.5%, 1.25% and 0.625% for the latter.

FIG. 3A: Sample 19R58129 is MV411 mixed with minor contaminating cell line LNCaP clone FGC (LNCAPCLONEFGC). LNCAPCLONEFGC was correctly identified as the contaminant (p-value=5.01E-17) with a contamination ratio of 1.41%. LNCaP-C4-2 (C42) and LNCAPCLONEFGC were both derived from LNCaP and share high genetic identity. In the quantile-quantile plot, each dot is a reference cell line, theoretical and sample quantiles were calculated from a beta distribution fitted to genotype similarities between MV411 and 1055 reference cell lines. The 99% confidence band is shaded. FIG. 3B: Accuracy of inferring the contaminating second cell line in a cell line under different heterogeneity ratios. A total of 94 cell line samples with known contaminating second cell line were tested, samples were binned by heterogeneity ratio. FIG. 3C: Cell line "G-292 clone A141B1" had a sample heterogeneity ratio of 7.62% with a distinct right peak in the probability density of SNP heterogeneity ratios, indicating it was contaminated. FIG. 3D: OCI-AML-2 was inferred as the contaminant (p-value=1.58E-07) in cell line "G-292 clone A141B1" with a contamination ratio of 6.21%. FIG. 3E: Near perfect correlation between estimated and known contamination ratios in simulated cell line mixtures. FIG. 3F: High correlation between heterogeneity ratios and contamination ratios for cell line samples with known contamination.

FIG. 4A: Accurate estimation of mouse ratio by the deep NGS sequencing in a serial of human-mouse DNA mixtures with mouse ratios 90%, 80%, 70%, 50%, 30%, 20%, 10%, 7%, 5% and 0%. FIG. 4B-4C:

Mouse ratios estimated in 220 PDX and 31 PDX-derived organoid models by three approaches, assayed on the same sample for each model. FIG. 4D: A quadratic relationship between mouse ratios estimated by the deep NGS sequencing and WES in 220 PDX models.

DETAILED DESCRIPTION OF THE INVENTION

Figure 1A:
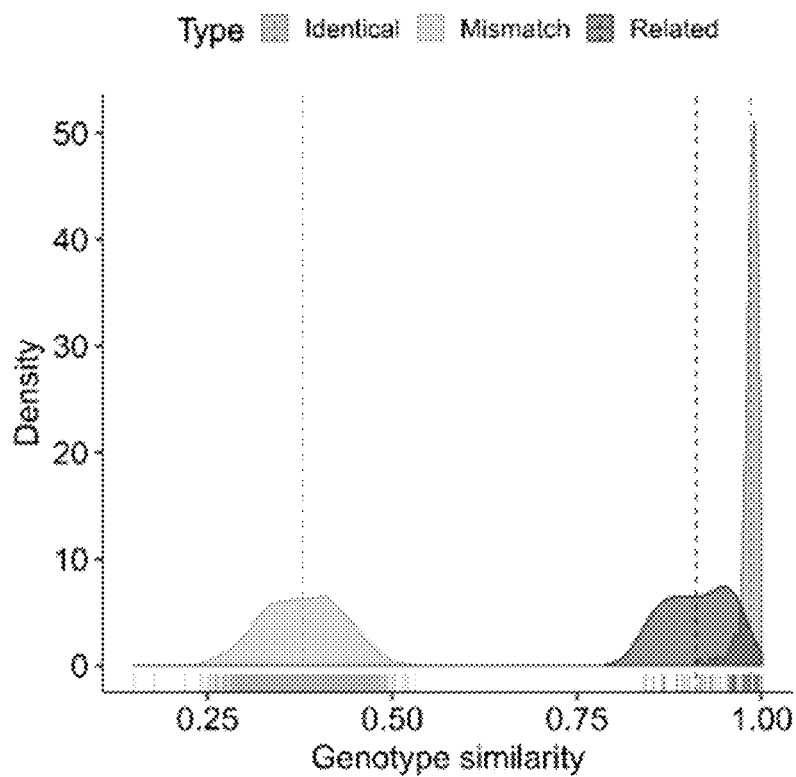
FIG. 1A-1C shows the cell line authentication and sample genetic heterogeneity.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definitions

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

The term "allele" refers to one of two or more existing genetic variants of a specific polymorphic locus.

The term "amount" or "level" refers to the quantity of a polynucleotide of interest or a polypeptide of interest present in a sample. Such quantity may be expressed in the absolute terms, i.e., the total quantity of the polynucleotide or polypeptide in the sample, or in the relative terms, i.e., the concentration of the polynucleotide or polypeptide in the sample.

The terms "amplicon," "amplification product" and "amplified sequence" are used interchangeably herein and refer to the product of a amplification technique for increasing polynucleotide sequences, either linearly or exponentially. An amplicon can be double-stranded or single-stranded and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" and "amplified sequence" includes products from any number of cycles of amplification reactions.

As used herein, "amplify" refers to the process of enzymatically increasing the amount of a specific nucleotide sequence. This amplification is not limited to but is generally accomplished by PCR, which involves multiple cycles of a process comprising the steps of denaturation, annealing and extension. As used herein, "denaturation" refers to the separation of two complementary nucleotide strands from an annealed state. Denaturation can be induced by a number of factors, such as, for example, ionic strength of the buffer, temperature, or chemicals that disrupt base pairing interactions. As used herein, "annealing" refers to the specific interaction between strands of nucleotides wherein the strands bind to one another substantially based on complementarity between the strands as determined by Watson-Crick base pairing. It is not necessary that complementarity be 100% for annealing to occur. As used herein, "extension" refers to the amplification cycle after the primer oligonucleotide and target nucleic acid have annealed to one another, wherein the polymerase enzyme catalyzes primer extension, thereby enabling amplification, using the target nucleic acid as a replication template.

As used herein, the term "cancer" or "tumor" refers to any diseases involving an abnormal cell growth and include all stages and all forms of the disease that affects any tissue, organ or cell in the body. The term includes all known cancers and neoplastic conditions, whether characterized as malignant, benign, soft tissue, or solid, and cancers of all stages and grades including pre- and post-metastatic cancers. In general, cancers can be categorized according to the tissue or organ from which the cancer is located or originated and morphology of cancerous tissues and cells. As used herein, cancer types include, without limitation, acute lymphoblastic leukemia (ALL), acute myeloid leukemia, adrenocortical carcinoma, anal cancer, astrocytoma, childhood cerebellar or cerebral, basal-cell carcinoma, bile duct cancer, bladder cancer, bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, chronic lymphocytic leukemia, chronic myelogenous leukemia, colon cancer, emphysema, endometrial cancer, ependymoma, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer (renal cell cancer), laryngeal cancer, leukaemia, liver cancer, lung cancer, neuroblastoma, non-Hodgkin lymphoma, ovarian cancer, pancreatic cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, vaginal cancer.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ (e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell); a cell from an endocrine system or organ (e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte)); a cell from a nervous system or organ (e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph)); a cell from a respiratory system or organ (e.g., a pneumocyte (a type I pneumocyte and a type II pneumocyte), a clara cell, a goblet cell, an alveolar macrophage); a cell from circular system or organ (e.g., myocardiocyte and pericyte); a cell from digestive system or organ (e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell)); a cell from integumentary system or organ (e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell)), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell. In certain examples, the cells are those used for mass bioproduction, e.g., CHO cells.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%>, 70%>, 80%>, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

As used herein, the term "contaminant" means a component present in a sample that is different from the major component in the sample or cause impurity or other undesirable effect of the sample, such as spoiling, corruption, infection.

The terms "determining," "assessing," "assaying," "measuring" and "detecting" can be used interchangeably and refer to both quantitative and semi-quantitative determinations. Where either a quantitative and semi-quantitative determination is intended, the phrase "determining a level" of a polynucleotide or polypeptide of interest or "detecting" a polynucleotide or polypeptide of interest can be used.

The term "genome" refers to the total genetic information carried by an individual organism or cell, represented by the complete DNA sequences of its chromosomes.

The term "hybridizing" refers to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopsy). A "stringent hybridization" and "stringent hybridization wash conditions" in the context of nucleic acid hybridization (e.g., as in array, microarray, Southern or northern hybridizations) are sequence dependent, and are different under different environmental parameters. An extensive guide to the hybridization of nucleic acids is found in, e.g., Tijssen *Laboratory Techniques in Biochemistry and Molecular Biology—Hybridization with Nucleic Acid Probes part* 1*, Ch.* 2*, "Overview of principles of hybridization and the strategy of nucleic acid probe assays*," (1993) Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell *Molecular Cloning: A Laboratory Manual* (3rd ed.) Vol. 1-3 (2001) Cold Spring Harbor Laboratory, Cold Spring Harbor Press, NY). An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×SSC to 6×SSC at 40° C. for 15 minutes.

The term "locus" refers to any segment of DNA sequence in a genome defined by chromosomal coordinates in a reference genome known to the art, irrespective of biological function. A DNA locus can contain multiple genes or no genes; it can be a single base pair or millions of base pairs.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "oligonucleotide" refers to a nucleic acid sequence of at least about five nucleotides to about 500 nucleotides (e.g. 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 30 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., as are well known in the art.

The term "polymorphic locus" refers to a genomic locus at which two or more alleles have been identified.

The term "primer" refers to an oligonucleotide and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically, a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides (dNTPs) and the like. As used herein, the terms "amplification primer" and "oligonucleotide primer" are used interchangeably and refer to an oligonucleotide, capable of annealing to an RNA or DNA region adjacent a target sequence, and serving as an initiation primer for DNA synthesis under suitable conditions well known in the art. Typically, a PCR reaction employs an "amplification primer pair" also referred to as an "oligonucleotide primer pair" including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

The term "reference genotype" as used herein refers to a predetermined genotype of one or more genomic loci that is present in a reference sample, e.g., a sample with known identity. The reference genotype is suitable for the use of a method of the present invention, to serve as a basis for comparing the genotype of specific genomic loci that is present in a test sample. A reference genotype may vary depending on the nature of the sample as well as other factors such as the gender, age, ethnicity of the subjects based on whom such a reference sample is established.

The term "sample" or "biological sample" used herein refers to any cell, tissue, organoid or any other sample that contains one or more nucleic acid molecule(s) of interest. In certain embodiments, the sample is a cell (e.g., normal cell, cancer cell, cell line), a tissue (e.g., a normal tissue, a cancer tissue, a xenograft or allograft tissue), an organoid, etc.

The term "single nucleotide polymorphism" or "SNP" refers to a single nucleotide position in a genomic sequence where two or more alternative alleles are present at appreciable frequency within a population, e.g., >1%. SNPs can occur within a coding sequence of a gene, within noncoding regions of a gene and/or in an intergenic (e.g., intron) region of a gene. SNPs that are not in protein coding regions can still have effects on gene splicing, transcription factor binding and/or the sequence of non-coding RNA. The SNP nomenclature provided herein refers to the official Reference SNP (rs) identification number as assigned to each unique SNP by the National Center for Biotechnological Information (NCBI), which is available in the GenBank® database.

As used herein, the term "subject" refers to a human or any non-human animal (e.g., mouse, rat, rabbit, dog, cat, cattle, swine, sheep, horse or primate). A human includes pre and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "substrate" when used in the context of an array refers to material capable of supporting associated assay components (e.g., assay regions, cells, test compounds, etc.). Examples of substrates include, but are not limited to glass, Si-based materials, functionalized polystyrene, functionalized polyethylene-glycol, functionalized organic polymers, nitrocellulose or nylon membranes, paper, cotton, and materials suitable for synthesis. Substrates need not be flat and include any type of shape including spherical shapes (e.g., beads). Materials attached to a substrate may be attached to any portion of the substrate (e.g., may be attached to an interior portion of a porous substrate material). Preferred embodiments of the present technology have nucleic acid probes attached to a substrate. A nucleic acid probe is "attached" to a substrate when it is associated with the substrate through a non-random chemical or physical interaction. In some preferred embodiments, the attachment is through a covalent bond, e.g., as provided by a linker.

The term "tumor models", as used herein, refer to cells, tissues or animals used to study the development and progression of cancer, and to test treatments before they are given to human.

The term "tumor sample" includes a biological sample or a sample from a biological source that contains one or more tumor cells. Biological samples include samples from body fluids, e.g., blood, plasma, serum, or urine, or samples derived, e.g., by biopsy, from cells, tissues or organs, preferably tumor tissue suspected to include or essentially consist of cancer cells.

SNPs for Identification of Tumor Samples

Misidentification and contamination of biobank samples (e.g., cell lines) have plagued biomedical research. Short-tandem repeat (STR) and single-nucleotide polymorphism (SNP) assays are widely used to authenticate biosamples and can detect contamination at a sensitivity of 5-10% and 3-5%, respectively. The present disclosure in one aspect provides a method with ≤1% sensitivity for detecting contamination. It can further identify the contaminant and estimate the contamination ratio for mixed cell line samples. It is by far the most sensitive and accurate method reported for cell line authentication. In certain embodiments, the method can also detect interspecies contamination in human-mouse mixed samples such as xenograft tumors, and accurately estimate the mouse ratio. In certain embodiments, *mycoplasma* and mollicutes are among the searching targets as well. In certain embodiments, this multi-functional method simultaneously infers population structure and gender of human samples. In certain embodiments, owning to DNA barcoding technology, the method disclosed herein can profile 100-200 samples in a single run at per-sample cost comparable to conventional STR assays, making it truly high-throughput and low-cost tool for maintaining high-quality biobanks.

The methods and compositions described herein are based, in part, on the discovery of a group of SNP loci that can be used to identify and authenticate a sample obtained from a tumor model. In certain embodiment, the tumor model is a human tumor model, including primary human tumor, patient-derived xenografts (PDX), human tumor cell line, human cell-line derived xenograft and human organoids. In certain embodiments, SNPs are selected from human SNPs based on the RNAseq or Whole-Exome Sequencing (WES) data of a number of human tumor models. The selected human SNPs are located in exonic regions of highly expressed genes that are located in mostly non-linkage-disequilibrium (non-LD) blocks across 22 autosomes. Each human tumor model therefore has a unique genotype (i.e., SNP fingerprint) at the selected human SNP loci.

In certain embodiments, the human SNP loci selected have homology in mouse genome. When a sample is amplified using primers targeting such human SNP loci, nucleotide sequences of corresponding mouse loci may be generated if the sample is mixed with mouse cell or tissue. Such human SNPs may be used to estimate the percentage of mouse content in the mixture of human and mouse cells/tissues, e.g., based on the number of mouse and human reads of these SNPs.

In certain embodiments, the human SNPs used herein are selected from the group as shown in Table 1.

In certain embodiments, the SNPs include a group of mouse SNPs to identify and authenticate mouse tumor models such as mouse tumor cell line. In some embodiments, the mouse SNPs used herein are selected from the group as shown in Table 2.

In certain embodiments, the SNPs further include human SNPs in sex chromosomes (chromosome X and chromosome Y) to determine the gender of a subject from which the sample is obtained. In certain embodiments, the sex chromosome SNPs are selected from the group as shown in Table 3.

In certain embodiments, the SNPs further include mouse SNPs that can be used to determine the strain of an immunodeficient mouse from which the sample is obtained. In some embodiments, the SNPs are shown in Table 4.

Methods

In one aspect, the present disclosure provides a method for identifying and authenticating a sample.

In certain embodiments, the method disclosed herein is to match a sample to a reference (e.g. standard cancer cell lines). Conventional STR and SNP assays largely used genotype-based Tanabe-Masters algorithm and its variations. STR assays generate analog signals for a dozen of markers. SNP assays genotype often many more SNPs. Therefore, higher similarity thresholds are often used by SNP assay to call two samples match. However, the matching power of conventional assays can be severely compromised for contaminated samples even with ~100 SNPs. In certain embodiments, the method disclosed herein performed high-depth (3000λ) sequencing of 237 SNP sites for human samples, and showed 100% accuracy in identifying a sample or the major component of contaminated samples.

In certain embodiments, the method disclosed herein is to detect contamination in biological samples. The sensitivity for detecting contamination in cell lines is about 5-10% for STR assays and 3-5% for SNP assays. However, performance can be rather unstable, to the extent that even a >20% contamination was not detected in a mixture of two unrelated cell lines by a 96-SNP assay (Liang-Chu, M. M. et al. *PLoS One* 10, e0116218 (2015)). In certain embodiments, the method disclosed herein consistently reaches 2% sensitivity when only using the heterogeneity ratio, by both its value and distinct bi/tri-modal distribution. The sensitivity reaches 1% if the contaminant is in a library of reference samples with SNP fingerprint. Such sensitivity is virtually the theoretic detection limit, because uncontaminated cell lines, due to multiclonality and sequencing errors, exhibit a comparable level of genetic heterogeneity to cell line samples with ~1% contamination.

In certain embodiments, the method disclosed herein is to identify contaminants. Cross-contamination of cell lines is common in biobanks. The composition of a contaminated culture changes over time due to different growth rates of cell lines. Cell lines differ in genomics such as gene mutations and may respond differently to drug treatment, causing erroneous results in drug screening. The inventors of the present disclosure constructed a SNP fingerprint library for over 1000 cancer cell lines, with that a contaminating cell line can be unambiguously identified. Further the contamination ratio can be accurately estimated. Besides checking cell line quality, this capacity can have other utilizations such as monitoring the dynamic composition of two cell lines under biological or chemical interference.

Besides intraspecies contamination, in certain embodiments, the method disclosed herein is able to accurately detect and quantify interspecies contamination between human and mouse. In certain embodiments, the method disclosed herein uses not SNPs but 108 homologous DNA segments that are diverged between the two species but have identical flanking nucleotide sequences, so common primers can be designed for unbiased amplification of human and mouse DNA segments. This approach showed perfect performance in a serial of mouse-human DNA mixture benchmark samples. The homology-based principle can be used for detecting other interspecies contaminations.

In certain embodiments, the power of the method disclosed herein comes from several novel features. The first is deep NGS sequencing, which obtains both the genotype and nucleotide frequency of SNPs, while conventional STR and SNP assays only profile SNP genotypes. Secondly, beside SNP profiling, the method disclosed herein performs targeted sequencing for detecting mycoplasma contamination and estimating mouse-human mix ratios. Thirdly, a suit of statistical models and algorithms have been developed to exploit the deep NGS sequencing data, making the authentication process automatic, robust and objective. Finally, DNA barcode technology is used to enable parallel sequencing of 100-200 samples simultaneously that drastically reduces cost.

The high-throughput low-cost methods disclosed herein that can be routinely used by biobanks to maintain authentic and high-quality samples. The method can be broadly adapted for samples from other species and even microbiome, and can be implemented on any NGS sequencing platforms.

In one embodiment, the method comprises: obtaining a nucleic acid from a sample; detecting a genotype for the sample at a plurality of human or mouse single SNP loci disclosed herein; comparing the genotype for the sample to a reference genotype detected in a reference sample; and determining the identification of the sample. In certain embodiments, the genotype at 50, 60, 70, 80, 90, 100, 110, 120, 130, 140, 150, 160, 170, 180, 190, 200 or more SNP loci is detected.

The nucleic acid obtained from a sample can be RNA or DNA. In certain embodiments, the nucleic acid obtained from a sample is genomic DNA isolated from the sample. In certain embodiments, the nucleic acid obtained from a sample is genomic DNA is total RNA or mRNA isolated from the sample. In certain embodiments, the nucleic acid obtained from a sample is amplified, e.g. by PCR reaction or PCR following reverse transcription.

The genotype for the sample at SNP loci can be detected based on any suitable methods known in the art, for example, but not limited to, sequencing based methods and hybridization-based methods.

In certain embodiments, the detecting step involves an amplification step. In such case, the detecting agent comprises at least a pair of primers which can hybridize to the genomic region containing the SNP locus and amplify a polynucleotide sequence encompassing the SNP locus in the presence of a polymerase. The pair of primers used to amplify the genomic region containing the SNP has sufficient identity with or complementarity to at least a portion of the genomic region such that the primer or the probe can specifically hybridize to the genomic region or to its complementary strand. "Specifically hybridize" as used herein means the primer or probe can hybridize to the intended sequence under stringent conditions. "Stringent condition" as used herein refers to hybridizing at 42° C. in a solution consisting of 5×SSPE, 5×Denhardt's solution, 0.5% SDS, and 100 ug/mL denatured salmon sperm DNA, and then washing at 42° C. with a solution comprising 0.5×SSC and 0.1% SDS.

The method of designing the pair of primers for a specific SNP locus is generally known in the art. For example, Primer3 software, available online from the Massachusetts Institute of Technology, may be used to design PCR primers to flank the STR regions by inputting the sequences for the SNP locus.

In certain embodiments, the amplification step involves amplifying alleles at multiple loci in one reaction. In certain embodiments, the amplification step comprises selecting a set of single nucleotide polymorphism (SNP) of the sample that can be amplified together in a multiplex amplification reaction, wherein the set of SNP loci are selected from the group as shown in Table 1 or Table 2; providing a set of oligonucleotide primer pairs, wherein each oligonucleotide primer pair in the set flanks a single locus in the set of SNP loci, and wherein each oligonucleotide primer pair is capable of amplifying a single locus from the set of SNP loci in a multiplex amplification reaction; co-amplifying the set of SNP loci in a multiplex amplification reaction, wherein the product of the multiplex amplification reaction comprises a mixture of amplified alleles from each of the co-amplified loci in the set of SNP loci; and evaluating the products of the co-amplification reaction to determine the alleles present at each of the loci analyzed in the set of SNP loci within the sample. An example of a set of SNP loci with the oligonucleotide primer pairs that can be amplified together in a multiplex amplification reaction is shown in Table 12.

After amplification by a suitable nucleic acid amplification method such as PCR, the sequence or the SNP in the amplification product is detected. In certain embodiments, the amplification product has a length of 50 bp-500 bp. In certain embodiments, the sequence of the SNP in the amplification product is detected using sequencing-based methods, e.g., next-generation sequencing (NGS) methods. In certain embodiments, NGS methods are used to determine the sequences in a large number of SNP loci. In certain embodiments, NGS methods can be used to simultaneously determine the sequences of SNP loci from a number of samples by barcoding the nucleic acid obtained from each sample.

When the nucleic acid obtained from a sample is RNA, the amplification step may optionally comprise a reverse transcription step to produce cDNA of the RNA in the sample. The cDNA is then amplified using the primers to allow detection of presence of the SNP.

In some embodiments, microarrays, e.g., are employed to detect the SNPs in the nucleic acid. Microarray consists of a reproducible pattern of capture probes attached to a solid support. Labeled RNA or DNA is hybridized to complementary probes on the array and then detected by laser scanning. The presence of a SNP can be detected by measuring the intensity of the labeled RNA or DNA that bind to specific probes on the array.

Techniques for the synthesis of these arrays using mechanical synthesis methods are described in, e.g., U.S. Pat. No. 5,384,261. Although a planar array surface is often employed the array may be fabricated on a surface of virtually any shape or even a multiplicity of surfaces. Arrays may also be nucleic acids on beads, gels, polymeric surfaces, fibers such as fiber optics, glass or any other appropriate substrate, see U.S. Pat. Nos. 5,770,358, 5,789,162, 5,708, 153, 6,040,193 and 5,800,992. Arrays may be packaged in such a manner as to allow for diagnostics or other manipulation of an all-inclusive device.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.* (1981) 22: 1859-1862, using an automated synthesizer, as described in Needham-Van Devanter et al, *Nucleic Acids Res.* (1984) 12:6159-6168.

In certain embodiments, the method further comprises identifying the gender of a subject from which the sample is obtained, e.g., by detecting sex chromosome SNPs selected from the group as shown in Table 3. In certain embodiments, the method further comprises identifying the ethnicity of a subject from which the sample is obtained. In certain embodiments, the method further comprises determining strain of an immunodeficient mouse from which the sample is obtained, e.g., by detecting vendor SNPs as shown in Table 4.

In certain embodiments, the method disclosed herein further includes detecting common viral infection and mycoplasma contamination in tumor models, including hepatisis A/B/C virus (HAV/HBV/HCV), human immunodeficiency virus (HIV), Epstein-Barr virus (EBV), and human papillomavirus (HPV). In certain embodiments, the markers used to detect viral infection and mycoplasma contamination are shown in Table 5.

In certain embodiments, the method disclosed herein can be used to authenticating a sample comprising a major component and a minor component. In certain embodiments, the method comprises estimating heterogeneity ratios; determining major component of the sample; determining minor component of the sample; and estimating mixture ratio of the major and minor components.

In certain embodiments, the heterogeneity ratios can be estimated as follows. There are six informative genotype combinations that can be used to estimate heterogeneity ratios from the deep NGS sequencing data (Table 11). They exhibit four distinct nucleotide frequency patterns. Combinations 1 and 2 generate the same pattern, and we use an average formula to calculate the percentage of the minor component S2, or the heterogeneity ratio. The formula produces an exact estimate of the ratio when the two combinations occur with equal frequency, a scenario that should be closely approximated when the number of SNPs is large. Similar averaging approach is used for Combinations 4 and 5. When the heterogeneity ratio is low, sequencing error may interfere the inference of heterogeneity ratio. To alleviate this, a 2-step statistical procedure can be used. Assuming sequencing error is e=0.001 and the sequencing depth is n (n≥500, any SNP with n<500 is discarded) at a given SNP site, the probability of observing k erroneous nucleotides follows a binomial distribution with parameters n and e.

$$f(k, n, e) = \binom{n}{k} e^k (1-e)^{n-k}$$

For each n, the cumulative density function can be calculated to obtain a threshold h so that the probability of observing more than h erroneous nucleotides out of the n nucleotides is smaller than 0.01. In the sequencing data, any low-frequency nucleotide with number of reads smaller than a corresponding threshold h is discarded. An Expectation-Maximization algorithm (package mclust in R, version 3.5.3) is then used to estimate parameters of a Gaussian mixture (with 1 to 3 components) that models the distribution of nucleotide frequencies smaller than a maximal heterogeneity (0.2 used for all samples in this study). If there is only a single Gaussian component or the Gaussian component with smallest mean accounts for more than 60% of all data points, median of all data points is taken as the sample heterogeneity ratio, otherwise, median of data points in the other Gaussian component(s) is taken as the sample heterogeneity ratio.

To determine the major component in the sample, the genotype at a SNP site is determined using only nucleotides with allele frequencies larger than a threshold, 10% for reference samples and 25% for test samples which may be contaminated. The genotype similarity between a reference sample and a test sample is the percentage of SNPs with identical genotypes, excluding SNPs with sequencing depth less than 500 in the test sample. The major component of the test sample is the reference sample with the highest genotype similarity, which must be greater than 90% (or 80%) if the heterogeneity ratio of the test sample is <10% (or >10%). Otherwise, no major component is called.

After the estimation of heterogeneity ratio and determination of major component, the minor component of a test sample can be determined. For a mixture of the major component and one of the other reference samples (e.g., all cell lines with genomic data), a chimeric genotype can be obtained, with possibly 1 to 4 nucleotides, at every SNP site. Frequencies of nucleotides are calculated using the heterogeneity ratio. Similarly, the chimeric genotype of the test sample is obtained. The two chimeric genotypes are considered identical if they harbor same nucleotides and frequencies of each nucleotide are within three folds. The genotype similarity between the test sample and each reference sample combined with the major component is then calculated. The set of all pairwise genotype similarities are then fitted by a beta distribution with parameters $(\alpha, \beta)$ $$f(x, \alpha, \beta) = \frac{\Gamma(\alpha+\beta)}{\Gamma(\alpha)\Gamma(\beta)} x^{\alpha-1}(1-x)^{\beta-1}$$

In the equation, $\Gamma(\alpha)$ is the gamma function, x is genotype similarity. Its parameters are estimated by package fitdistrplus in R (version 3.5.3). From the fitted beta distribution the probability of observing any genotype similarity larger than a specific value is calculated. A quantile-quantile graph with 99% confidence band is plotted for all observed genotype similarities for visualization. A reference sample is considered the minor component if (1) it has the highest genotype similarities, (2) its genotype similarity is above the 99% confidence upper bound in the quantile-quantile graph, and (3) its p-value<1.0E-6 in the fitted beta distribution.

The mix ratio for two reference samples can be estimated as follows. Assume that two component S1 and S2 are mixed with ratio $\theta$ for S1 and $(1-\theta)$ for S2 where $0 \leq \theta \leq 1$. From deep NGS sequencing data, nucleotide frequencies of all n SNPs in both component can be accurately estimated. For a SNP, its four nucleotide frequencies are denoted, which sum to 1, as $\{A_1, T_1, G_1, C_1\}$ for component 51 and $\{A_2, T_2, G_2, C_2\}$ for component S2. In principle, one of the frequencies is close to 1 if the SNP is homozygous, and two frequencies are both close to 0.5 if the SNP is heterozygous. Actual data may have some deviations due to sequencing errors and randomness, as well as multiclonality of cell lines.

From sequencing data of the mix sample, the actual occurrences of the four nucleotides are denoted as $x=\{n_A, n_T, n_G, n_C\}$. The likelihood of such observation is $$\mathcal{L}(\theta \mid x) = P_\theta(x) = const \times \prod_{M \in \{A,T,G,C\}} (\theta M_1 + (1-\theta) M_2)^{n_M}$$

The likelihood $P_\theta(x_i)$ can be calculated for any SNP i∈(1, 2, ..., n) with observed data $x_i$, the likelihood of observing data X={$x_1, x_2, ..., x_n$} for all SNPs is $$\mathcal{L}(\theta|X) = const \times \prod_{i=1}^{n} P_\theta(x_i)$$

The log-likelihood is therefore $$\log\mathcal{L}(\theta|X) = \sum_{i=1}^{n} \log P_\theta(x_i)$$

θ that maximizes the likelihood can be solved by stepwise increment of θ.

Kits and Microarrays

In another aspect, the present disclosure provides kits for use in the methods described above. The kits may comprise any or all of the reagents to perform the methods described herein. In certain embodiments, the kit comprises primers for detecting in a sample at a group of human SNP loci or at a group of mouse SNP loci. In certain embodiments, the kit further comprises primers for detecting sex chromosome SNPs to identify the gender of a subject from which the sample is obtained. In certain embodiments, the kit further comprises primers for detecting ethnicity SNPs to identify the ethnicity of a subject from which the sample is obtained. In certain embodiments, the kit further comprises primers for detecting vendor SNPs to determine the strain of an immunodeficient mouse from which the sample is obtained. In certain embodiments, the kit further comprises primers for detecting virus infection or mycoplasma contamination in the sample.

In certain embodiments, the kit further comprises an agent for amplifying DNA fragments containing the human or mouse SNPs using the primers. In addition, the kits may include instructional materials containing directions (i.e., protocols) for the practice of the methods provided herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In another aspect, the present disclosure provides oligonucleotide probes attached to a solid support, such as an array slide or chip, e.g., as described in Eds., Bowtell and Sambrook *DNA Microarrays: A Molecular Cloning Manual* (2003) Cold Spring Harbor Laboratory Press. Construction of such devices are well known in the art, for example as described in US patents and patent Publications U.S. Pat. No. 5,837,832; PCT application WO95/11995; U.S. Pat. Nos. 5,807,522; 7,157,229, 7,083,975, 6,444,175, 6,375,903, 6,315,958, 6,295,153, and 5,143,854, 2007/0037274, 2007/0140906, 2004/0126757, 2004/0110212, 2004/0110211, 2003/0143550, 2003/0003032, and 2002/0041420. Nucleic acid arrays are also reviewed in the following references: *Biotechnol Annu Rev* (2002) 8:85-101; Sosnowski et al. *Psychiatr Genet* (2002)12(4): 181-92; Heller, *Annu Rev Biomed Eng* (2002) 4: 129-53; Kolchinsky et al., *Hum. Mutat* (2002) 19(4):343-60; and McGail et al., *Adv Biochem Eng Biotechnol* (2002) 77:21-42.

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of arrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length.

Computer-Implemented Methods, Systems and Devices

Any of the methods described herein may be totally or partially performed with a computer system including one or more processors, which can be configured to perform the steps. Thus, embodiments are directed to computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Any of the steps of any of the methods can be performed with modules, circuits, or other means for performing these steps.

Any of the computer systems mentioned herein may utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. The subsystems can be interconnected via a system bus. Additional subsystems include, for examples, a printer, keyboard, storage device(s), monitor, which is coupled to display adapter, and others. Peripherals and input/output (I/O) devices, which couple to I/O controller, can be connected to the computer system by any number of means known in the art, such as serial port. For example, serial port or external interface (e.g. Ethernet, Wi-Fi, etc.) can be used to connect computer system to a wide area network such as the Internet, a mouse input device, or a scanner. The interconnection via system bus allows the central processor to communicate with each subsystem and to control the execution of instructions from system memory or the storage device(s) (e.g., a fixed disk, such as a hard drive or optical disk), as well as the exchange of information between subsystems. The system memory and/or the storage device(s) may embody a computer readable medium. Any of the data mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure can be implemented in the form of control logic using hardware (e.g., an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1

Materials and Methods
Nucleic Acid Extraction
Genomic DNA from cells, PDXs and PDXOs was purified using DNeasy Blood & Tissue Kit (QIAGEN, Cat. 69506, CA) according to the manufacturer's instructions. DNA integrity was determined by 2100 Bioanalyser (Agilent) and quantified using the NanoDrop (Thermo Scientific). One aliquot of high-quality DNA sample (OD260/280=1.8~2.0, OD260/230≥2.0, >1 µg) was used for the deep NGS sequencing and WES sequencing. Total RNA from cells, PDXs and PDXOs was purified using RNeasy Mini Kit (QIAGEN, Cat. 74106, CA) according to the manufacturer's instructions. Integrity of the total RNA was determined by 2100 Bioanalyser (Agilent) and quantified using the NanoDrop (Thermo Scientific). One aliquot of high-quality RNA sample (OD260/280=1.8~2.2, OD260/230≥2.0, RIN≥8.0, >1 µg) was used for the deep NGS sequencing and RNAseq sequencing.

Cell Line Mixture Preparation
A cell line mixture was prepared by mixing cells from two cell lines with given ratios. Based on cell growth rate, cells were seeded in 15 ml medium in T75 that allowed cell confluence to reach 60%-80%, followed by overnight incubation at $CO_2$ Water Jacketed Incubator (SANYO). Cells were harvested during the logarithmic growth period, and counted with hemocytometer (Chongguang) for the calculation of concentration. Cells from two cell lines were then mixed according to predefined ratios to create a cell line mixture that was subsequently centrifuged at 3,000 rpm for 5 minutes. Supernatant was aspirated and cell pellets were stored at −20° C. for DNA extraction.

Human-Mouse DNA Mixture Preparation
A serial of mouse-human DNA mixture benchmark samples were prepared by mixing mouse spleen DNA and human genomic DNA (Thermo Scientific, Cat. 4312660). Mouse spleen DNA was purified using DNeasy Blood & Tissue Kit (QIAGEN, Cat. 69506, CA) according to the manufacturer's instructions and quantified using the NanoDrop (Thermo Scientific). Mouse spleen DNA and human genomic DNA were diluted to 200 ng/µL, then mixed by predefined ratios. The DNA mixture was used for the deep NGS sequencing later.

Barcode Deep NGS Sequencing
Multiplex PCR was used to prepare target sequencing libraries for Illumina sequencers with a paired-end read length of 150 bp (pE150). The NGS deep sequencing covered 630 amplicons, sizes of which ranged from 160 bp to 260 bp. Genomic DNA was amplified by using IGT-EM808 polymerase mixture (iGene TechBioscience Co., Ltd, 95° C. for 3 min 30 secs, 18 cycles of incubation at 98° C. for 20 secs and 60° C. for 8 min, hold at 72° C. for 5 min) and then purified by AMPure XP beads (Beckman, Cat. A63881).

Barcoding was executed by a second round of amplification. Briefly, purified target amplicons were taken as templates and added with upstream IGT-I5 index (10 µM), downstream IGT-I7 index (10 µM) and polymerase mixture for PCR reaction. The mixture was then placed in a thermal cycler for amplification with the following settings: 95° C. for 3 min 30 secs, 9 cycles of incubation at 98° C. for 20 secs, 58° C. for 1 min and 72° C. for 30 secs, hold-on at 72° C. for 5 min. The barcoded library was then purified by using AMPure XP beads (Beckmen, Cat. A63881).

After library construction, Qubit 3.0 fluorometer dsDNA HS Assay (Thermo Fisher Scientific) was used to quantify concentrations of the resulting sequencing libraries. Agilent BioAnalyzer 2100 (Agilent) was used to analyze size distribution ranging from 280 bp to 420 bp. Paired-end sequencing was performed using an Illumina system following Illumina-provided protocols for 2×150 bp paired-end sequencing.

RNAseq and WES Sequencing

In RNAseq sequencing, the mRNA-focused sequencing libraries were constructed from total RNA. Poly-A mRNA was purified from total RNA using oligo-dT-attached magnetic beads and then fragmented by fragmentation buffer. Using the short fragments as templates, first stranded cDNA was synthesized using reverse transcriptase and random primers, followed by second stranded cDNA synthesis. Then the synthesized cDNA was subjected to end-repair, phosphorylation and 'A' base addition according to library construction protocol. Then sequencing adapters were added to both ends of the cDNA fragments. After PCR amplification for cDNA fragments, the targeted 250-350 bp fragments were cleaned up. After library construction, Qubit 3.0 fluorometer dsDNA HS Assay (Thermo Fisher Scientific) was used to quantify concentrations of the resulting sequencing libraries, while the size distribution was analyzed using Agilent BioAnalyzer 2100 (Agilent). After library validation, Illumina CBOT cluster generation system with HiSeq PE Cluster Kits (Illumina) was used to generate clusters. Paired-end sequencing was performed using an Illumina system following Illumina-provided protocols for 2×150 paired-end sequencing.

WES was performed by Wuxi Nextcode Co. Ltd. (Shanghai, China). Briefly, genomic DNA was extracted and fragmented to an average size of 180-280 bp. DNA libraries were generated by Illumina's manufacturer paired-end protocols. Exons were captured by Agilent SureSelect Human All Exon V6, and subsequently sequenced by the Illumina NovaSeq platform (Illumina Inc., San Diego, Calif., USA) to generate 150 bp paired-end reads.

SNP Selection and Profiling

The inventors selected a panel SNPs for human sample authentication by several criteria: 1) SNPs are in exons, 2) SNPs are located on all 22 autosomes and are sufficient away from each other since chromosome abnormality, including deletions and duplications of large chromosome segments, are common in tumors, 3) SNPs are in highly expressed genes, 4) the minor allele frequency (MAF) of a SNP is close to 0.5 in 3 reference populations of the International HapMap Project, namely Han Chinese (CHB), Nigeria Yoruba (YRI) and Utah residents with Northern and Western European ancestry from the CEPH collection (CEU).

Benchmark Samples and Data

Two cell line benchmark sample sets were prepared. The first set has 78 samples for 3 pairs of cell lines including PANC-1 and RT4, MV-4-11 and "LNCaP clone FGC", CAL27 and Raji. Each pair has 26 samples including the pure two cell lines and 3 replicates for 8 mix ratios by cell count (Supp. Table S2). The second set has 22 cell lines each contaminated by a known second cell line by a mostly small but unspecified ratio (Supp. Table S3).

Estimating Heterogeneity Ratios

There are six informative genotype combinations that can be used to estimate heterogeneity ratios from the deep NGS sequencing data (Table 11). They exhibit four distinct nucleotide frequency patterns. Combinations 1 and 2 generate the same pattern, and we use an average formula to calculate the percentage of the minor component S2, or the heterogeneity ratio. The formula produces an exact estimate of the ratio when the two combinations occur with equal frequency, a scenario that should be closely approximated when the number of SNPs is large. Similar averaging approach is used for Combinations 4 and 5. When the heterogeneity ratio is low, sequencing error may interfere the inference of heterogeneity ratio. To alleviate this, we use a 2-step statistical procedure. Assuming sequencing error is $e=0.001$ and the sequencing depth is n ($n \geq 500$, any SNP with $n<500$ is discarded) at a given SNP site, the probability of observing k erroneous nucleotides follows a binomial distribution with parameters n and e.

$$f(k, n, e) = \binom{n}{k} e^k (1-e)^{n-k}$$

For each n, we calculate the cumulative density function and obtain a threshold h so that the probability of observing more than h erroneous nucleotides out of the n nucleotides is smaller than 0.01. In the sequencing data, any low-frequency nucleotide with number of reads smaller than a corresponding threshold h is discarded. We then use an Expectation-Maximization algorithm (package mclust in R, version 3.5.3 (Team, R. C. R: A language and environment for statistical computing. 3.5.3 edn (R Foundation for Statistical Computing, Vienna, Austria, 2018))) to estimate parameters of a Gaussian mixture (with 1 to 3 components) that models the distribution of nucleotide frequencies smaller than a maximal heterogeneity (0.2 used for all samples in this study). If there is only a single Gaussian component or the Gaussian component with smallest mean accounts for more than 60% of all data points, median of all data points is taken as the sample heterogeneity ratio, otherwise, median of data points in the other Gaussian component(s) is taken as the sample heterogeneity ratio.

Determining Major Component of a Sample

The genotype at a SNP site is determined using only nucleotides with allele frequencies larger than a threshold, 10% for reference samples and 25% for test samples which may be contaminated. The genotype similarity between a reference sample and a test sample is the percentage of SNPs with identical genotypes, excluding SNPs with sequencing depth less than 500 in the test sample. The major component of the test sample is the reference sample with the highest genotype similarity, which must be greater than 90% (or 80%) if the heterogeneity ratio of the test sample is <10% (or >10%). Otherwise, no major component is called.

Determining Minor Component of a Sample

After the estimation of heterogeneity ratio and determination of major component, we determine the minor component of a test sample. For a mixture of the major component and one of the other reference samples (e.g., all cell lines with genomic data), we obtain a chimeric genotype, with possibly 1 to 4 nucleotides, at every SNP site. Frequencies of nucleotides are calculated using the heterogeneity ratio. Similarly, we get the chimeric genotype of the test sample. The two chimeric genotypes are considered identical if they harbor same nucleotides and frequencies of each nucleotide are within three folds. We then calculate the genotype similarity between the test sample and each reference sample combined with the major component. The set of all pairwise genotype similarities are then fitted by a beta distribution with parameters $(\alpha, \beta)$ $$f(x, \alpha, \beta) = \frac{\Gamma(\alpha+\beta)}{\Gamma(\alpha)\Gamma(\beta)} x^{\alpha-1}(1-x)^{\beta-1}$$

In the equation, $\Gamma(\alpha)$ is the gamma function, x is genotype similarity. Its parameters were estimated by package fitdistrplus in R (version 3.5.3). From the fitted beta distribution we then calculated the probability of observing any genotype similarity larger than a specific value. A quantile-quantile graph with 99% confidence band was plotted for all observed genotype similarities for visualization. A reference sample was considered the minor component if (1) it has the highest genotype similarities, (2) its genotype similarity is above the 99% confidence upper bound in the quantile-quantile graph, and (3) its p-value<1.0E-6 in the fitted beta distribution.

Estimating Mixture Ratio of Two Cell Lines

Cell lines are used to explain the estimation of mix ratio for two reference samples. Assume that two cell lines S1 and S2 are mixed with ratio θ for S1 and (1-θ) for S2 where From deep NGS sequencing data, nucleotide frequencies of all n SNPs in both cell lines can be accurately estimated. For a SNP, its four nucleotide frequencies are denoted, which sum to 1, as $\{A_1, T_1, G_1, C_1\}$ for cell line S1 and $\{A_2, T_2, G_2, C_2\}$ for cell line S2. In principle, one of the frequencies is close to 1 if the SNP is homozygous, and two frequencies are both close to 0.5 if the SNP is heterozygous. Actual data may have some deviations due to sequencing errors and randomness, as well as multiclonality of cell lines.

From sequencing data of the mix sample, the actual occurrences of the four nucleotides are denoted as $x=\{n_A, n_T, n_G, n_C\}$. The likelihood of such observation is $$\mathcal{L}(\theta|x) = P_\theta(x) = const \times \Pi_{ME\{A,T,G,C\}}(\theta M_1 + (1-\theta)M_2)^{n_M}$$

The likelihood $P_\theta(x_i)$ can be calculated for any SNP $i \in (1, 2, \ldots, n)$ with observed data $x_i$, the likelihood of observing data $X=\{x_1, x_2, \ldots, x_n\}$ for all SNPs is $$\mathcal{L}(\theta|X) = const \times \prod_{i=1}^{n} P_\theta(x_i)$$

The log-likelihood is therefore $$\log \mathcal{L}(\theta|X) = \sum_{i=1}^{n} \log P_\theta(x_i)$$

θ that maximizes the likelihood can then be solved by stepwise increment of θ. The above procedure can be used for mixture of any two human samples as well.

Simulation of Cell Line Mixture for Contaminant Detection

Simulation was performed for 3 cell line pairs including PANC-1 and RT4, MV-4-11 and "LNCaP clone FGC", CAL27 and Raji. All six cell lines were profiled by deep NGS sequencing to obtain their SNP fingerprints. Two cell lines in a pair were mixed in silico where ratio of the first cell line is r, and r takes the following values: 0.15%, 0.30%, 0.625%, 1.25%, 2.5%, 5%, 10%, 15%, and 20%. For each SNP site, r×n nucleotides were obtained from the first cell line where n was a random integer from 500 to 5000, r×n were further distributed into 4 nucleotides (A, T, G, C) according to their frequencies in the first cell line. Similarly, (1−r)×n nucleotides were obtained from the second cell line. The ratio was then reversed so a symmetric sampling was done with ratio r for the second cell line.

Estimating Mouse Ratio from RNAseq and WES Datasets

Sequencing reads were mapped to human (hg19) and mouse (mm10) genomes using mapping tools STAR (Dobin, A. et al. STAR: ultrafast universal RNA-seq aligner. *Bioinformatics* 29, 15-21 (2013)) for RNAseq data and BWA (Li, H. & Durbin, R. Fast and accurate short read alignment with Burrows-Wheeler transform. *Bioinformatics* 25, 1754-60 (2009)) for WES data with default parameters. If a read was only mapped to human genome, or had fewer mismatches to human genome than to mouse genome, it was classified as human read. Mouse reads were similarly assigned. If a read was mapped to both genomes with close number of mismatches, off by at most 2, the read was unclassifiable and discarded. The mouse ratio was the proportion of mouse reads out of all kept reads.

Example 2

This example illustrates the human sample authentication and contamination detection.

SNP Profiling and Fingerprint

A panel of SNPs were selected for authenticating human samples including cell lines, xenografts and organoids (Table 1). SNPs were profiled by deep NGS sequencing with an average depth of 3000. Each sample has a unique SNP fingerprint consisted of both nucleotide identities and frequencies for all the SNPs. It shall be emphasized that a cell line can have fluctuating SNP fingerprints between passages and among biobanks due to genetic drift and heterogeneity, so a current SNP fingerprint can be profiled for better curation. The SNP fingerprints can be generated, with reduced precision, by relatively low-depth NGS data. In this example, the inventors generated SNP fingerprints for 1050 cell lines from RNAseq data profiled by the inventors and CCLE, which serve as references.

The inventors illustrated the authentication, characterization, intraspecies and interspecies contamination detection using SNP profiling data from deep NGS sequencing for 217 cell line samples, 220 PDX and 31 PDX-derived organoid (PDXO) samples. For the cell line samples, the inventors tested the mixtures of two cell lines with known mix ratios from serial dilutions and 6 corresponding pure cell lines (Table 7), the mixtures of two cell lines with unknown mix ratios (Table 8), and 117 unmixed cell lines (Table 9).

Authentication of Human Samples

Identity of a sample, or the major component of a contaminated sample, was determined by its genotype similarity to a library of reference samples. In 217 tested cell line samples, genotype similarities between same cell lines were always >90% with an average of 98.6%, and the lowest was 91.7% for an A-875 cell culture with 16.7% contamination of JEG-3 (FIG. 1A, Table 8). In contrast, genotype similarities between unrelated cell lines were almost always below 50%. Still there were cell lines that are closely related or in the same synonymous group by various reasons including mislabeling, contamination, deriving from same patient, one cell line being parental to another, etc. For example, HCT-15 and HCT-8 likely were derived from the same patient; QGY-7701 is contaminated and a HeLa derivative. Genotype similarities for 16 such cell line pairs in the dataset range from 84% to 96% (Table 10). These cell line pairs can be distinguished except for almost identical ones such as HLE and HLF. Genotype similarities between same models on average are 98.0% (87.2~100%) for 220 PDX and 31 PDX-derived organoid (PDXO) samples, and nearly all are below 50% between different models.

Estimation of Genetic Heterogeneity

If a sample is uncontaminated and is purely monoclonal diploid, then a SNP site is either homozygous or heterozygous, and the observed nucleotide frequency is close to 1 or 0.5 in deep NGS sequencing data, difference only coming from errors and randomness in sequencing. In reality, cell lines may have minor clones, are aneuploid or are contaminated (contaminants), so not only did the inventors observe frequencies far away from 0.5 and 1, but also 3 or 4 nucleotides at a SNP site. Such information can be used to estimate genetic heterogeneity of a sample.

The dominant clone is the major component of a sample, minor clones and contaminants are the minor component. There are six informative genotype combinations of the major and minor components that can be used to estimate SNP heterogeneity ratios, based on the four observed nucleotide frequency patterns (Table 11). A SNP site is informative if it emits one of the four patterns. Subsequently, sample heterogeneity ratio is estimated from individual SNP heterogeneity ratios by a statistical modeling approach (see Example 1). Using the test samples, the inventors found that uncontaminated cell lines on average have 107 informative SNP sites, while contaminated cell lines have a slightly more 112. On average, PDX and PDXO models have 156 and 111 informative SNP sites, respectively, which reflects higher genetic heterogeneity and/or mouse contamination in PDX models.

Detection and Quantification of Contamination

Figure 1B:
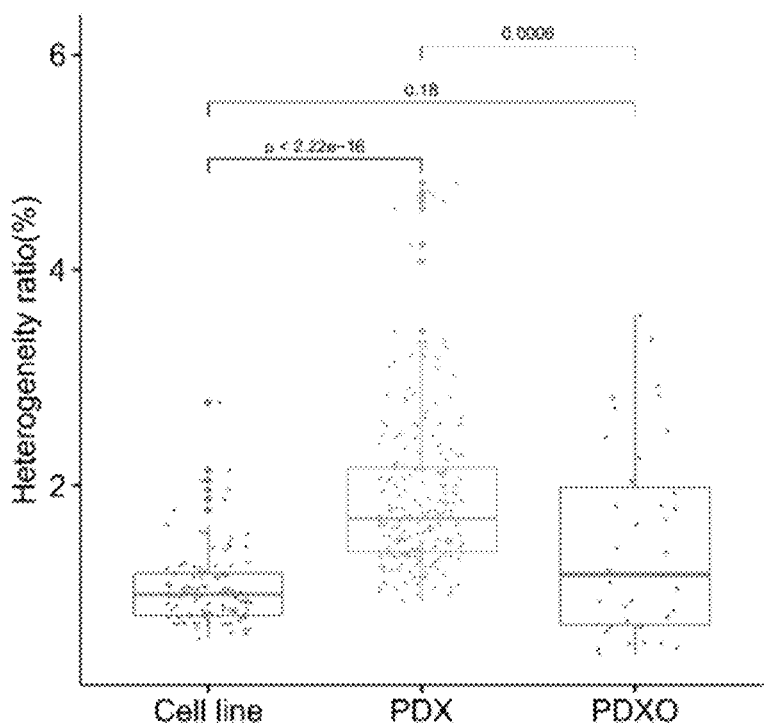
Figure 1C:
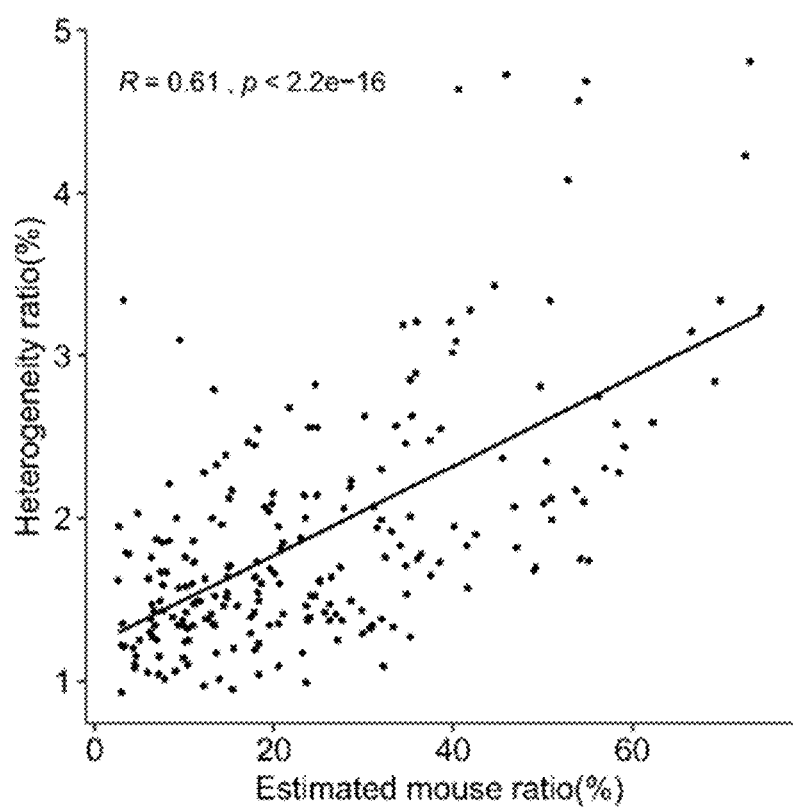
Figures 2A, 2B, 2C, 2D, 2E, 2F:
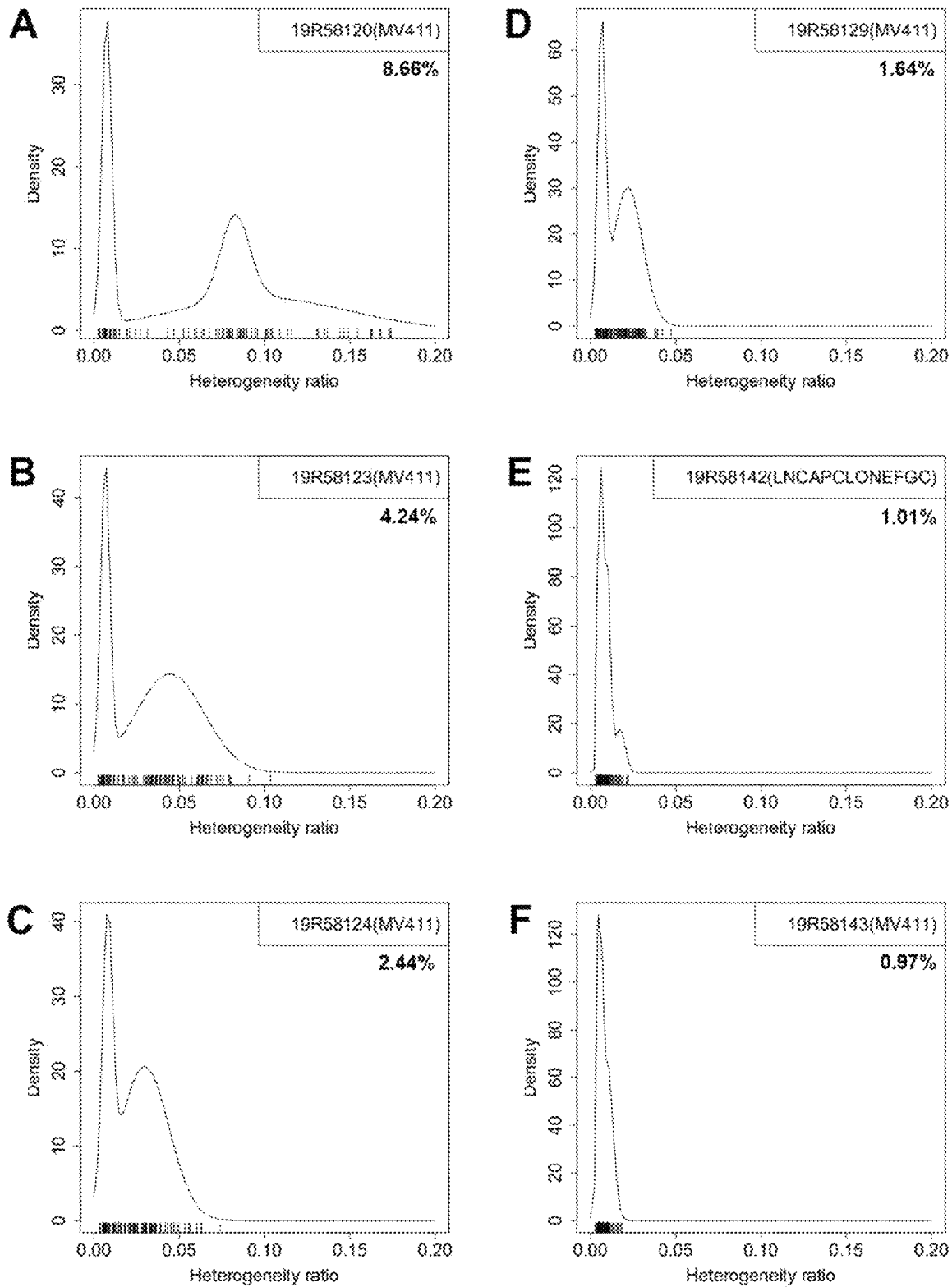
FIG. 2A-2D show that the heterogeneity ratio can be used to detect and quantify contamination.
FIG. 2E: pure LNCaP clone FGC cell line.
FIG. 2F: pure MV-4-11 cell line. Each tick above the horizontal axis represents an informative SNP site with corresponding SNP heterogeneity ratio. Probability density was estimated by assuming a 2/3-component Gaussian mixture. Sample serial number is labeled in the top-right box with the major component cell line in parenthesis. Sample heterogeneity ratio is shown underneath.

The inventors detected sample contamination by combining three analyses. First, contaminated samples can have high heterogeneity ratios, while uncontaminated ones do not. In the test samples, 115 of 118 (97.5%) presumably uncontaminated cell lines have heterogeneity ratios <2% and all <3% (FIG. 1B). In contrast, the inventors observed high heterogeneity ratios for contaminated cell lines, for example, an A-875 cell culture mixed with JEG-3 cell had heterogeneity ratio 15.5% (Table 8). As shown supra, heterogeneity ratio is proportional to contamination ratio (percentage of contaminants), and therefore is a good indicator for contamination. Human tumors dissected from PDX models contain mouse stroma, and indeed the inventors observed higher heterogeneity ratios in PDX tumors (FIG. 1B), caused by mouse contamination (FIG. 1C). PDXOs, as in vitro culture of PDXs, have significantly smaller heterogeneity ratios due to much smaller and often only trace amount of mouse cells (FIG. 1B).

Contamination was also indicated by a distinct right peak in the probability density of SNP heterogeneity ratios for a sample (FIG. 2A-2F). The peak shifted right as contamination and heterogeneity ratio increase, and sometimes splits into two peaks. The bi/tri-modal distribution vanished or only marginally showed up for uncontaminated cell lines or cell lines with very low contamination ratios (<1%) and heterogeneity ratios (<2%).

Figure 3A:
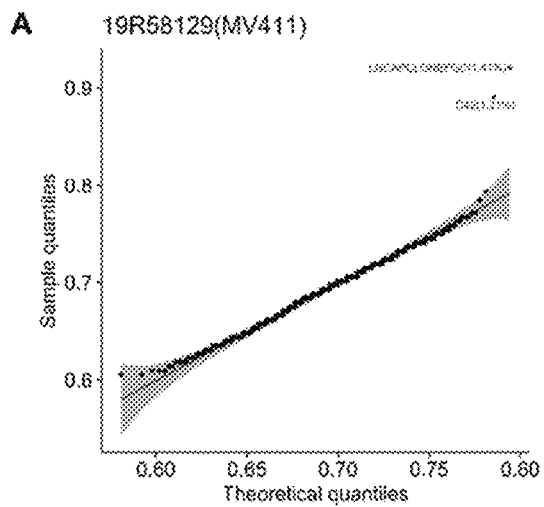
FIG. 3A-3F show the contamination detection, contaminant inference and contamination ratio estimation.
Figure 3B:
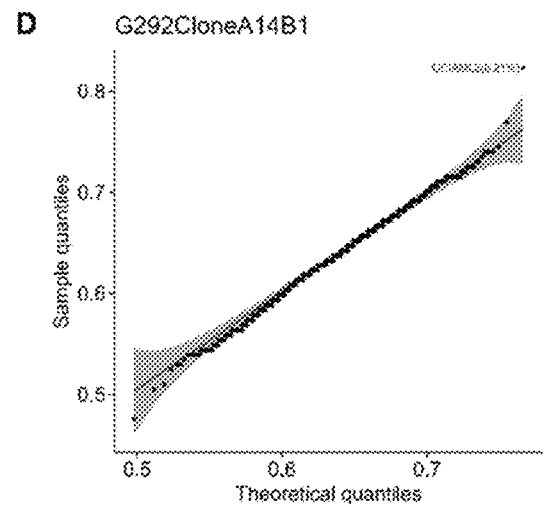
Figure 3C:
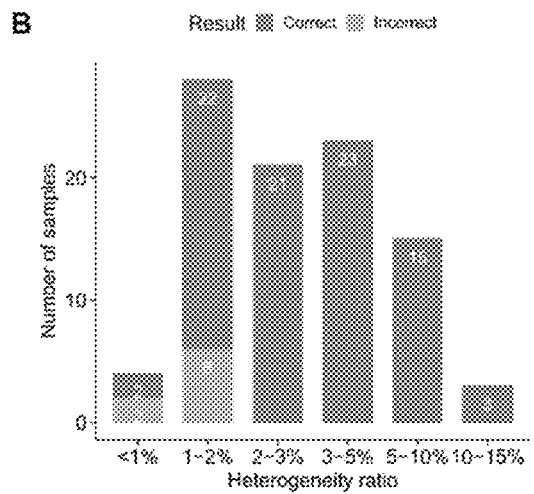
Figure 3D:
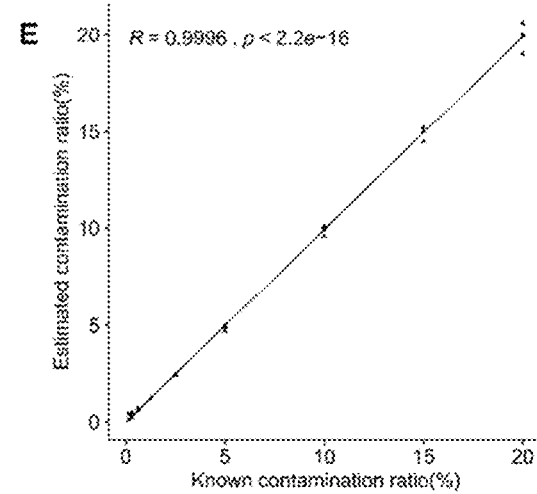

Finally, contaminants can be directly detected by statistical modeling that gives intuitive visualization and rigorous probabilistic measurement (see Example 1, FIG. 3A). In 94 cell line samples each mixed with another cell line, the inventors can always correctly infer the minor contaminant cell line in a cell line when the heterogeneity ratio is ≥2% (FIG. 3B). Accuracy goes down to about 80% and 50% when the heterogeneity ratio is 1-2% and <1%. For the 8 missed samples, seven samples were characterized as clean and only one was marked by a wrong contaminating cell line. Of course, such inference is only feasible when the contaminating cell line is also one with known SNP fingerprint. The inventors detected several contaminated cell lines in our biobank, one example is cell line "G-292 clone A141B1" which had a high heterogeneity ratio of 7.62% (FIG. 3C), and it was contaminated by 6.21% OCI-AML-2 (FIG. 3D).

Figure 3E:
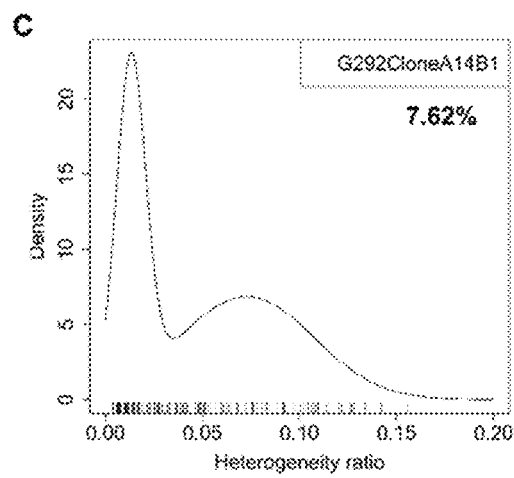
Figure 3F:
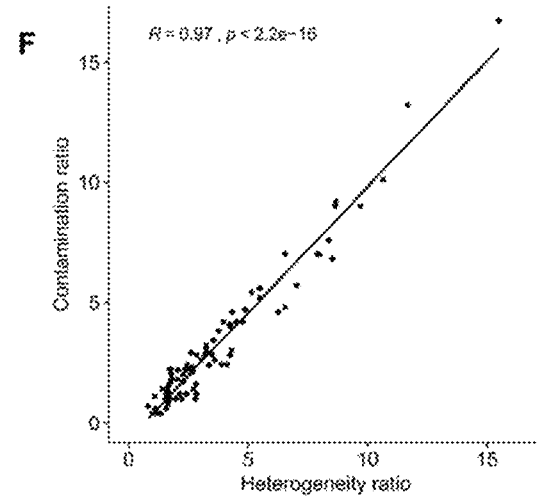

After identifying the contaminating cell line, the inventors can estimate the contamination ratio (i.e. percentage of the second cell line) using a maximum-likelihood approach (see Example 1). Simulation studies showed that the estimated contamination ratios are extremely close to known ratios (FIG. 3E). The inventors observed a tight linear correlation between heterogeneity ratios and contamination ratios (FIG. 3F). Therefore, as discussed before, heterogeneity ratio is a good estimator of contamination, and is particularly useful when contaminants are not standard cell lines. Still in contaminated samples, contaminants contributed only part, though sometimes majority, of the genetic heterogeneity, consequently contamination ratios were generally smaller than corresponding heterogeneity ratios (see Table 8), the few violations were caused by data processing methods.

In summary, heterogeneity ratio, by its value and distribution, is a reliable contamination measure for human samples. Cell line samples with heterogeneity ratio 2% are highly likely contaminated, and when the contaminant is another cell line also with SNP fingerprint information, its identity can be inferred and the contamination ratio can be estimated with an unprecedented sensitivity at measured by cell or DNA mix ratios (Table 7 and 8).

Example 3

This example illustrates the mouse tumor model authentication.

A panel of mouse SNPs (see Table 2) were selected for authenticating 32 syngeneic mouse tumor models commonly used in preclinical immunomodulatory drug development, including 4T1, A20, B16-BL6, B16-F0, B16-F1, B16-F10, C1498, Colon26, CT26WT, E.G7-Ova, EL4, EMT6, H22, Hepa1-6, J558, J774A1, JC, KLN205, L1210, L5178-R, LLC, MBT2, MC38, MPC-11, Neuro-2a, P388D1, P815, Pan02, Renca, RM1, S91, and WEHI164. Most models have 6 unique SNPs. Colon26 and CT26WT are mouse colon adenocarcinoma models originated from BALB/c mouse strain, each has 12 SNPs with 6 common ones for a total of 18 unique ones. B16-BL6, B16-F0, B16-F1, and B16-F10 are mouse melanoma cell lines in C57BL/6 mouse strain and were all derived from B16 thus share high genetic similarity. Specifically, B16 is the parental line of B16-F0, which in turn is the parental line of B16-F1. B16-F10 is the 10th serial passage of B16-F0 and is the parental line of B16-BL6[46]. The inventors used 7 common SNPs to first assign a test cell line into this group, then to B16-BL6, B16-F0 and B16-F10 each with 6 unique SNPs, and when none of the 18 SNPs is observed, the test cell line is assigned B16-F1. Authentication on these model models achieved 100% accuracy.

Example 4

This example illustrates the human-mouse interspecies contamination detection.

Figures 4A, 4B, 4C, 4D:
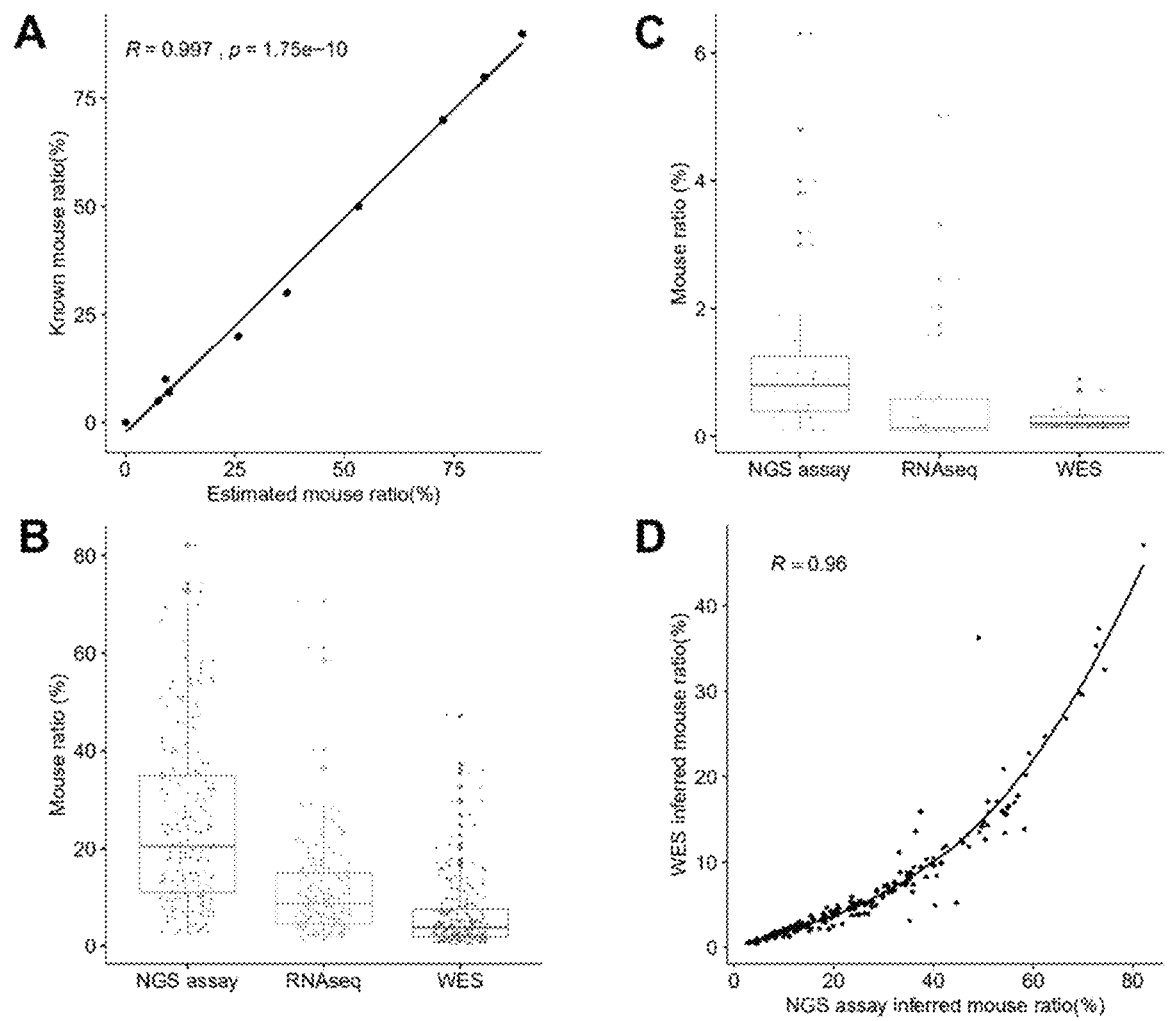
FIG. 4A-4D show the estimation of mouse ratio in human-mouse mixtures.

The inventors compared human hg19 and mouse mm10 genomes, and identified a group of 100-300 bp segments (see Table 3) such that each segment significantly diverged—by insertion, deletion and point mutation—between human and mouse (31-97% sequence similarities), yet has identical flanking sequences so that a common pair of primers can be designed. After NGS sequencing, the inventors separated human and mouse reads, calculated mouse ratios for all segments, and took median of these ratios as the mouse ratio in a human-mouse mixed sample. This method demonstrated extremely high accuracy in a set of benchmark samples in which mouse and human DNA was mixed by serial dilutions (FIG. 4A). The inventors also developed methods of estimating mouse content from RNAseq and WES data (see Example 1). The inventors compared three methods in estimating mouse ratios in 220 PDX and 31 PDXO models (FIG. 4B-C). DNA (for WES and the deep NGS sequencing) and RNA (for RNAseq) were extracted and sequenced from same sample of a model to remove sample variance. PDXO models generally had low mouse content. In PDX models, mouse ratios accurately estimated from deep NGS sequencing data were the highest, followed by RNAseq then WES. This is mainly because the exon-capture kit used in WES was designed to enrich human exons and had low hybridization affinity to homologous mouse exons. RNAseq used polyA-enrichment protocol with no species preference but gene expression has great temporospatial variability in human tumor and mouse stroma of PDX. Indeed, the inventors observed a very strong quadratic relationship for mouse ratios between the deep NGS sequencing data and WES data (R=0.96, FIG. 4D), but a much weaker linear correlation between the deep sequencing data and RNAseq data (R=0.62).

Example 5

This example illustrates the detection of mycoplasma in the samples.

The inventors used one pair of universal primers for the detection of all mycoplasma species, and 11 pairs for detecting 11 mollicutes including *A. laidlawii, M. arginine, M. fermentans, M. genitalium, M. hominis, M. hyorhinis, M. orale, M. pneumonia, M. salivarium*, and *U. urealyticum* with proven effectiveness (Molla Kazemiha, V. et al. *Cytotechnology* 61, 117-24 (2009)). The inventors identified one mycoplasma contaminated cell line in the biobank by the deep NGS sequencing method and subsequently validated it by a mycoplasma detection kit.

Example 6

This example illustrates the population structure analysis and gender determination.

Of the panel of SNPs used for human sample authentication, 143 were characterized by the International HapMap Project (International HapMap, C. The International HapMap Project. *Nature* 426, 789-96 (2003)). The inventors used fastSTRUCTURE (Raj, A., Stephens, M. & Pritchard, J. K. *Genetics* 197, 573-89 (2014)) to perform population structure analysis of three reference populations: Han Chinese (CHB), Nigeria Yoruba (YRI) and Utah residents with Northern and Western European ancestry from the CEPH collection (CEU). All 406 individuals were unambiguously assigned with high probabilities. The inventors then profiled 423 PDX models derived from East Asian patients and 634 PDX models derived from Western patients in the U.S. All the East Asian PDX models have dominant CHB composition with only one exception. Majority of the Western PDX models have predominantly CEU composition, the rest have major CHB or YRI compositions or mixture of two or three of the reference populations. The inventors also used 3 SNPs at Y chromosome for gender inference (Table 3), which was always accurate except for tumor samples with lost Y chromosome.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

REFERENCES

1. Identity crisis. *Nature* 457, 935-6 (2009).
2. American Type Culture Collection Standards Development Organization Workgroup, A. S. N. Cell line misidentification: the beginning of the end. *Nat Rev Cancer* 10, 441-8 (2010).
3. Capes-Davis, A. et al. Match criteria for human cell line authentication: where do we draw the line? *IntJCancer* 132, 2510-9 (2013).
4. Gartler, S. M. Apparent Hela cell contamination of human heteroploid cell lines. *Nature* 217, 750-1 (1968).
5. Lacroix, M. Persistent use of "false" cell lines. *Int J Cancer* 122, 1-4 (2008).
6. Lorsch, J. R., Collins, F. S. & Lippincott-Schwartz, J. Cell Biology. Fixing problems with cell lines. *Science* 346, 1452-3 (2014).
7. Fusenig, N. E., Capes-Davis, A., Bianchini, F., Sundell, S. & Lichter, P. The need for a worldwide consensus for cell line authentication: Experience implementing a mandatory requirement at the International Journal of Cancer. *PLoS Biol* 15, e2001438 (2017).
8. Yu, M. et al. A resource for cell line authentication, annotation and quality control. *Nature* 520, 307-11 (2015).
9. Bian, X., Yang, Z., Feng, H., Sun, H. & Liu, Y. A Combination of Species Identification and STR Profiling Identifies Cross-contaminated Cells from 482 Human Tumor Cell Lines. *Sci Rep* 7, 9774 (2017).
10. Horbach, S. & Halffman, W. The ghosts of HeLa: How cell line misidentification contaminates the scientific literature. *PLoS One* 12, e0186281 (2017).
11. de Maagd, R. A. et al. Identification of *Bacillus thuringiensis* delta-endotoxin Cry1C domain III amino acid residues involved in insect specificity. *Appl Environ Microbiol* 65, 4369-74 (1999).
12. Azari, S., Ahmadi, N., Tehrani, M. J. & Shokri, F. Profiling and authentication of human cell lines using short tandem repeat (STR) loci: Report from the National Cell Bank of Iran. *Biologicals* 35, 195-202 (2007).
13. Wu, M. L. et al. A 2-yr service report of cell line authentication. *In Vitro Cell Dev Biol Anim* 49, 743-5 (2013).
14. Masters, J. R. HeLa cells 50 years on: the good, the bad and the ugly. *Nat Rev Cancer* 2, 315-9 (2002).
15. MacLeod, R. A. et al. Widespread intraspecies cross-contamination of human tumor cell lines arising at source. *Int J Cancer* 83, 555-63 (1999).
16. Cosme, B. et al. Are your results valid? Cellular authentication a need from the past, an emergency on the present. In *Vitro Cell Dev Biol Anim* 53, 430-434 (2017).
17. Ye, F., Chen, C., Qin, J., Liu, J. & Zheng, C. Genetic profiling reveals an alarming rate of cross-contamination among human cell lines used in China. *FASEB J* 29, 4268-72 (2015).
18. Freedman, L. P. et al. The culture of cell culture practices and authentication—Results from a 2015 Survey. *Biotechniques* 59, 189-90, 192 (2015).
19. Nims, R. W. & Reid, Y. Best practices for authenticating cell lines. *In Vitro Cell Dev Biol Anim* 53, 880-887 (2017).
20. Almeida, J. L., Cole, K. D. & Plant, A. L. Standards for Cell Line Authentication and Beyond. *PLoS Biol* 14, e1002476 (2016).
21. Almeida, J. L. et al. Interlaboratory study to validate a STR profiling method for intraspecies identification of mouse cell lines. *PLoS One* 14, e0218412 (2019).
22. Zaaijer, S. et al. Rapid re-identification of human samples using portable DNA sequencing. *Elife* 6(2017).
23. Yousefi, S. et al. A SNP panel for identification of DNA and RNA specimens. *BMC Genomics* 19, 90 (2018).

24. Jobling, M. A. & Gill, P. Encoded evidence: DNA in forensic analysis. *Nat Rev Genet* 5, 739-51 (2004).
25. Sanchez, J. J. et al. A multiplex assay with 52 single nucleotide polymorphisms for human identification. *Electrophoresis* 27, 1713-24 (2006).
26. Didion, J. P. et al. SNP array profiling of mouse cell lines identifies their strains of origin and reveals cross-contamination and widespread aneuploidy. *BMC Genomics* 15, 847 (2014).
27. Liang-Chu, M. M. et al. Human biosample authentication using the high-throughput, cost-effective SNPtrace™ system. *PLoS One* 10, e0116218 (2015).
28. Pengelly, R. J. et al. A SNP profiling panel for sample tracking in whole-exome sequencing studies. *Genome Med* 5, 89 (2013).
29. Morgan, A. P. et al. The Mouse Universal Genotyping Array: From Substrains to Subspecies. G3 (*Bethesda*) 6, 263-79 (2015).
30. Castro, F. et al. High-throughput SNP-based authentication of human cell lines. *Int J Cancer* 132, 308-14 (2013).
31. El-Hoss, J. et al. A single nucleotide polymorphism genotyping platform for the authentication of patient derived xenografts. *Oncotarget* 7, 60475-60490 (2016).
32. Ruitberg, C. M., Reeder, D. J. & Butler, J. M. STRBase: a short tandem repeat DNA database for the human identity testing community. *Nucleic Acids Res* 29, 320-2 (2001).
33. van der Meer, D. et al. Cell Model Passports-a hub for clinical, genetic and functional datasets of preclinical cancer models. *Nucleic Acids Res* 47, D923-D929 (2019).
34. Tuveson, D. & Clevers, H. Cancer modeling meets human organoid technology. *Science* 364, 952-955 (2019).
35. Day, C. P., Merlino, G. & Van Dyke, T. Preclinical mouse cancer models: a maze of opportunities and challenges. *Cell* 163, 39-53 (2015).
36. Guo, S. et al. Molecular Pathology of Patient Tumors, Patient-Derived Xenografts, and Cancer Cell Lines. *Cancer Res* 76, 4619-26 (2016).
37. Khaled, W. T. & Liu, P. Cancer mouse models: past, present and future. *Semin Cell Dev Biol* 27, 54-60 (2014).
38. Li, Q. X., Feuer, G., Ouyang, X. & An, X. Experimental animal modeling for immuno-oncology. *Pharmacol Ther* 173, 34-46 (2017).
39. Chao, C. et al. Patient-derived Xenografts from Colorectal Carcinoma: A Temporal and Hierarchical Study of Murine Stromal Cell Replacement. *Anticancer Res* 37, 3405-3412 (2017).
40. Fasterius, E. & Al-Khalili Szigyarto, C. Analysis of public RNA-sequencing data reveals biological consequences of genetic heterogeneity in cell line populations. *Sci Rep* 8, 11226 (2018).
41. Ghandi, M. et al. Next-generation characterization of the Cancer Cell Line Encyclopedia. *Nature* 569, 503-508 (2019).
42. Vermeulen, S. J. et al. Did the four human cancer cell lines DLD-1, HCT-15, HCT-8, and HRT-18 originate from one and the same patient? *Cancer Genet Cytogenet* 107, 76-9 (1998).
43. Rebouissou, S., Zucman-Rossi, J., Moreau, R., Qiu, Z. & Hui, L. Note of caution: Contaminations of hepatocellular cell lines. *J Hepatol* 67, 896-897 (2017).
44. Barretina, J. et al. The Cancer Cell Line Encyclopedia enables predictive modelling of anticancer drug sensitivity. *Nature* 483, 603-7 (2012).
45. Bairoch, A. The Cellosaurus, a Cell-Line Knowledge Resource. *J Biomol Tech* 29, 25-38 (2018).
46. Molla Kazemiha, V. et al. PCR-based detection and eradication of mycoplasmal infections from various mammalian cell lines: a local experience. *Cytotechnology* 61, 117-24 (2009).
47. International HapMap, C. The International HapMap Project. *Nature* 426, 789-96 (2003).
48. Raj, A., Stephens, M. & Pritchard, J. K. fastSTRUCTURE: variational inference of population structure in large SNP data sets. *Genetics* 197, 573-89 (2014).
49. Masters, J. R. et al. Short tandem repeat profiling provides an international reference standard for human cell lines. *Proc Natl Acad Sci USA* 98, 8012-7 (2001).
50. Hideyuki Tanabe, Y. T., Daisuke Minegishi, Miharu Kurematsu, Tohru Masui, Hiroshi Mizusawa. Cell line individualization by STR multiplex system in the cell bank found cross-contamination between ECV304 and EJ-1/T24. *Tiss. Cult. Res. Commun.* 18, 329-338 (1999).
51. Team, R. C. R: A language and environment for statistical computing. 3.5.3 edn (R Foundation for Statistical Computing, Vienna, Austria, 2018).
52. Dobin, A. et al. STAR: ultrafast universal RNA-seq aligner. *Bioinformatics* 29, 15-21 (2013).
53. Li, H. & Durbin, R. Fast and accurate short read alignment with Burrows-Wheeler transform. *Bioinformatics* 25, 1754-60 (2009).

TABLE 1

| \multicolumn{3}{c}{Human SNP} | | |
|---|---|---|
| Locus | Rs# | SEQ ID NO. |
| chr1_10473196 | rs2229687 | 1 |
| chr1_1222267 | rs11260579 | 2 |
| chr1_1249187 | rs12142199 | 3 |
| chr1_151733335 | rs8480 | 4 |
| chr1_169345868 | rs1028180 | 5 |
| chr1_169519112 | rs6020 | 6 |
| chr1_201969082 | rs1130790 | 7 |
| chr1_201973565 | rs3820439 | 8 |
| chr1_202304868 | rs14451 | 9 |
| chr1_20977000 | rs1043424 | 10 |
| chr1_20982631 | rs4704 | 11 |
| chr1_220154768 | rs1061160 | 12 |
| chr1_226352498 | rs2306120 | 13 |
| chr1_230829139 | rs1051038 | 14 |
| chr1_234529570 | rs2175593 | 15 |
| chr1_234614390 | rs117698521 | 16 |
| chr1_46095272 | rs1135812 | 17 |
| chr1_46660295 | rs2292487 | 18 |
| chr1_52264064 | rs1770791 | 19 |
| chr1_54683856 | rs15921 | 20 |
| chr2_10712278 | rs3732114 | 21 |
| chr2_109513601 | rs3827760 | 22 |
| chr2_109543883 | rs922452 | 23 |
| chr2_109552936 | rs3215127 | 24 |
| chr2_109580638 | rs260691 | 25 |
| chr2_207006676 | rs1801318 | 26 |
| chr2_220046975 | rs3731900 | 27 |
| chr2_232326417 | rs1131171 | 28 |
| chr2_238672703 | rs3739038 | 29 |
| chr2_242572846 | rs3208142 | 30 |
| chr2_242618050 | rs1131195 | 31 |
| chr2_27260469 | rs1124649 | 32 |
| chr2_27550967 | rs1049817 | 33 |
| chr2_33226533 | rs4952330 | 34 |
| chr2_3504687 | rs9950 | 35 |
| chr2_68388823 | rs1137930 | 36 |
| chr2_69659126 | rs4453725 | 37 |
| chr2_71365676 | rs357756 | 38 |
| chr2_85769711 | rs1078004 | 39 |
| chr2_99995804 | rs1376443 | 40 |
| chr3_108188993 | rs9868484 | 41 |

TABLE 1-continued

| Human SNP | | |
|---|---|---|
| Locus | Rs# | SEQ ID NO. |
| chr3_121500699 | rs17849995 | 42 |
| chr3_14174427 | rs4685076 | 43 |
| chr3_183560195 | rs13091 | 44 |
| chr3_183861243 | rs843358 | 45 |
| chr3_186509517 | rs187868 | 46 |
| chr3_193374964 | rs9851685 | 47 |
| chr3_33907945 | rs3183987 | 48 |
| chr3_50334231 | rs2269432 | 49 |
| chr3_50355730 | rs35455589 | 50 |
| chr3_50378176 | rs4688725 | 51 |
| chr3_52727257 | rs2289247 | 52 |
| chr3_58154327 | rs8640 | 53 |
| chr4_10099340 | rs13441 | 54 |
| chr4_1330759 | rs1128427 | 55 |
| chr4_164435265 | rs2304802 | 56 |
| chr4_1737502 | rs11248073 | 57 |
| chr4_183815688 | rs4742 | 58 |
| chr4_186097045 | rs6855305 | 59 |
| chr4_25419283 | rs9174 | 60 |
| chr4_39458051 | rs2125313 | 61 |
| chr4_57889677 | rs1056364 | 62 |
| chr4_83795806 | rs10025654 | 63 |
| chr5_137902339 | rs1042665 | 64 |
| chr5_140048209 | rs2251860 | 65 |
| chr5_141014494 | rs2530223 | 66 |
| chr5_176940384 | rs335438 | 67 |
| chr5_179290845 | rs30386 | 68 |
| chr5_311478 | rs2244029 | 69 |
| chr5_31409252 | rs2241337 | 70 |
| chr5_33951693 | rs16891982 | 71 |
| chr5_33964210 | rs183671 | 72 |
| chr5_61694379 | rs247264 | 73 |
| chr5_72798845 | rs14010 | 74 |
| chr5_74069863 | rs6874609 | 75 |
| chr6_105726036 | rs1051484 | 76 |
| chr6_150114745 | rs4816 | 77 |
| chr6_26545632 | rs4871 | 78 |
| chr6_2745352 | rs6927195 | 79 |
| chr6_42992825 | rs3749903 | 80 |
| chr6_49403282 | rs8589 | 81 |
| chr6_70407465 | rs12648 | 82 |
| chr6_89793894 | rs1130809 | 83 |
| chr6_90039670 | rs10502 | 84 |
| chr6_97339078 | rs6684 | 85 |
| chr7_116528240 | rs4808 | 86 |
| chr7_127721507 | rs322825 | 87 |
| chr7_128607384 | rs8043 | 88 |
| chr7_140159721 | rs10243155 | 89 |
| chr7_150916228 | rs6949587 | 90 |
| chr7_158536267 | rs2305473 | 91 |
| chr7_2577781 | rs1043291 | 92 |
| chr7_6063283 | rs4560 | 93 |
| chr7_6066461 | rs2639 | 94 |
| chr7_75959188 | rs2072435 | 95 |
| chr7_897492 | rs10950789 | 96 |
| chr7_99047978 | rs883403 | 97 |
| chr7_99747130 | rs12878 | 98 |
| chr811710888 | rs12338 | 99 |
| chr8_125498547 | rs3812471 | 100 |
| chr8_144662353 | rs1062391 | 101 |
| chr8_144697041 | rs1049832 | 102 |
| chr8_95877787 | rs713113 | 103 |
| chr9_100823084 | rs13049 | 104 |
| chr9_124914613 | rs4679 | 105 |
| chr9_127777161 | rs4574 | 106 |
| chr9_131397479 | rs4837291 | 107 |
| chr9_131767668 | rs2287363 | 108 |
| chr9_135974100 | rs886017 | 109 |
| chr9_139298593 | rs1051957 | 110 |
| chr9_26978259 | rs11555693 | 111 |
| chr9_33026572 | rs20583 | 112 |
| chr9_86278817 | rs7866234 | 113 |
| chr9_96238578 | rs10821135 | 114 |
| chr10_102746503 | rs2863095 | 115 |
| chr10_1046712 | rs2306409 | 116 |
| chr10_120920588 | rs10749291 | 117 |
| chr10_12209752 | rs6686 | 118 |
| chr10_16796919 | rs1049632 | 119 |
| chr10_27434483 | rs2274634 | 120 |
| chr10_72179746 | rs1043098 | 121 |
| chr10_99219885 | rs2152092 | 122 |
| chr11_118967758 | rs643788 | 123 |
| chr11_120107411 | rs882856 | 124 |
| chr11_122928622 | rs4802 | 125 |
| chr11_125479363 | rs2241502 | 126 |
| chr11_3028140 | rs729662 | 127 |
| chr11_4159457 | rs9937 | 128 |
| chr11_47188411 | rs3740691 | 129 |
| chr11_65632262 | rs558114 | 130 |
| chr11_6630833 | rs1043390 | 131 |
| chr11_67200819 | rs4930427 | 132 |
| chr11_82973004 | rs8789 | 133 |
| chr12_104341103 | rs7645 | 134 |
| chr12_109994870 | rs9593 | 135 |
| chr12_112037000 | rs695871 | 136 |
| chr12_118473054 | rs9788041 | 137 |
| chr12_12967127 | rs1051374 | 138 |
| chr12_2968169 | rs3742076 | 139 |
| chr12_2997397 | rs2907608 | 140 |
| chr12_49230035 | rs1057908 | 141 |
| chr12_50529736 | rs3741562 | 142 |
| chr12_6638116 | rs740850 | 143 |
| chr12_6647109 | rs1803621 | 144 |
| chr12_67706466 | rs1060350 | 145 |
| chr13_111298392 | rs436462 | 146 |
| chr13_115004914 | rs2296971 | 147 |
| chr13_25000617 | rs7571 | 148 |
| chr13_28239970 | rs14105 | 149 |
| chr14_102514227 | rs13749 | 150 |
| chr14_105222037 | rs1132975 | 151 |
| chr14_106208082 | rs11621259 | 152 |
| chr14_106208086 | rs1045853 | 153 |
| chr14_106236128 | rs12890621 | 154 |
| chr14_21967916 | rs1139130 | 155 |
| chr14_24615435 | rs4575 | 156 |
| chr14_24736027 | rs14193 | 157 |
| chr14_49294391 | rs34609389 | 158 |
| chr14_51716188 | rs7161242 | 159 |
| chr14_64908845 | rs2236225 | 160 |
| chr14_75359670 | rs2230237 | 161 |
| chr15_40328665 | rs8208 | 162 |
| chr15_44038899 | rs2411284 | 163 |
| chr15_48384907 | rs2250072 | 164 |
| chr15_48426484 | rs1426654 | 165 |
| chr15_48485926 | rs2413887 | 166 |
| chr15_52901433 | rs12915981 | 167 |
| chr15_63937209 | rs2229749 | 168 |
| chr15_63988357 | rs2255243 | 169 |
| chr15_75189930 | rs1130741 | 170 |
| chr15_75650836 | rs1128933 | 171 |
| chr15_75932129 | rs13737 | 172 |
| chr15_77344793 | rs11737 | 173 |
| chr15_89858602 | rs1138465 | 174 |
| chr15_91525197 | rs2301826 | 175 |
| chr16_11773662 | rs3190321 | 176 |
| chr16_15129970 | rs7200543 | 177 |
| chr16_2049640 | rs2286469 | 178 |
| chr16_2285357 | rs26840 | 179 |
| chr16_27238110 | rs1127228 | 180 |
| chr16_70515355 | rs11054 | 181 |
| chr16_70602221 | rs12909 | 182 |
| chr16_718514 | rs7204542 | 183 |
| chr16_75590092 | rs3743601 | 184 |
| chr16_75646576 | rs3743599 | 185 |
| chr16_81010073 | rs1127390 | 186 |
| chr17_19247075 | rs4924987 | 187 |
| chr17_38179492 | rs2302777 | 188 |
| chr17_40722029 | rs665268 | 189 |
| chr17_5294976 | rs14231 | 190 |
| chr17_61908556 | rs13030 | 191 |
| chr17_7217463 | rs2292064 | 192 |
| chr17_73016621 | rs1044228 | 193 |

TABLE 1-continued

| Human SNP | | |
|---|---|---|
| Locus | Rs# | SEQ ID NO. |
| chr17_74056413 | rs2665998 | 194 |
| chr17_80008392 | rs9916764 | 195 |
| chr17_80039481 | rs1140616 | 196 |
| chr18_12351342 | rs11080572 | 197 |
| chr18_33750046 | rs8299 | 198 |
| chr18_77805856 | rs3744872 | 199 |
| chr19_10226256 | rs7710 | 200 |
| chr19_1110829 | rs2302109 | 201 |
| chr19_13885484 | rs10104 | 202 |
| chr19_17628587 | rs6743 | 203 |
| chr19_19023853 | rs3177137 | 204 |
| chr19_1997363 | rs1610045 | 205 |
| chr19_2762585 | rs2302491 | 206 |
| chr19_39196745 | rs3745859 | 207 |
| chr19_39322087 | rs9419 | 208 |
| chr19_39926521 | rs17626 | 209 |
| chr19_4362691 | rs243261 | 210 |
| chr19_4454000 | rs11909 | 211 |
| chr19_45490570 | rs3786505 | 212 |
| chr19_49513273 | rs1062708 | 213 |
| chr19_51301456 | rs4802741 | 214 |
| chr19_580665 | rs4682 | 215 |
| chr19_8468337 | rs2230876 | 216 |
| chr20_25260931 | rs2227890 | 217 |
| chr20_2638579 | rs6753 | 218 |
| chr20_2996497 | rs1178016 | 219 |
| chr20_31427635 | rs2070090 | 220 |
| chr20_3193978 | rs8362 | 221 |
| chr20_391170 | rs7059 | 222 |
| chr20_43530234 | rs4931 | 223 |
| chr20_568696 | rs6053171 | 224 |
| chr21_38568308 | rs6579 | 225 |
| chr21_46271452 | rs235314 | 226 |
| chr22_32795641 | rs5749426 | 227 |
| chr22_32887150 | rs9726 | 228 |
| chr22_38273749 | rs9466 | 229 |
| chr22_39134715 | rs1062687 | 230 |
| chr22_42276742 | rs2228314 | 231 |
| chr22_42912106 | rs1812240 | 232 |
| chr22_42970032 | rs137055 | 233 |
| chr22_43195147 | rs1128013 | 234 |
| chr22_43610207 | rs138993 | 235 |
| chr22_50885775 | rs1053744 | 236 |
| chrX_75004529 | rs1343879 | 237 |

TABLE 2

| Mouse SNP | | | |
|---|---|---|---|
| Locus | Gene | SEQ ID NO. | Cell line |
| chr1_91387260 | Ilkap | 238 | 4T1 |
| chr5_136026554 | Dtx2 | 239 | 4T1 |
| chr11_100695233 | Dhx58 | 240 | 4T1 |
| chr11_69740416 | Polr2a | 241 | 4T1 |
| chr12_110649884 | Dync1h1 | 242 | 4T1 |
| chr19_47898131 | Itprip | 243 | 4T1 |
| chr2_29843149 | Urm1 | 244 | A20 |
| chr2_122052069 | Eif3j1 | 245 | A20 |
| chr10_117355993 | Cpsf6 | 246 | A20 |
| chr10_127064881 | Cdk4 | 247 | A20 |
| chr11_101288969 | Becn1 | 248 | A20 |
| chr11_69589186 | Trp53 | 249 | A20 & MC38 |
| chr11_69589202 | Trp53 | 250 | A20 & MC38 |
| chr5_90215024 | Cox18 | 251 | B16BL6 |
| chr13_37985317 | Ssr1 | 252 | B16BL6 |
| chr14_117186703 | Gpc6 | 253 | B16BL6 |
| chr14_55745832 | Nop9 | 254 | B16BL6 |
| chr15_80929461 | Tnrc6b | 255 | B16BL6 |
| chr18_60692027 | Ndst1 | 256 | B16BL6 |
| chr3_100144344 | Wdr3 | 257 | B16BL6; B16F0; B16F1; B16F10 |
| chr4_109883738 | Faf1 | 258 | B16BL6; B16F0; B16F1; B16F10 |
| chr5_108087329 | Mtf2 | 259 | B16BL6; B16F0; B16F1; B16F10 |
| chr15_97790681 | Slc48a1 | 260 | B16BL6; B16F0; B16F1; B16F10 |
| chr16_57166188 | Nit2 | 261 | B16BL6; B16F0; B16F1; B16F10 |
| chr19_32799998 | Pten | 262 | B16BL6; B16F0; B16F1; B16F10 |
| chr19_5716287 | Ehbp1l1 | 263 | B16BL6; B16F0; B16F1; B16F10 |
| chr2_10091850 | Kin | 264 | B16F0 |
| chr2_5053146 | Optn | 265 | B16F0 |
| chr3_122275655 | Dnttip2 | 266 | B16F0 |
| chr4_129639489 | Txlna | 267 | B16F0 |
| chr7_131362539 | 2310057M21Rik | 268 | B16F0 |
| chr9_109100255 | Plxnb1 | 269 | B16F0 |
| chr5_115985533 | Cit | 270 | B16F10 |
| chr8_119599093 | Taf1c | 271 | B16F10 |
| chr9_86564707 | Pgm3 | 272 | B16F10 |
| chr13_21445463 | Zscan26 | 273 | B16F10 |
| chr18_12197207 | Npc1 | 274 | B16F10 |
| chrX_169313612 | Hccs | 275 | B16F10 |
| chr3_69030400 | Smc4 | 276 | C1498 |
| chr4_116074925 | Uqcrh | 277 | C1498 |
| chr11_101411430 | Aarsd1 | 278 | C1498 |
| chr11_69588367 | Trp53 | 279 | C1498; JC |
| chr11_69588367 | Trp53 | 280 | C1498; JC |
| chr17_84712802 | Lrpprc | 281 | C1498 |

TABLE 2-continued

Mouse SNP

| Locus | Gene | SEQ ID NO. | Cell line |
|---|---|---|---|
| chr18_24638470 | Elp2 | 282 | C1498 |
| chr8_83571885 | Tecr | 283 | Colon26 |
| chr12_84609021 | Abcd4 | 284 | Colon26 |
| chr13_4135258 | Akr1c18 | 285 | Colon26 |
| chr13_93880550 | Arsb | 286 | Colon26 |
| chr18_80197758 | Rbfa | 287 | Colon26 |
| chrX_41825559 | Thoc2 | 288 | Colon26 |
| chr3_95659269 | Mcl1 | 289 | CT26WT |
| chr6_124749315 | Atn1 | 290 | CT26WT |
| chr14_56693508 | Mphosph8 | 291 | CT26WT |
| chr17_35881376 | Dhx16 | 292 | CT26WT |
| chr18_60550220 | Dctn4 | 293 | CT26WT |
| chrX_164071728 | Siah1b | 294 | CT26WT |
| chr13_74667993 | Erap1 | 295 | CT26WT Colon26 |
| chr14_101695962 | Uchl3 | 296 | CT26WT Colon26 |
| chr14_34343682 | Glud1 | 297 | CT26WT Colon26 |
| chr15_12924098 | Drosha | 298 | CT26WT Colon26 |
| chr15_99404465 | Tmbim6 | 299 | CT26WT Colon26 |
| chrX_157454879 | Sms | 300 | CT26WT Colon26 |
| chr2_105013312 | Eif3m | 301 | EG7Ova |
| chr3_32728469 | Mrpl47 | 302 | EG7Ova |
| chr7_19514493 | Trappc6a | 303 | EG7Ova |
| chr7_48803057 | Zdhhc13 | 304 | EG7Ova |
| chr15_103243005 | Hnrnpa1 | 305 | EG7Ova |
| chrX_73788891 | Ssr4 | 306 | EG7Ova |
| chr3_97168031 | Acp6 | 307 | EL4 |
| chr3_14557226 | Lrrcc1 | 308 | EL4 |
| chr4_98934494 | Usp1 | 309 | EL4 |
| chr8_122890806 | Ankrd11 | 310 | EL4 |
| chr14_14114149 | Psmd6 | 311 | EL4 |
| chr17_56424099 | Ptprs | 312 | EL4 |
| chr5_33643749 | Slbp | 313 | EMT6 |
| chr9_3430504 | Cwfl912 | 314 | EMT6 |
| chr10_50849489 | Ascc3 | 315 | EMT6 |
| chr11_70014640 | Acadvl | 316 | EMT6 |
| chr19_8770295 | Nxf1 | 317 | EMT6 |
| chrX_13158898 | Usp9x | 318 | EMT6 |
| chr5_149623543 | Hsph1 | 319 | H22 |
| chr6_131370348 | Ybx3 | 320 | H22 |
| chr7_135698360 | Mki67 | 321 | H22 |
| chr9_109842576 | Nme6 | 322 | H22 |
| chr9_21757780 | Spc24 | 323 | H22 |
| chr12_24711691 | Rrm2 | 324 | H22 |
| chr3_145578132 | Znhit6 | 325 | Hepa16 |
| chr9_72617951 | Rfx7 | 326 | Hepa16 |
| chr13_3573709 | BC016423 | 327 | Hepa16 |
| chr15_31594403 | Cct5 | 328 | Hepa16 |
| chr17_23676012 | Tnfrsf12a | 329 | Hepa16 |
| chr19_15956304 | Cep78 | 330 | Hepa16 |
| chr4_55378242 | Rad23b | 331 | J558 |
| chr7_126371216 | Spns1 | 332 | J558 |
| chr9_111230959 | Mlh1 | 333 | J558 |
| chr11_50210648 | Sqstm1 | 334 | J558 |
| chr11_69588647 | Trp53 | 335 | J558 & Renca |
| chr11_69588703 | Trp53 | 336 | J558 & Renca |
| chrX_101293807 | Med12 | 337 | J558 |
| chr5_3559131 | Fam133b | 338 | J774A1 |
| chr8_72255808 | Ap1m1 | 339 | J774A1 |
| chr10_26872682 | Arhgap18 | 340 | J774A1 |
| chr13_114826176 | Mocs2 | 341 | J774A1 |
| chr17_35835434 | Tubb5 | 342 | J774A1 |
| chr19_37387069 | Kif11 | 343 | J774A1 |
| chr8_72739404 | Sin3b | 344 | JC |
| chr9_119918477 | Wdr48 | 345 | JC |
| chr12_17277245 | Pdia6 | 346 | JC |
| chr18_12189845 | 3110002H16Rik | 347 | JC |
| chr19_8831307 | Hnrnpul2 | 348 | JC |
| chr2_25372768 | Sapcd2 | 349 | KLN205 |
| chr3_145596142 | Znhit6 | 350 | KLN205 |
| chr5_145132963 | Pdap1 | 351 | KLN205 |
| chr8_122571980 | Cdt1 | 352 | KLN205 |
| chr17_84706019 | Lrpprc | 353 | KLN205 |
| chrX_140472073 | Prps1 | 354 | KLN205 |
| chr5_38234081 | Lyar | 355 | L1210 |
| chr5_69566389 | Guf1 | 356 | L1210 |
| chr6_135023351 | Ddx47 | 357 | L1210 |

TABLE 2-continued

Mouse SNP

| Locus | Gene | SEQ ID NO. | Cell line |
|---|---|---|---|
| chr10_40850958 | Cdc40 | 358 | L1210 |
| chr12_54768043 | Snx6 | 359 | L1210 |
| chrX_94078824 | Zfx | 360 | L1210 |
| chr1_55080340 | Hspd1 | 361 | L5178R |
| chr3_96579869 | Polr3gl | 362 | L5178R |
| chr9_57256682 | 1700017B05Rik | 363 | L5178R |
| chr10_116498369 | Cnot2 | 364 | L5178R |
| chr11_109436637 | Amz2 | 365 | L5178R |
| chrX_105874791 | Atrx | 366 | L5178R |
| chr4_127047898 | Zmym1 | 367 | LLC |
| chr4_129008072 | Ak2 | 368 | LLC |
| chr4_155855159 | Dvl1 | 369 | LLC |
| chr5_145244535 | Zfp655 | 370 | LLC |
| chr6_145246772 | Kras | 371 | LLC |
| chr14_86866528 | Diap3 | 372 | LLC |
| chr1_161074777 | Cenpl | 373 | MBT2 |
| chr2_112406248 | Katnbl1 | 374 | MBT2 |
| chr2_69194469 | Spc25 | 375 | MBT2 |
| chr7_19006050 | Irf2bp1 | 376 | MBT2 |
| chr13_104144156 | Trappe13 | 377 | MBT2 |
| chr16_48999045 | C330027C09Rik | 378 | MBT2 |
| chr7_41625342 | 2610021A01Rik | 379 | MC38 |
| chr8_70180548 | Tmem161a | 380 | MC38 |
| chr9_22013055 | Prkcsh | 381 | MC38 |
| chr13_74646321 | Erap1 | 382 | MC38 |
| chr15_34485603 | Hrsp12 | 383 | MC38 |
| chr5_145144973 | Bud31 | 384 | MPC11 |
| chr6_145232109 | Kras | 385 | MPC11 |
| chr13_3575438 | BC016423 | 386 | MPC11 |
| chr15_61989534 | Myc | 387 | MPC11 |
| chr17_35016227 | Vars | 388 | MPC11 |
| chr19_46076132 | Nolc1 | 389 | MPC11 |
| chr2_170515838 | Pfdn4 | 390 | Neuro2a |
| chr7_123428178 | Lcmt1 | 391 | Neuro2a |
| chr11_96911133 | Cdk5rap3 | 392 | Neuro2a |
| chr13_97191232 | Hexb | 393 | Neuro2a |
| chr15_31598022 | Cct5 | 394 | Neuro2a |
| chr16_20680966 | Eif4g1 | 395 | Neuro2a |
| chr8_122482698 | Piezo1 | 396 | P388D1 |
| chr8_70296436 | Ddx49 | 397 | P388D1 |
| chr9_24424805 | Dpy19l1 | 398 | P388D1 |
| chr11_98694175 | Psmd3 | 399 | P388D1 |
| chr12_73982520 | Snapc1 | 400 | P388D1 |
| chr13_69811634 | Med10 | 401 | P388D1 |
| chr1_43983175 | Tpp2 | 402 | P815 |
| chr7_105636932 | Arfip2 | 403 | P815 |
| chr9_36759241 | Stt3a | 404 | P815 |
| chr11_94634572 | Lrrc59 | 405 | P815 |
| chr12_108812956 | Yy1 | 406 | P815 |
| chr13_104811305 | Cwc27 | 407 | P815 |
| chr1_63152796 | Ndufs1 | 408 | Pan02 |
| chr7_127972166 | Fus | 409 | Pan02 |
| chr7_45156316 | Pih1d1 | 410 | Pan02 |
| chr16_16983639 | Mapk1 | 411 | Pan02 |
| chr17_75538733 | Fam98a | 412 | Pan02 |
| chr19_6920138 | Esrra | 413 | Pan02 |
| chr4_147941100 | 2510039O18Rik | 414 | Renca |
| chr12_69579944 | Mettl21d | 415 | Renca |
| chr13_19376528 | Stard3nl | 416 | Renca |
| chr17_71517626 | Ndc80 | 417 | Renca |
| chrX_93420657 | Pola1 | 418 | Renca |
| chr1_24711551 | Lmbrd1 | 419 | RM1 |
| chr4_140702160 | Rcc2 | 420 | RM1 |
| chr11_120720063 | Lrrc45 | 421 | RM1 |
| chr11_69589607 | Trp53 | 422 | RM1 |
| chr15_12890119 | Drosha | 423 | RM1 |
| chr17_46648312 | Mrpl2 | 424 | RM1 |
| chr3_142810708 | Pkn2 | 425 | S91-P1-150414 |
| chr3_94864330 | Pogz | 426 | S91-P1-150414 |
| chr4_131865081 | Mecr | 427 | S91-P1-150414 |
| chr9_15308558 | Taf1d | 428 | S91-P1-150414 |
| chr17_33925530 | Tapbp | 429 | S91-P1-150414 |
| chr17_35668634 | Gtf2h4 | 430 | S91-P1-150414 |
| chr5_29441373 | Nom1 | 431 | WEHI164 |
| chr13_106947227 | Dimt1 | 432 | WEHI164 |
| chr16_56029611 | Pcnp | 433 | WEHI164 |

TABLE 2-continued

Mouse SNP

| Locus | Gene | SEQ ID NO. | Cell line |
|---|---|---|---|
| chr17_45419631 | Cdc51 | 434 | WEHI164 |
| chr18_35572424 | Matr3 | 435 | WEHI164 |
| chr19_23676211 | Gm6563 | 436 | WEHI164 |

TABLE 3

Human Y Chromosome SNP

| Locus | Rs# |
|---|---|
| chrY_14832620 | rs7067496 |
| chrY_15467824 | rs2032654 |
| chrY_15591537 | rs2032653 |

TABLE 4

| chromosome | position |
|---|---|
| chr11 | 78371203 |
| chr16 | 15839180 |

TABLE 5

| virus | genome | Sequence |
|---|---|---|
| EBV | NC_009334 | 86-249 |
| EBV | NC_009334 | 549-765 |
| EBV | NC_009334 | 1037-1189 |
| EBV | NC_009334 | 2571-2732 |
| HBV | NC_003977 | 304-489 |
| HBV | NC_003977 | 1393-1618 |
| HPV16 | NC_001526 | 7152-7271 |
| HPV16 | NC_001526 | 7402-7901 |
| HPV16 | NC_001526 | 86-406 |
| HPV18 | NC_001357 | 30-1774 |
| HIV | NC_001802 | 20-177 |
| HIV | NC_001802 | 8443-8949 |
| mycoplasma | CP029295.1 | 505718-506180 |

TABLE 6

Mouse Genome Sequence Homologous to Human

| Locus | SEQ ID NO. |
|---|---|
| chr1:105664142-105664584 | 437 |
| chr1:131599847-131600265 | 438 |
| chr1:133620651-133621057 | 439 |
| chr1:38175197-38175663 | 440 |
| chr1:42255546-42255968 | 441 |
| chr1:43553833-43554279 | 442 |
| chr1:55148075-55148405 | 443 |
| chr1;55914041-55914488 | 444 |
| chr1:55987400-55987857 | 445 |
| chr2:114047027-114047475 | 446 |
| chr2:114049076-114049523 | 447 |
| chr2:114734704-114735308 | 448 |
| chr2:114938795-114939209 | 449 |
| chr2:116075697-116076099 | 450 |
| chr2:119326991-119327420 | 451 |
| chr2:119411547-119411942 | 452 |
| chr2:140659041-140659312 | 453 |
| chr2:144089441-144089832 | 454 |
| chr3:34504194-34504633 | 455 |
| chr3:36986772-36987094 | 456 |
| chr3:37025884-37026323 | 457 |

TABLE 6-continued

Mouse Genome Sequence Homologous to Human

| Locus | SEQ ID NO. |
|---|---|
| chr3:6002716-6003025 | 458 |
| chr4:100853347-100853768 | 459 |
| chr4:102760274-102760632 | 460 |
| chr4:41519808-41520239 | 461 |
| chr4:43443358-43443775 | 462 |
| chr4:43445287-43445715 | 463 |
| chr4:76039612-76039883 | 464 |
| chr5:106322349-106322777 | 465 |
| chr5:122861456-122861856 | 466 |
| chr5:122988599-122989028 | 467 |
| chr6:108664368-108664777 | 468 |
| chr7:102097926-102098361 | 469 |
| chr7:102428566-102429007 | 470 |
| chr7:102698517-102698966 | 471 |
| chr7:105384072-105384436 | 472 |
| chr7:105635729-105636145 | 473 |
| chr7:105740673-105740944 | 474 |
| chr7:107665615-107666028 | 475 |
| chr7:108754667-108755104 | 476 |
| chr8:103447835-103448254 | 477 |
| chr8:115428668-115429087 | 478 |
| chr8:123892100-123892548 | 479 |
| chr9:119495272-119495684 | 480 |
| chr9:120929616-120930041 | 481 |
| chr9:124124306-124124697 | 482 |
| chr9:24974244-24974660 | 483 |
| chr9:82866266-82866706 | 484 |
| chr9:84973186-84973624 | 485 |
| chr10:29698549-29699004 | 486 |
| chr10:75061569-75061989 | 487 |
| chr11:101189377-101189820 | 488 |
| chr11:101277344-101277788 | 489 |
| chr11:101867409-101867715 | 490 |
| chr11:102509968-102510377 | 491 |
| chr11:114183205-114183653 | 492 |
| chr11:115849863-115850303 | 493 |
| chr12:101040300-101040687 | 494 |
| chr12:107638060-107638501 | 495 |
| chr12:66469994-66470265 | 496 |
| chr13:31911885-31912294 | 497 |
| chr13:38196485-38196783 | 498 |
| chr13:39523526-39523952 | 499 |
| chr13:43200327-43200776 | 500 |
| chr13:43200696-43201123 | 501 |
| chr13:44317005-44317340 | 502 |
| chr13:44375738-44376192 | 503 |
| chr14:100461399-100461810 | 504 |
| chr14:100950247-100950697 | 505 |
| chr14:100978309-100978722 | 506 |
| chr14:103095102-103095512 | 507 |
| chr14:105815614-105816038 | 508 |
| chr14:111681168-111681625 | 509 |
| chr14:114547663-114548108 | 510 |
| chr14:123186854-123187271 | 511 |
| chr14:52463385-52463656 | 512 |
| chr15:102430819-102431236 | 513 |
| chr15:102811273-102811660 | 514 |
| chr15:102966510-102966781 | 515 |
| chr15:103298047-103298653 | 516 |
| chr15:103524801-103525249 | 517 |
| chr15:34141703-34142120 | 518 |
| chr16:29666774-29667232 | 519 |
| chr16:29875939-29876394 | 520 |

TABLE 6-continued

| Mouse Genome Sequence Homologous to Human | |
|---|---|
| Locus | SEQ ID NO. |
| chr16:6057738-6058045 | 521 |
| chr16:6776352-6776786 | 522 |
| chr16:76321297-76321735 | 523 |
| chr16:78941222-78941652 | 524 |
| chr16:80265994-80266442 | 525 |
| chr16:80434685-80435068 | 526 |
| chr16:87128020-87128361 | 527 |
| chr16:87319732-87320189 | 528 |
| chr16:91114059-91114450 | 529 |
| chr17:15370365-15370824 | 530 |
| chr17:26742420-26742783 | 531 |
| chr17:26935067-26935511 | 532 |
| chr17:27876446-27876890 | 533 |
| chr17:30292965-30293355 | 534 |
| chr18:19963182-19963628 | 535 |
| chr18:25632724-25633184 | 536 |
| chr18:34606137-34606581 | 537 |
| chr18:34641045-34641374 | 538 |
| chr18:34759289-34759725 | 539 |
| chr18:34863942-34864380 | 540 |
| chr19:41962522-41962964 | 541 |
| chr19:46061929-46062390 | 542 |
| chr19:46251931-46252398 | 543 |
| chr19:46306521-46306978 | 544 |

TABLE 7

Authentication and contaminant detection of cell line pairs with serial dilutions*

| Cell line mixture | Major Component | Minor Component (Contaminant) | Minor component ratio (percentage)** | #Informative SNPs | Heterogeneity ratio (percentage) | Major component inferred*** | Minor component (contaminant) inferred**** | Contaminant ratio (percentage)*** | P-value***** |
|---|---|---|---|---|---|---|---|---|---|
| PANC1:RT4 | PANC1 | — | — | 118 | 1.4 | PANC1 (99.46%) | — | — | — |
| | RT4 | — | — | 122 | 1.65 | RT4 (98.54%) | — | — | — |
| | RT4 | PANC1 | 5 | 86 | 3.3 | RT4 (97.78%) | PANC1 (96.73%) | 2.88 | 2.98E-16 |
| | RT4 | PANC1 | 2.5 | 80 | 1.85 | RT4 (97.93%) | PANC1 (94.79%) | 1.08 | 6.65E-12 |
| | RT4 | PANC1 | 1.25 | 81 | 1.1 | RT4 (97.76%) | PANC1 (88.14%) | 0.41 | 3.97E-09 |
| | RT4 | PANC1 | 0.625 | 80 | 1.06 | RT4 (97.76%) | — | — | — |
| | PANC1 | RT4 | 5 | 131 | 8.09 | PANC1 (99.50%) | RT4 (98.33%) | 7.21 | 5.01E-17 |
| | PANC1 | RT4 | 2.5 | 128 | 4.06 | PANC1 (99.35%) | RT4 (95.50%) | 2.81 | 5.01E-17 |
| | PANC1 | RT4 | 1.25 | 132 | 2.75 | PANC1 (99.49%) | RT4 (90.73%) | 1.48 | 5.01E-17 |
| | PANC1 | RT4 | 0.625 | 139 | 2.62 | PANC1 (99.47%) | RT4 (81.61%) | 1.08 | 1.67E-08 |
| LNCAPCLONEFGC: MV411 | LNCAPCLONEFGC | — | — | 97 | 1.005 | LNCAPCLONEFGC (99.03%) | — | — | — |
| | MV411 | — | — | 93 | 0.965 | MV411 (99.03%) | — | — | — |
| | MV411 | LNCAPCLONEFGC | 5 | 99 | 9 | MV411 (99.45%) | LNCAPCLONEFGC (96.83%) | 9.08 | 5.01E-17 |
| | MV411 | LNCAPCLONEFGC | 2.5 | 111 | 4.51 | MV411 (99.50%) | LNCAPCLONEFGC (98.34%) | 4.14 | 5.01E-17 |
| | MV411 | LNCAPCLONEFGC | 1.25 | 117 | 2.18 | MV411 (99.18%) | LNCAPCLONEFGC (90.32%) | 2.01 | 1.67E-09 |
| | MV411 | LNCAPCLONEFGC | 0.625 | 112 | 1.58 | MV411 (99.00%) | LNCAPCLONEFGC (89.44%) | 0.0148 | 1.67E-09 |
| | LNCAPCLONEFGC | MV411 | 5 | 102 | 2.35 | LNCAPCLONEFGC (98.99%) | MV411 (94.57%) | 2.14 | 5.01E-17 |
| | LNCAPCLONEFGC | MV411 | 2.5 | 101 | 1.67 | LNCAPCLONEFGC (99.04%) | MV411 (91.58%) | 0.88 | 2.37E-11 |
| | LNCAPCLONEFGC | MV411 | 1.25 | 98 | 1.49 | LNCAPCLONEFGC (99.03%) | MV4U (87.77%) | 0.71 | 2.76E-11 |
| | LNCAPCLONEFGC | MV411 | 0.625 | 105 | 1.36 | LNCAPCLONEFGC (99.03%) | — | — | — |
| CAL28:RAJI | CAL27 | — | — | 39 | 1.39 | CAL27 (97.39%) | — | — | — |
| | RAJI | — | — | 114 | 1.18 | RAJI (98.56%) | — | — | — |
| | RAJI | CAL27 | 5 | 116 | 5.36 | RAJI (98.66%) | CAL27 (99.12%) | 5.54 | 5.01E-17 |
| | RAJI | CAL27 | 2.5 | 127 | 4.17 | RAJI (98.32%) | CAL27 (94.70%) | 4.01 | 8.37E-11 |
| | RAJI | CAL27 | 1.25 | 121 | 1.84 | RAJI (98.51%) | CAL27 (90.83%) | 2.21 | 8.37E-06 |
| | RAJI | CAL27 | 0.625 | 116 | 2.49 | RAJI (98.50%) | CAL27 (90.43%) | 2.28 | 1.67E-07 |
| | CAL27 | RAJI | 5 | 121 | 7.11 | CAL27 (99.17%) | RAJI (99.51%) | 5.41 | 5.01E-17 |
| | CAL27 | RAJI | 2.5 | 113 | 3.79 | CAL27 (98.94%) | RAJI (92.06%) | 2.41 | 4.30E-13 |
| | CAL27 | RAJI | 1.25 | 112 | 2.14 | CAL27 (98.61%) | RAJI (83.42%) | 1.21 | 4.20E-07 |
| | CAL27 | RAJI | 0.625 | 112 | 1.4 | CAL27 (98.49%) | RAJI (83.75%) | 0.61 | 1.59E-07 |

*average values for each cell line mixture with 3 technical replicates except the unmixed ones
**percentage of the minor cell line based on cell counts
***genotype similarity shown in parenthesis
****chimeric genotype similarity shown in parenthesis
*****probability that the inferred minor component is incorrect

TABLE 8

Authentication and contaminant detection of cell line mixtures

| Cell line mixture | #Informative SNPs | Heterogeneity ratio (percentage) | Major component inferred*** | Minor component (contaminant) inferred**** | Contaminant ratio (percentage)*** | P-value***** |
|---|---|---|---|---|---|---|
| ME180:143B | 119 | 6.54 | ME180 (98.06%) | 143B (97.09%) | 7.01 | 5.01E-17 |
| 143B:ME180 | 135 | 3.24 | 143B (98.55%) | ME180 (94.17%) | 3.21 | 5.01E-17 |
| JEG3:A875 | 104 | 1.63 | JEG3 (98.49%) | A875 (87.94%) | 1.21 | 5.01E-13 |
| A875:JEG3 | 93 | 15.50 | A875 (91.71%) | JEG3 (99.00%) | 16.71 | 5.01E-17 |
| HT3:C33A | 115 | 3.54 | HT3 (100%) | C33A (97.06%) | 3.41 | 5.01E-17 |
| C33A:HT3 | 90 | 4.34 | C33A (99.01%) | HT3 (100%) | 4.61 | 0 |
| DOTC24510:CASKI | 136 | 5.47 | DOTC24510 (98.99%) | CASKI (93.97%) | 5.21 | 5.01E-17 |
| CASKI:DOTC24510 | 129 | 4.26 | CASKI (98.98%) | DOTC24510 (91.84%) | 4.11 | 5.01E-17 |
| HLE:HCC94 | 163 | 2.62 | HLE (99.0%), HLF (96.08%) | HCC94 (91.46%) | 2.91 | 5.01E-17 |
| HCC94:HLE | 133 | 10.65 | HCC94 (97.6%) | HLE (96.63%), HLF (96.63%) | 10.11 | 5.01E-17 |
| NCIH1993:LS174T | 141 | 3.97 | NCIH1993 (98.05%) | LS174T (95.12%), LS180 (95.12%), HM7 (94.63%) | 4.21 | 5.01E-17 |
| LS174T:NCIH1993 | 114 | 4.88 | LS174T (99.02%), LS180 (99.03%), HM7 (98.54%) | NCIH1993 (97.06%) | 4.71 | 5.01E-17 |
| OSC19:SF763 | 152 | 7.03 | OSC19 (98.08%) | SF763 (96.15%) | 5.71 | 5.01E-17 |
| SF763:OSC19 | 133 | 3.35 | SF763 (99.02%) | OSC19 (90.15%) | 2.91 | 2.51E-16 |
| SW626:SJCRH30 | 155 | 11.67 | SW626 (95.63%) | SJCRH30 (98.54%) | 13.21 | 5.01E-17 |
| SJCRH30:SW626 | 88 | 1.79 | SJCRH30 (98.55%) | SW626 (94.2%) | 2.01 | 1.58E-16 |
| A875:ME180 | 115 | 2.68 | A875 (98.56%) | ME180 (95.67%) | 2.31 | 5.01E-17 |
| DOTC24510:CASKI | 144 | 1.75 | DOTC24510 (98.5%) | CASKI (86%) | 1.71 | 1.00E-15 |
| OSC19:SF763 | 130 | 2.68 | OSC19 (98.56%) | SF763 (93.27%) | 2.11 | 5.01E-17 |
| NOZ:SW626 | 127 | 0.82 | NOZ (97.56%) | SW626 (82.93%) | 0.71 | 3.98E-11 |
| SNU739:MM1R | 121 | 2.29 | SNU739 (99.01%) | MM1R (94.03%), MM1S (94.03%) | 1.71 | 5.01E-17 |
| U251:SR | 127 | 1.09 | U251 (98.54%) | SR (89.76%) | 2.11 | 5.01E-17 |

*in the format of major cell line: minor/contaminating cell line
**genotype similarity shown in parenthesis
***chimeric genotype similarity shown in parenthesis
****probability that the inferred minor component is wrong

TABLE 9

Authentication of cell lines

| Cell line | # of informative SNPs | Heterogeneity ratio (percentage) | Cell line inferred* |
|---|---|---|---|
| G292CloneA14B1 | 176 | 7.62 | G292CLONEA141B1 (98.53%) |
| HPAF-II | 153 | 6.63 | HPAFII(99.01%) |
| PL45 | 135 | 4.49 | PL45(98.42%), PANC1005(98.43%) |
| HCC827 | 193 | 3.46 | HCC827(99.51%) |
| Hela | 138 | 2.99 | HELA(99.52%), HELA229(99.06%) |
| OCI-AML-2 | 143 | 2.77 | OCIAML2(98.1%) |
| K-562 | 158 | 2.56 | K562(98.52%) |
| OVCAR-5 | 154 | 2.14 | OVCAR5(97.52%) |
| A-427 | 115 | 2.05 | A427(97.45%) |
| 8505C | 158 | 1.96 | 8505C(98.05%) |
| NOZ | 143 | 1.87 | NOZ(97.94%) |
| Hep3B | 106 | 1.77 | HEP3B217(95.73%) |
| SF268 | 113 | 1.63 | SF268(93.85%) |
| NCI-H1993 | 101 | 1.57 | NCIH1993(96.25%) |
| NCI-H1793 | 139 | 1.56 | NCIH1793(98.55%) |
| NCI-H1688 | 120 | 1.55 | NCIH1688(99.48%) |
| MX-1 | 141 | 1.51 | MX 1(100%) |
| NCI-N87 | 120 | 1.45 | NCIN87(98.03%) |
| RBE | 110 | 1.43 | RBE(98.94%) |
| SiHa-579 | 121 | 1.43 | SIHA(98.84%) |
| KPL-4 | 118 | 1.42 | KPL4(96.43%) |
| EVSA-T | 132 | 1.41 | EVSAT(97.86%) |
| Ishikawa | 90 | 1.29 | ISHIKAWA(100%), ISHIKAWAHERAKLIO02ER(100%) |
| IM95m | 100 | 1.28 | IM95M(98.35%), IM95(98.34%) |
| MES-SA | 99 | 1.26 | MESSA(99.5%) |
| MHH-CALL-2 | 189 | 1.26 | MHHCALL2(100%) |

TABLE 9-continued

Authentication of cell lines

| Cell line | # of informative SNPs | Heterogeneity ratio (percentage) | Cell line inferred* |
|---|---|---|---|
| OZ | 107 | 1.26 | OZ(98.95%) |
| SH-SY5Y | 86 | 1.25 | SHSY5Y(99.47%), SKNSH(99.47%) |
| PC-9 | 116 | 1.24 | PC9(98.48%), PC14(97.99%) |
| Calu-3 | 117 | 1.23 | CALU3(98.02%) |
| ME-180 | 89 | 1.21 | ME180(98.89%) |
| SUM159PT | 89 | 1.20 | SUM159PT(98.94%) |
| NCI-H322 | 107 | 1.18 | NCIH322(99.46%) |
| LS174T | 85 | 1.18 | LS174T(99.44%), HM7(98.89%), LS180(99.45%) |
| NCI-H292 | 95 | 1.18 | NCIH292(100%) |
| NCI-H1568 | 153 | 1.16 | NCIH1568(97.57%) |
| GTL-16 | 113 | 1.15 | GTL16(98.46%), MKN45(97.97%) |
| KG-1a | 104 | 1.15 | KG1A(97.34%), KG1(97.93%) |
| HM-7 | 104 | 1.15 | HM7(98.38%), LS180(98.92%), LS174T(98.92%) |
| HCCLM3 | 119 | 1.14 | HCCLM3(98.92%) |
| MHCC97-H | 75 | 1.08 | MHCC97H(99.34%) |
| NCI-H1373 | 137 | 1.08 | NCIH1373(98.16%) |
| Capan-2 | 139 | 1.06 | CAPAN2(99.52%) |
| ML-2 | 111 | 1.06 | ML2(99.49%) |
| SW1463 | 144 | 1.06 | SW1463(93.06%) |
| NCI-H1395 | 110 | 1.06 | NCIH1395(98.93%) |
| A-673 | 112 | 1.05 | A673(98.54%) |
| DU-145 | 149 | 1.04 | DU145(99.52%) |
| NCI-H1781 | 154 | 1.04 | NCIH1781(99.51%) |
| SK-NEP-1 | 79 | 1.04 | SKNEP1(99.49%) |
| A-431 | 75 | 1.04 | A431(98.5%) |
| HepG2C3A | 84 | 1.02 | HEPG2C3A(99.32%) |
| U251 | 102 | 1.01 | U251MG(99.45%) |
| SNU-354 | 88 | 1.01 | SNU354(94.42%) |
| Hs445 | 93 | 1.00 | HS445(99.49%) |
| JEG-3 | 94 | 1.00 | JEG3(99.39%) |
| Z-138 | 94 | 1.00 | Z138(98.54%) |
| IHH-4 | 87 | 1.00 | IHH4(100%) |
| SF763 | 84 | 1.00 | SF763(98.44%) |
| SNU-739-P1 | 95 | 1.00 | SNU739(98.95%) |
| HeLa299 | 78 | 0.99 | HELA(99.43%), HELA229(99.43%) |
| L-82 | 106 | 0.99 | L82(97.96%) |
| MM1R | 105 | 0.98 | MM1R(100%), MM1S(99.48%) |
| HT-3 | 118 | 0.97 | HT3(99.48%) |
| SCH | 92 | 0.97 | SCH(99.41%) |
| U118MG | 128 | 0.97 | U118MG(96.17%) |
| OSC-19 | 118 | 0.96 | OSC19(98.41%) |
| JVM-13 | 89 | 0.94 | JVM13(98.97%) |
| WiDr | 113 | 0.94 | HT29(97.14%) |
| SK-N-SH | 78 | 0.93 | SKNSH(99.5%), SHSY5Y(99.50%) |
| KYSE-410 | 147 | 0.92 | KYSE410(97.55%) |
| HBL-1 | 100 | 0.92 | HBL1(100%) |
| NAMALWACSN | 104 | 0.91 | NAMALWACSN(98.98%), NAMALWA(98.46%) |
| SNU-368 | 23 | 0.91 | SNU368(95.89%) |
| Jurkat | 101 | 0.90 | JURKAT(98.34%), JURKATCLONEE61(98.37%) |
| SK-N-AS | 124 | 0.89 | SKNAS(99.04%) |
| SNU-2535 | 85 | 0.88 | SNU2535(99.47%) |
| HCCC-9810 | 94 | 0.86 | HCCC9810(98.31%) |
| COLO320DM | 96 | 0.85 | COLO320DM(98.47%) |
| MS751 | 103 | 0.85 | MS751(97.88%) |
| SW48 | 34 | 0.85 | SW48(98.2%) |
| CCRF-CEM | 72 | 0.84 | COC1DDP(99.02%), CCRFCEM(99.02%), COC1(99.02%) |
| YCC-2 | 121 | 0.84 | YCC2(97.98%) |
| TJ905 | 100 | 0.84 | TJ905(97.53%) |
| CoC1DDP | 92 | 0.83 | COC1DDP(99.46%), CCRFCEM(99.46%), COC1(99.46%) |
| SK-UT-1 | 94 | 0.83 | SKUT1(99.03%) |
| D283 | 77 | 0.81 | D283MED(98.98%) |
| DoTc24510 | 105 | 0.80 | DOTC24510(98.97%) |
| MCCAR | 84 | 0.80 | MCCAR(98.52%) |
| OCI-LY7 | 105 | 0.80 | OCILY7(98.04%) |
| A253 | 141 | 0.79 | A253(98.06%) |
| JAR | 79 | 0.79 | JAR(98.33%) |
| SU-DHL-6 | 134 | 0.79 | SUDHL6(99%) |
| SR | 66 | 0.79 | SR(99.46%) |

TABLE 9-continued

Authentication of cell lines

| Cell line | # of informative SNPs | Heterogeneity ratio (percentage) | Cell line inferred* |
|---|---|---|---|
| AN3CA | 107 | 0.78 | AN3CA(96.65%) |
| Hutu80 | 80 | 0.78 | HUTU80(100%), AZ521(100%) |
| OCUM-2M | 106 | 0.78 | OCUM2M(98.47%) |
| SW684 | 74 | 0.77 | SW684(98.98%) |
| SJCRH30 | 71 | 0.76 | SJCRH30(98.97%) |
| SW982 | 71 | 0.75 | SW982(99.48%) |
| Y-79 | 84 | 0.75 | Y79(97.38%) |
| MKN45 | 103 | 0.73 | MKN45(98.99%), GTL16(98.47%) |
| 143B | 91 | 0.72 | 143B(98.96%) |
| Molt-4 | 87 | 0.72 | MOLT4(98.98%), MOLT3(99.03%) |
| RT4 | 105 | 0.72 | RT4(99.11%) |
| HCT-8 | 93 | 0.71 | HCT8(98.5%) |
| NCI-H460 | 127 | 0.71 | NCIH460(99.53%) |
| SW480 | 141 | 0.71 | SW480(100%) |
| T.Tn | 129 | 0.71 | T.T(95.22%) |
| YCC-10 | 99 | 0.71 | YCC10(98.97%) |
| C-33A | 80 | 0.71 | C33A(98.51%) |
| ASH-3 | 99 | 0.67 | ASH3(97.06%) |
| SW626 | 112 | 0.66 | SW626(97.98%) |
| SW756 | 96 | 0.66 | SW756(99.02%) |
| A-875 | 80 | 0.63 | A875(98.06%) |
| CoC1 | 72 | 0.61 | COC1DDP(98.98%), CCRFCEM(98.98%), COC1(98.98%) |
| JurkatcloneE6-1 | 92 | 0.57 | JURKATCLONEE61(98.12%), JURKAT(98.08%) |

* genotype similarity shown in parenthesis

TABLE 10

Genotype similarities of related cell lines

| Cell line tested | Related cell line | Genotype similarity |
|---|---|---|
| Hela | SMMC7721 | 0.8431 |
| Hela | BEL7402 | 0.8529 |
| Hela | QGY7701 | 0.8657 |
| Hela | QGY7703 | 0.8683 |
| SW480 | SW620 | 0.8852 |
| NCIH1993 | NCIH2073 | 0.8932 |
| OCUM-2M | OCUM2D | 0.9 |
| 143B | HOS | 0.9179 |
| SR | SR786 | 0.9235 |
| SJCRH30 | RH30 | 0.932 |
| 143B | KHOSNP | 0.9563 |
| Hep3B | HEP3B217 | 0.9573 |
| HCT-8 | HCT15 | 0.9608 |
| HepG2C3A | HEPG2 | 0.9622 |
| HCCLM3 | MHCC97H | 0.9626 |

TABLE 11

Six informative genotype combinations to estimate heterogeneity/contamination ratio*

| Combination | 1 | 2 | 3 | 4 | 5 | 6 |
|---|---|---|---|---|---|---|
| S1 genotype | AA | AA | AA | AT | AT | AT |
| S2 genotype | TT | AT | TG | GG | AG | GC |
| S2 ratio (SNP heterogeneity ratio) | T/(A + T)** | 2T/(A + T)** | (T + G)/(A + T + G) | G/(A + T + G)*** | G/(T + G)*** | (G + C)/(A + T + G + C) |
| Nucleotide frequency pattern | large A small T | large A small T | large A small T and G | large A and T small G | large A and T small G | large A and T small G and C |

*S1 is the major component and S2 is the minor/contaminating component in the mixed sample. Each combination uses specific nucleotides to represent a class of combinations, for example, the first combination denotes that both are homozygous genotypes with different nucleotides In the formulas for calculating S2 ratio, a nucleotide denotes its count (total number of reads) in NGS sequencing data.
**Combinations 1 and 2 cannot be distinguished from observed NGS data so 1.5T/(A + T) is used for both
**Combinations 4 and 5 cannot be distinguished from observed NGS data so 1.5G/(A + T + G) is used for both

TABLE 12

Sequencing Primers

| Locus | Forward Primer | SEQ ID NO. | Reverse Primer | SEQ ID NO. |
|---|---|---|---|---|
| chr1_10473196 | ctgcatgtaggcctttgaggat | 545 | gggcccatgtgaaaagcataac | 546 |
| chr1_1222267 | gccggcaactctgactcc | 547 | tcaccagtctgaaccccact | 548 |
| chr1_1249187 | ccgacgggtgtggatgtg | 549 | cgagaaggccaaccactactac | 550 |
| chr2_10712278 | atcaatgaaacgaccgtcctctt | 551 | acggttaccagaaaagaggtatagaatt | 552 |
| chr2_109513601 | tgagtagctcagggatgctgta | 553 | cccacggagctgccattt | 554 |
| chr2_109543883 | cccactaattctgcagatggct | 555 | gcctggctacggttcagac | 556 |
| chr3_14174427 | cgggctctgagttgattcctc | 557 | aaacccatgtcccacattttcaac | 558 |
| chr3_50334231 | gcaatggaggtcccttggg | 559 | atggagggcctggaggtc | 560 |
| chr3_50355730 | tcaccactccagcccaagta | 561 | gccagtaccttcctgcatctc | 562 |
| chr4_1330759 | actacaccagctgggaaacaatt | 563 | tgggaggacaagagtggca | 564 |
| chr4_1737502 | cccgtgtgttaggggatg | 565 | cggcgcacatacctgct | 566 |
| chr4_183815688 | taagatcaaacacatcagcaatgagc | 567 | gcaaccaaagttttctttcttccc | 568 |
| chr5_141014494 | agccttgcatattggtgggg | 569 | ctctctactgacttaaggattgtggg | 570 |
| chr5_176940384 | ctccaatcagcttcagggagac | 571 | gcgacagaccctgctcttc | 572 |
| chr5_179290845 | ccaccacctggctctcct | 573 | aggacctgtaccacgccat | 574 |
| chr6_26545632 | agccacagaggagatcagct | 575 | agtacagagctctcaaaaatgtacatttc | 576 |
| chr6_2745352 | gagagcacagacaaccccg | 577 | ctcgtgttgtatttccccagat | 578 |
| chr10_102746503 | ccattgatgggttccatttgcc | 579 | gaccacgttccgcggg | 580 |
| chr10_1046712 | tggaggataggaacaccatcga | 581 | acacacaccttgttgatgaagaga | 582 |
| chr10_99219885 | gcatggaagccctggacc | 583 | ccctgatgtacctcaaaggctc | 584 |
| chr11_118967758 | cccaggagtgccaatgatcaca | 585 | agtccatttctccttgcagatcc | 586 |
| chr11_120107411 | gggacagggagtatcaggct | 587 | ctctctcagacttgctcactgatc | 588 |
| chr11_3028140 | cagccccgggagctct | 589 | ccatgtctgagggaactgctc | 590 |
| chr12_109994870 | agggatcctccaagctccc | 591 | ggcttgatctctcatttcaaaccat | 592 |
| chr12_112037000 | atggtgaggggcccataca | 593 | gactgttttggtagcaacggc | 594 |
| chr12_6638116 | cgaccccgagcctcaga | 595 | caatacttcatgatggtgtggaaagg | 596 |
| chr13_111298392 | gctccatgagttcctccacag | 597 | cagcaccaagagggccg | 598 |
| chr13_115004914 | gatgagcggcacttctgttttc | 599 | ttctgccacgtaatgagggc | 600 |
| chr14_105222037 | agactcaatggccatgcagg | 601 | atctgcccacgtgcagc | 602 |
| chr14_106208082 | gatgtcgctgggatagaagcc | 603 | aaccatctccaaagccaaggt | 604 |
| chr14_24736027 | gggtcctgcacatctccttg | 605 | ccatcacctccttcctccct | 606 |
| chr15_40328665 | gtgaaagcaggaaatgtatgccc | 607 | ggcttattcaaacctcctagagcta | 608 |
| chr15_44038899 | gacaacttcgagagtcgcatct | 609 | cacaggaatgaagggcccc | 610 |
| chr15_75189930 | gtctgagctgcactgccttat | 611 | gacagcaggcacggaatatca | 612 |
| chr16_11773662 | gtgcccccgctgtaagac | 613 | tctctccagaaaggacctaagtgt | 614 |
| chr16_15129970 | cctgcgaggttcagatgctt | 615 | gctctccggtccttctacct | 616 |
| chr16_2049640 | gccgagcgctgggaag | 617 | ccccgcccgctacct | 618 |
| chr17_19247075 | attttgtgggctagctcctatgtg | 619 | acctgtgttcttctgtgttccc | 620 |
| chr17_38179492 | tcaaagatgtggatggagcgg | 621 | gcagacagccacgcagat | 622 |
| chr17_40722029 | gccattcctgggagtacacag | 623 | cacgctgacagctcctgg | 624 |
| chr18_12351342 | ctacactcatgagcactggacc | 625 | ttgttatctttcaggttttaatacaacaacaat | 626 |
| chr18_33750046 | gatgcttgaaatgctctcaagtcc | 627 | gggccaatgttgtgctcaatac | 628 |
| chr18_77805856 | gagccgaccacaagctcc | 629 | caggtcatcttcaacctcctcg | 630 |
| chr19_10226256 | ggacaccccggcaatgg | 631 | tcccgcatctacctggctaa | 632 |
| chr19_1110829 | cgaaggtgtctgagaagtactgg | 633 | cgtggagaagggtgagtgc | 634 |
| chr19_13885484 | ctgaaaagaatcggggccca | 635 | ctgatcccgggctcca | 636 |
| chr20_25260931 | gctttcagagggctccagatc | 637 | gcgctccaaggcctcag | 638 |
| chr20_3193978 | tctgtttccctgataagtgccg | 639 | tggcaaaggaaggcagtgtt | 640 |
| chr20_391170 | attcccagattcctcatggtgc | 641 | cgaaccctgaattctagctgaata | 642 |
| chr21_38568308 | ctgatcggaagcagcctgtt | 643 | atcaggaaacctcagttcgataaagtat | 644 |
| chr21_46271452 | ctgcaagacgagaggactgtc | 645 | gtttaaagaagaaaacccgtatgctagat | 646 |
| chr22_32795641 | ttgccctccaaagtgagttac | 647 | actagcacctttatacttatccagagac | 648 |
| chr22_38273749 | ctccaccccatccccagat | 649 | aaagttcttcatagacttgtgggtca | 650 |
| chr22_39134715 | cgaagtccttgggggcac | 651 | gcacactgagggctggtc | 652 |

What is claimed is:

1. A method for determining the authentication of a human or mouse sample, the method comprising:
   obtaining a nucleic acid from the human or mouse sample;
   providing a set of oligonucleotide primer pairs, wherein each oligonucleotide primer pair in the set flanks a single locus in a set of single nucleotide polymorphism (SNP) loci of (i) SEQ ID NOs: 1-237 or (ii) SEQ ID NOs: 238-436, and wherein each oligonucleotide primer pair is capable of amplifying a single locus from the set of SNP loci in a multiplex amplification reaction;
   co-amplifying the set of SNP loci in a multiplex amplification reaction, wherein the product of the multiplex amplification reaction comprises a mixture of amplified alleles from each of the co-amplified loci in the set of SNP loci;

evaluating the products of the co-amplification reaction to determine the alleles present at each of the set of SNP loci within the human or mouse sample;

comparing the alleles present at each of the set of SNP loci within the sample with alleles present at each of the set of SNP loci in a human or mouse reference sample; and determining whether (i) the human or mouse sample is the same as the human or mouse reference sample, or (ii) the human or mouse sample contains a contaminant other than the human or mouse reference sample.

2. The method of claim 1, wherein the human or mouse sample is a cell, a tissue, an organoid, or a combination thereof.

3. The method of claim 2, wherein the human or mouse sample is a cell line or a tumor tissue.

4. The method of claim 1, wherein the human or mouse sample contains a contaminant, the method further comprising determining the percentage of the contaminant in the human or mouse sample.

5. The method of claim 1, wherein the human or mouse sample contains a contaminant, the method further comprising determining the identity of the contaminant.

6. The method of claim 1, wherein the products of the co-amplification reaction are evaluated by next-generation sequencing (NGS).

7. The method of claim 1, wherein the nucleic acid is barcoded.

8. The method of claim 1, further comprising identifying the gender of a subject from which the sample is obtained by analyzing at least one sex chromosome SNP locus.

9. The method of claim 1, wherein the human or mouse sample is a mouse sample from a mouse tumor model selected from the group consisting of 4T1, A20, B16-BL6, B16-F0, B16-F1, B16-F10, C1498, Colon26, CT26WT, E.G7-Ova, EL4, EMT6, H22, Hepa1-6, J558, J774A1, JC, KLN205, L1210, L5178-R, LLC, MBT2, MC38, MPC-11, Neuro-2a, P388D1, P815, Pan02, Renca, RM1, S91, and WEHI164.

* * * * *